US012653595B2

(12) United States Patent
Taber et al.

(10) Patent No.: US 12,653,595 B2
(45) Date of Patent: Jun. 16, 2026

(54) ARTICULATING SURGICAL TOOLS

(71) Applicant: Pro-Dex, Inc., Irvine, CA (US)

(72) Inventors: Justin Taber, Irvine, CA (US); Daniel Manuel Santos, Irvine, CA (US)

(73) Assignee: Pro-Dex, Inc., Irvine, CA (US)

( * ) Notice: Subject to any disclaimer, the term of this patent is extended or adjusted under 35 U.S.C. 154(b) by 288 days.

(21) Appl. No.: 18/339,169

(22) Filed: Jun. 21, 2023

(65) Prior Publication Data

US 2023/0414264 A1 Dec. 28, 2023

Related U.S. Application Data

(60) Provisional application No. 63/354,656, filed on Jun. 22, 2022.

(51) Int. Cl.
*A61B 17/88* (2006.01)
*A61B 17/00* (2006.01)
(Continued)

(52) U.S. Cl.
CPC .. *A61B 17/8875* (2013.01); *A61B 2017/0046* (2013.01); *A61B 2017/00477* (2013.01);
(Continued)

(58) Field of Classification Search
CPC .............. A61B 17/8875; A61B 17/162; A61B 17/1622; A61B 17/1624; A61B 17/1626;
(Continued)

(56) References Cited

U.S. PATENT DOCUMENTS

| | | | |
|---|---|---|---|
| 4,662,814 A | 5/1987 | Suzuki et al. | |
| 5,484,440 A | 1/1996 | Allard | |

(Continued)

FOREIGN PATENT DOCUMENTS

| | | |
|---|---|---|
| EP | 2364825 A1 | 9/2011 |
| JP | 2014-155826 A | 8/2014 |

(Continued)

OTHER PUBLICATIONS

Petrzelka et al., "An Articulating Tool for Endoscopic Screw Delivery," Proceedings of the 2010 Design of Medical Devices Conference, Apr. 13-15, 2010, in 8 pages.
(Continued)

*Primary Examiner* — Marcela I. Shirsat
(74) *Attorney, Agent, or Firm* — Knobbe, Martens, Olson & Bear, LLP

(57) ABSTRACT
Various articulating tools for driving fasteners or other surgical implements are disclosed. The articulating tool may be removably connected to a handpiece comprising a motor. The articulating tool may include a torque transmission mechanism that includes a first shaft that extends through the lumen of the elongate outer housing. The first shaft may transfer the torque from the motor to an articulating torque transmission unit. The articulating torque transmission unit may transfer the torque to the bit that interlocks to the fastener. The articulating tool may include an orientation mechanism that is separate from the torque transmission mechanism. The orientation mechanism can have one or more controllers to rotate the articulating unit and driver head adapter about one or more axes.

17 Claims, 44 Drawing Sheets

(51) Int. Cl.

| | |
|---|---|
| *A61B 17/16* | (2006.01) |
| *B25B 21/00* | (2006.01) |
| *B25B 23/00* | (2006.01) |
| *B25B 23/142* | (2006.01) |

(52) U.S. Cl.
CPC ......... *A61B 17/162* (2013.01); *A61B 17/1624* (2013.01); *A61B 17/1626* (2013.01); *A61B 17/1631* (2013.01); *A61B 17/8877* (2013.01); *A61B 17/8886* (2013.01); *B25B 21/002* (2013.01); *B25B 21/007* (2013.01); *B25B 23/0007* (2013.01); *B25B 23/0028* (2013.01); *B25B 23/0042* (2013.01); *B25B 23/142* (2013.01); *B25B 23/1427* (2013.01)

(58) Field of Classification Search
CPC ............ A61B 17/1631; A61B 17/8877; A61B 17/888; A61B 17/8883; A61B 17/8886; A61B 17/16; A61B 2017/0046; A61B 2017/00477; B25B 23/0021; B25B 23/0028; B25B 23/0035; B25B 23/0042; B25B 23/00; B25B 23/0007; B25B 23/0014; B25B 23/14; B25B 23/142; B25B 23/1427; B25B 17/00; B25B 21/00; B25B 21/002; B25B 21/007; B25B 33/00; B25B 33/005
USPC ........................................................ 606/104
See application file for complete search history.

(56) References Cited

U.S. PATENT DOCUMENTS

| | | | |
|---|---|---|---|
| 5,660,491 | A | 8/1997 | Roberts et al. |
| 6,658,962 | B1 | 12/2003 | Rosheim |

| | | | |
|---|---|---|---|
| 9,140,344 | B2 | 9/2015 | Teng et al. |
| 9,265,551 | B2 | 2/2016 | Kust et al. |
| 9,421,003 | B2 | 8/2016 | Williams et al. |
| 11,259,855 | B2 | 3/2022 | Bowen et al. |
| 12,201,338 | B2 | 1/2025 | Bowen et al. |
| 2002/0183762 | A1 | 12/2002 | Anderson et al. |
| 2009/0023988 | A1 | 1/2009 | Komer et al. |
| 2011/0152867 | A1 | 6/2011 | Petrzelka et al. |
| 2011/0301416 | A1 | 12/2011 | Dejima et al. |
| 2012/0266709 | A1 | 10/2012 | Wang |
| 2012/0271285 | A1 | 10/2012 | Sholev et al. |
| 2014/0236174 | A1 | 8/2014 | Williams et al. |
| 2016/0106442 | A1 | 4/2016 | Guo et al. |
| 2017/0281171 | A1 | 10/2017 | Shelton, IV et al. |
| 2018/0021960 | A1 | 1/2018 | Grant et al. |
| 2020/0214754 | A1* | 7/2020 | Bowen ................... A61B 17/56 |
| 2022/0338914 | A1 | 10/2022 | Bowen et al. |
| 2025/0160919 | A1 | 5/2025 | Bowen et al. |

FOREIGN PATENT DOCUMENTS

| | | | |
|---|---|---|---|
| WO | WO 2011/019206 A2 | 2/2011 |
| WO | WO 2011/092692 A2 | 8/2011 |
| WO | WO 2019/032729 A1 | 2/2019 |
| WO | WO 2023/250331 | 12/2023 |

OTHER PUBLICATIONS

Invitation to Pay Additional Fees in corresponding international Patent Application No. PCT/US2023/068746, dated Aug. 10, 2023, in 3 pages.
Search Report and Written Opinion in corresponding international Patent Application No. PCT/US2023/068746, dated Sep. 28, 2023, in 17 pages.

* cited by examiner

*700*

*730*

*116*

*126*

*124*

*1010*

*1850*

*1910*

29

*1905*

*2305*

*2300*

*112*

*1825*

*3000*

*3005*

*3010*

*3005*

*3005*

*3010*

3305

3400

3310

3315

3300

3320

ARTICULATING SURGICAL TOOLS

CROSS REFERENCE

This application claims the benefit of priority to U.S. Patent Application No. 63/354,656, filed Jun. 22, 2022, which is hereby incorporated by reference herein in its entirety. Additionally, any applications for which a foreign or domestic priority claim is identified in the Application Data Sheet as filed herewith are hereby incorporated by reference under 37 CFR 1.57.

BACKGROUND

This disclosure relates to articulating tools for the placement of fasteners in medical procedures, such as tools for placing screws in endoscopic surgical procedures.

Surgical tools play an important role in medical operations, such as in orthopedic surgery where precise and effective fixation of bones and/or implements (e.g., plates) is essential. The process of inserting screws into bones was traditionally performed manually using handheld screwdrivers. This method requires skill and precision on the part of the surgeon, particularly in endoscopic surgical procedures, as well as the application of manual force. The reliance on manual force may poses challenges, such as in cases where dense bones or complex anatomical structures are involved. Additionally, there is a significant risk of human error, including misplacement or inadequate fixation of the screw, implement, and/or bone.

SUMMARY OF CERTAIN ASPECTS

Powered surgical screwdrivers represent a significant advancement in the field of surgical tools. Powered screwdrivers may include electric systems that enable surgeons to drive screws into bones more efficiently. However, these tools may lack control, stability, and accuracy while operating in tight spaces or at certain angles. Additionally, certain powered screwdrivers may be inconvenient or unable to operate at certain angles and/or to reach certain anatomical structures. For example, certain powered screwdrivers may be unable to be inserted into a patient in one direction (e.g., generally parallel to a longitudinal axis of the tool) and to drive a screw in a different direction (e.g., generally perpendicular to the longitudinal axis of the tool). Some powered screwdrivers are fixed (e.g., relative to a handle of the tool) in the angle at which the screw is driven. This can, for example, limit or eliminate the tool's ability to adapt the drive angle to compensate for the particularities of bodily structures during a medical procedure. The present disclosure relates to articulating tools that address one or more of the aforementioned concerns, or other concerns.

The present disclosure describes an articulating surgical driver for securing screws, plates, or other medical implants to a patient during a surgical procedure. The surgical driver may be a powered or non-powered (e.g., motorized or non-motorized) screwdriver that fastens screws into a patient's bones, tendons, or muscles. The surgical driver can have an adjustable head that rotates about two axes, which can be spaced apart and/or oriented in different directions. In some embodiments, the adjustable head can tilt up or down about the surgical driver's short axis (e.g., the transverse axis) and rotate about the surgical driver's long axis (e.g., the longitudinal axis). In some implementations, the surgical driver can have an adjustable head that is a turret that rotates freely about the surgical driver's short axis. Advantageously, the surgical driver can operate (e.g., transfer torque from the motor to the bit) while the adjustable head is in any orientation. Thus, a user can easily drive and/or fasten a medical implant (e.g., a screw) after positioning the adjustable head in a desired orientation independent of the orientation of a handgrip of the driver. In several implementations, the articulating surgical driver allows users to easily reach (e.g., position a fastener in) a wide range of positions and configurations during medical procedures.

In some implementations, the orientation of the adjustable head is controlled via two control elements, such as two knobs. The first control knob rotates or tilts the adjustable head about the surgical driver's short axis, while the second control knob rotates the adjustable head about the surgical driver's long axis. Each control knob actuates a shaft of the surgical driver. In some variants, the first control knob actuates a first shaft that is connected to a gear assembly configured to rotate or tilt the adjustable head. The second control knob rotates a second shaft that is connected directly to the adjustable head. The control knobs allow a user to easily maneuver the surgical driver into a desired position while the surgical driver is in a confined area. The surgical driver can be used to perform minimally invasive surgery or orthopedic surgeries, such as craniomaxillofacial surgery, hand or foot surgery, and spine surgery. Thus, the articulating surgical driver provides a medical professional or other user with an efficient, safe, and precise tool for securing implants.

In some aspects, the technologies (also referred to as techniques) described herein relate to an articulating surgical tool. The articulating tool including an elongate outer housing including a proximal end, a distal end, a lumen, and a longitudinal axis. The elongate outer housing configured to engage with a handpiece including a motor. The articulating tool including a torque transmission mechanism including a first shaft that extends through the lumen of the elongate outer housing, and an articulating torque transmission unit having a first end and a second end. The first end being coupled to a distal portion of the first shaft. The articulating torque transmission unit having a first bevel gear, a second bevel gear, and a third bevel gear. The first bevel gear can be fixedly coupled to the first shaft. The second bevel gear can be coupled to a gear support shaft. The third bevel gear can be configured to removably engage with a bit and to rotate the bit around a bit axis. The torque transmission mechanism can be configured to transmit torque from the motor to the bit. Rotating the elongate outer housing can be configured to rotate the torque transmission mechanism around the longitudinal axis.

The articulating tool including an orientation mechanism that can be separate from the torque transmission mechanism. The orientation mechanism including a second shaft extending through the lumen of the elongate outer housing, wherein the first shaft and second shaft are concentric. The orientation mechanism including a fourth bevel gear and a fifth bevel gear. The fourth bevel gear can be fixedly coupled to the second shaft. The fifth bevel gear can be coupled to a driver head adapter. The orientation mechanism can include a controller connected to a proximal portion of the second shaft. The controller can be configured to rotate the second shaft. The rotation of the second shaft can rotate the driver head adapter around a transverse axis. the transverse axis can be generally perpendicular to the longitudinal axis.

In some aspects, the techniques described herein relate to an articulating surgical tool, wherein the second bevel gear can be a double-sided bevel gear.

In some aspects, the techniques described herein relate to an articulating surgical tool, wherein the bit axis is non-coplanar with the longitudinal axis.

In some aspects, the techniques described herein relate to an articulating surgical tool, wherein the second bevel gear is between the longitudinal axis and the bit axis.

In some aspects, the techniques described herein relate to an articulating surgical tool, wherein the bit is a bone drill bit.

In some aspects, the techniques described herein relate to an articulating tool configured to facilitate placement of surgical implement, such as a fastener (e.g., screw) or drill bit, during a medical procedure. The articulating tool can include an elongate outer housing including a proximal end, a distal end, a lumen, and a longitudinal axis. The elongate outer housing can be configured to engage with a handpiece including a motor. The articulating tool can be include a torque transmission mechanism. The torque transmission mechanism can include a first shaft that extends through the lumen of the elongate outer housing. The torque transmission mechanism can include an articulating torque transmission unit having a first end and a second end. The first end can be coupled to a distal portion of the first shaft. A driver head adapter can be positioned at the second end of the articulating torque transmission unit.

The driver head adapter can be configured to removably engage with a bit and to rotate the bit around a bit axis. The bit can be configured to engage with a surgical implement, such as a fastener (e.g., screw) or drill bit. The torque transmission mechanism can be configured to transmit torque from the motor to the driver head adapter and the bit. Rotating the elongate outer housing can be configured to rotate the torque transmission mechanism around the longitudinal axis.

The articulating tool can include an orientation mechanism that is separate from the torque transmission mechanism. The orientation mechanism can include a second shaft extending through the lumen of the elongate outer housing. The orientation mechanism can include a controller connected to a proximal portion of the second shaft. The controller can be configured to rotate the second shaft. The driver head adapter can be connected to the distal portion of the second shaft. The rotation of the second shaft can rotate the driver head adapter around a transverse axis. The transverse axis can be generally perpendicular to the longitudinal axis.

In some aspects, the techniques described herein relate to an articulating tool, wherein the orientation mechanism includes a first bevel gear and second bevel gear. The first bevel gear can be fixedly coupled to the second shaft. The second bevel gear can be coupled to the driver head adapter.

In some aspects, the techniques described herein relate to an articulating tool, wherein the driver head adapter is configured to rotate about the transverse axis between about 0° to about 360°.

In some aspects, the techniques described herein relate to an articulating tool, wherein the driver head adapter is configured to complete multiple revolutions about the transverse axis.

In some aspects, the techniques described herein relate to an articulating tool, wherein the articulating torque transmission unit includes a first bevel gear, a second bevel gear, and a third bevel gear. The first bevel gear can be fixedly coupled to the first shaft. The second bevel gear can be coupled to a gear support shaft. The third bevel gear can be removably coupled to the bit.

In some aspects, the techniques described herein relate to an articulating tool, wherein the driver head adapter includes a lumen configured to receive a shaft of the bit. The driver head adapter can be coupled to the shaft of the bit via a quick-release mechanism.

In some aspects, the techniques described herein relate to an articulating tool, wherein the elongate outer housing is configured to rotate about the longitudinal axis relative to the controller between about 0° to about 360°.

In some aspects, the techniques described herein relate to an articulating tool, wherein the elongate outer housing is configured to complete multiple revolutions about the longitudinal axis relative to the controller.

In some aspects, the techniques described herein relate to an articulating tool, wherein the controller includes a wheel, wherein rotation of the wheel causes the second shaft to rotate.

In some aspects, the techniques described herein relate to an articulating tool, wherein the controller includes a locking clutch that locks the rotation of the second shaft.

In some aspects, the techniques described herein relate to an articulating tool, wherein the elongate outer housing is connected to a wheel, and wherein rotation of the wheel causes the elongate outer housing to rotate.

In some aspects, the techniques described herein relate to an articulating tool configured to facilitate placement of surgical implement, such as a fastener (e.g., screw) or drill bit, during a medical procedure. The articulating tool can include a multi-part elongate outer housing including an upper-portion, a lower-portion, a proximal end, a distal end, a lumen, and a longitudinal axis. In certain implementations, the multi-part elongate outer housing can be configured to engage with a handpiece including a motor. The articulating tool can include a torque transmission mechanism including a first shaft that extends through the lumen of the multi-part elongate outer housing. The torque transmission mechanism can include an articulating torque transmission unit having a first end and a second end. The first end can be coupled to a distal portion of the first shaft. The torque transmission mechanism can include a driver head adapter that is positioned at the second end of the articulating torque transmission unit. The driver head adapter can be configured to removably engage with a bit and to rotate the bit around a bit axis. The bit can be configured to engage with a surgical implement, such as a fastener (e.g., screw) or drill bit. The torque transmission mechanism can include a controller. The controller can be configured to move (e.g., rotate) the articulating torque transmission unit, such as around a transverse axis. The transverse axis can be generally perpendicular to the longitudinal axis. The controller can be configured to move the articulating torque transmission unit, such as by advancing and/or retracting the upper-portion of the multi-part elongate outer housing. The torque transmission mechanism can be configured to transmit torque from the motor to the driver head adapter and the bit. Although the discussion above describes a multi-part elongate outer housing, certain implementations include an elongate outer housing that is singular and/or is not multi-part.

In some aspects, the techniques described herein relate to an articulating tool, wherein the articulating torque transmission unit includes first, second, third, and fourth bevel gears. The first bevel gear can be fixedly coupled to the first shaft. The second bevel gear can be coupled to a first gear support shaft. The third bevel gear can be coupled to a second gear support shaft. The fourth bevel gear can be removably coupled to the bit.

In some aspects, the techniques described herein relate to an articulating tool, wherein the second bevel gear includes a set of second bevel gears. The third bevel gear can include a set (e.g., a plurality) of third bevel gears.

In some aspects, the techniques described herein relate to an articulating tool, wherein the controller is configured to rotate the articulating torque transmission unit by advancing or retracting the lower-portion of the multi-part elongate outer housing.

In some aspects, the techniques described herein relate to an articulating tool, wherein rotating the multi-part elongate outer housing is configured to rotate the torque transmission mechanism around the longitudinal axis.

In some aspects, the techniques described herein relate to an articulating surgical screwdriver adaptor. The adaptor can include a proximal end having a body configured to removably connect to a rotational driver and/or a drive output (e.g., a drive shaft). The proximal end can be configured to connect with a powered or non-powered driver, such as a driver with an electric motor or a driver with a handle that is manually turned. The articulating surgical screwdriver adaptor can include a distal end having a driver head adapter. The driver head adapter can be configured to articulate and rotate relative to the body. The driver head adapter can be configured to removably receive a driver head engageable with a surgical implement, such as a fastener (e.g., screw) or drill bit. The articulating surgical screwdriver adaptor can include an orientation control unit. The orientation control unit can be configured to control articulation of the driver head adapter. The articulating surgical screwdriver adaptor can include a torque transmission unit. The torque transmission unit can be configured to removably connect with the drive output and/or to convey torque from the drive output to the driver head adapter such that the driver head rotates the surgical implement.

In some aspects, the techniques described herein relate to a combination including the articulating surgical screwdriver adaptor, the surgical driver, and the driver head.

In some aspects, the techniques described herein relate to an articulating surgical screwdriver adaptor, wherein the orientation control unit includes an arm and is configured to convert transverse movement of the arm into rotational movement of the driver head adapter.

In some aspects, the techniques described herein relate to an articulating surgical screwdriver adaptor, wherein the orientation control unit includes an arm and is configured to convert rotational movement of the arm into rotational movement of the driver head adapter.

In some aspects, the techniques described herein relate to an articulating surgical screwdriver adaptor, wherein the driver head adapter includes first and second gears. The first and second gears can be configured to rotate about respective axes that are generally parallel to each other and/or are generally perpendicular to a longitudinal axis of the articulating surgical screwdriver adaptor.

In some aspects, the techniques described herein relate to an articulating surgical screwdriver adaptor, wherein the orientation control unit includes a spring-biased clutch. The spring can comprise, for example, a coil spring, leaf spring, or helical spring, wave spring, or otherwise.

In some aspects, the techniques described herein relate to an articulating surgical screwdriver adaptor. The adaptor can include a proximal end configured to removably connect to a surgical driver having a drive output, such as a surgical driver having an electric motor. The articulating surgical screwdriver adaptor can include a distal end configured to removably connect to the proximal end. The distal end can include a driver head adapter can be configured to articulate and rotate relative to the proximal end. The driver head adapter can be configured to removably receive a driver head engageable with a surgical implement, such as a fastener or drill bit. The articulating surgical screwdriver adaptor can include an orientation control unit configured to control articulation of the driver head adapter. The articulating surgical screwdriver adaptor can include a torque transmission unit configured to removably connect with the drive output and to convey torque from the drive output to the driver head adapter such that the driver head rotates the surgical implement.

In some aspects, the techniques described herein relate to an articulating surgical screwdriver adaptor, wherein the distal end further includes a quick-release mechanism.

In some aspects, the techniques described herein relate to an articulating surgical screwdriver adaptor, wherein the quick-release mechanism includes opposing first and second spring-biased buttons.

In some aspects, the techniques described herein relate to an articulating surgical screwdriver adaptor, wherein the proximal end includes first and second guide pins that are configured to removably engage with the quick-release mechanism.

The preceding Summary, following Detailed Description, and associated Drawings do not limit or define the scope of protection.

BRIEF DESCRIPTION OF THE DRAWINGS

Throughout the drawings, reference numbers are re-used to indicate correspondence between referenced elements. The drawings are provided to illustrate certain aspects of the subject matter described herein, not to limit the scope thereof.

DETAILED DESCRIPTION OF CERTAIN EMBODIMENTS

Figure 1:
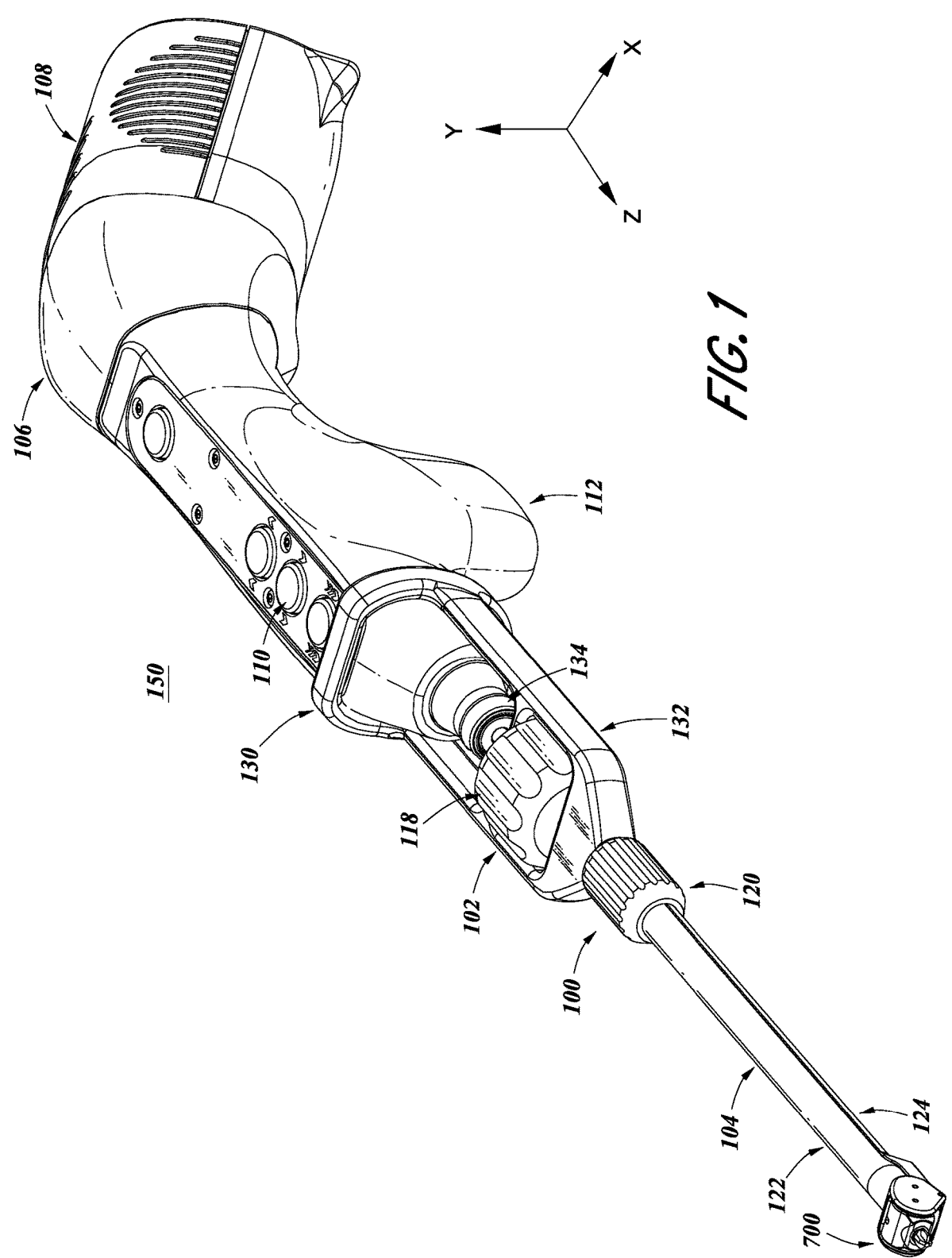
FIGS. 1 and 2A illustrate a front perspective view and a side view, respectively, of an embodiment of a fastening system that includes an articulating tool and handpiece.

In surgical procedures, inserting screws into a bone, or drilling holes with a drill bit, can be challenging due to the location and/or orientation of the bone, the surrounding anatomical structures (for example, muscles, ligaments, tendons, blood vessels, nerves, or otherwise), the shape and condition of the bone, and/or otherwise. In certain surgical procedures, there can be limited access to a desired insertion location and/or angle for the screw on the bone. Retracting or repositioning a fastening tool to adjust the insertion location and/or angle may be time-consuming, cause trauma to the patient, and/or be inconvenient or impractical (such as when a direct entry path for the fastening tool is blocked by other anatomical structures).

A fastening tool having an extension with flexible or elastomeric portions may aid in navigating a driver head in the patient's body. However, the flexible or elastomeric portions may not efficiently transmit a torque sufficient for inserting a screw into the cortex of the bone, among other issues.

A fastening tool with a rigid and/or non-flexible and/or non-elastomeric extension that can change direction may aid in navigating a driver head in the patient's body, while also efficiently transmitting a torque. In some embodiments, such an extension can include an articulating component that is configured to articulate at multiple angles in multiple axes. This can allow the fastening tool to adjust (e.g., bend or pivot) to access tight spaces, reduce a frequency of a user readjusting the position, and/or provide a desired orientation of the fastening tool. It can be beneficial that the fastening tool can, at the same time, maintain sufficient torque outputs to perform the intended function (e.g., to insert a fixation screw into the bone). In some embodiments, the extension comprises an adaptor that is configured to connect (e.g., removably) to the fastening tool, such as an existing powered driver.

It can be beneficial to have an extension with an articulating component that has an outer profile comparable to a standard non-articulating fastening tool. A smaller outer profile can reduce the need for a larger-sized access portal (e.g., a trocar) and/or allow the fastening tool with the articulating component to access spaces that are usually accessible by the standard non-articulating fastening tool.

In some implementations, gearing (e.g., bevel or miter gears) can provide improved overall range for the articulating component, such as an articulating driver head. It can be desirable to use gears and gearing mechanisms that will fit into the available space while maintaining sufficient torque outputs to perform the original function. Any type of gears (e.g., spur gears, helical gears, worm gears, internal gears, etc.) may be used for any of the gear assemblies described herein.

Several embodiments of an articulating tool for endoscopic placement of fasteners are disclosed herein that provide one or more of the above-described benefits, or other benefits. Several embodiments of the articulating tool can be used with fastener driving bits, drill bits, or otherwise.

Any of the structures, materials, steps, or other features disclosed above, or disclosed elsewhere herein, can be used in any of the embodiments in this disclosure. Any structure, material, step, or other feature of any embodiment can be combined with any structure, material, step, or other feature of any other embodiment to form further embodiments, which are part of this disclosure.

Various features and advantages of the disclosed technology will become more fully apparent from the following description of the several specific embodiments illustrated in the figures. These embodiments are intended to illustrate the principles of this disclosure. However, this disclosure should not be limited to only the illustrated embodiments. The features of the illustrated embodiments can be modified, combined, removed, and/or substituted as will be apparent to those of ordinary skill in the art upon consideration of the principles disclosed herein. No features, structure, or step disclosed herein is essential or indispensable.

Articulating Tool with Torque Transmission Unit (FIGS. 1-17)

Figure 2A:
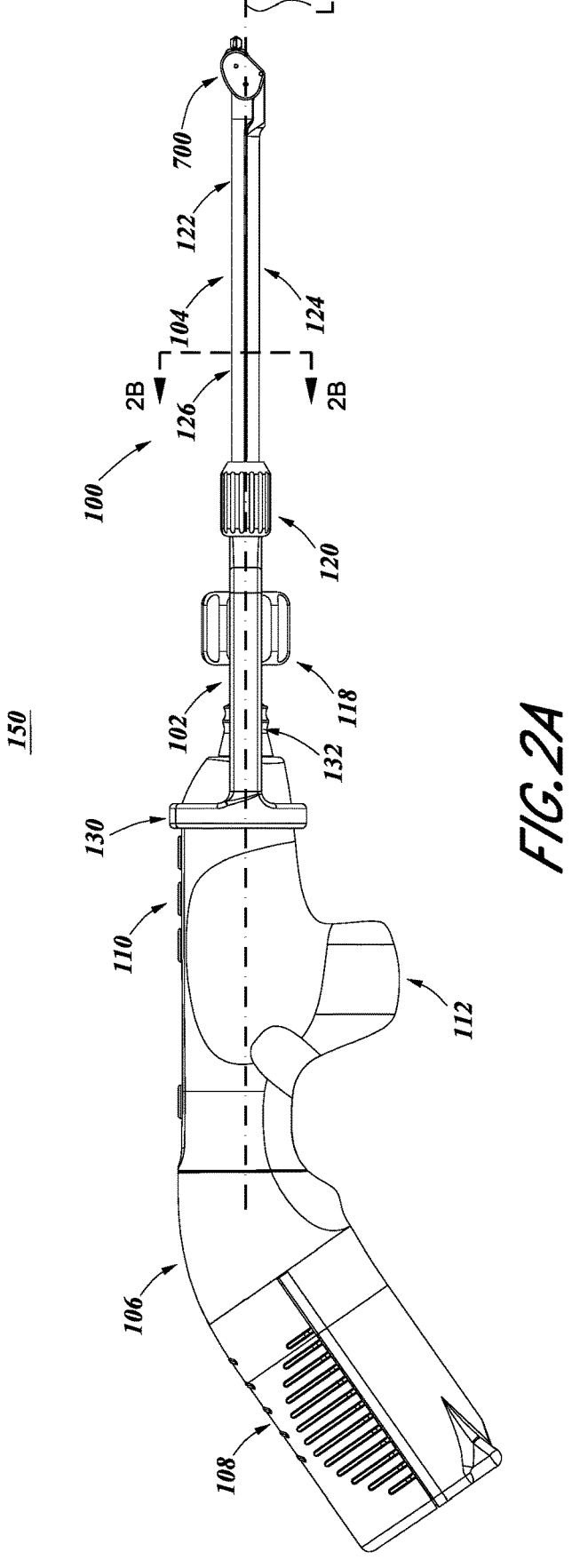
Figure 2B:
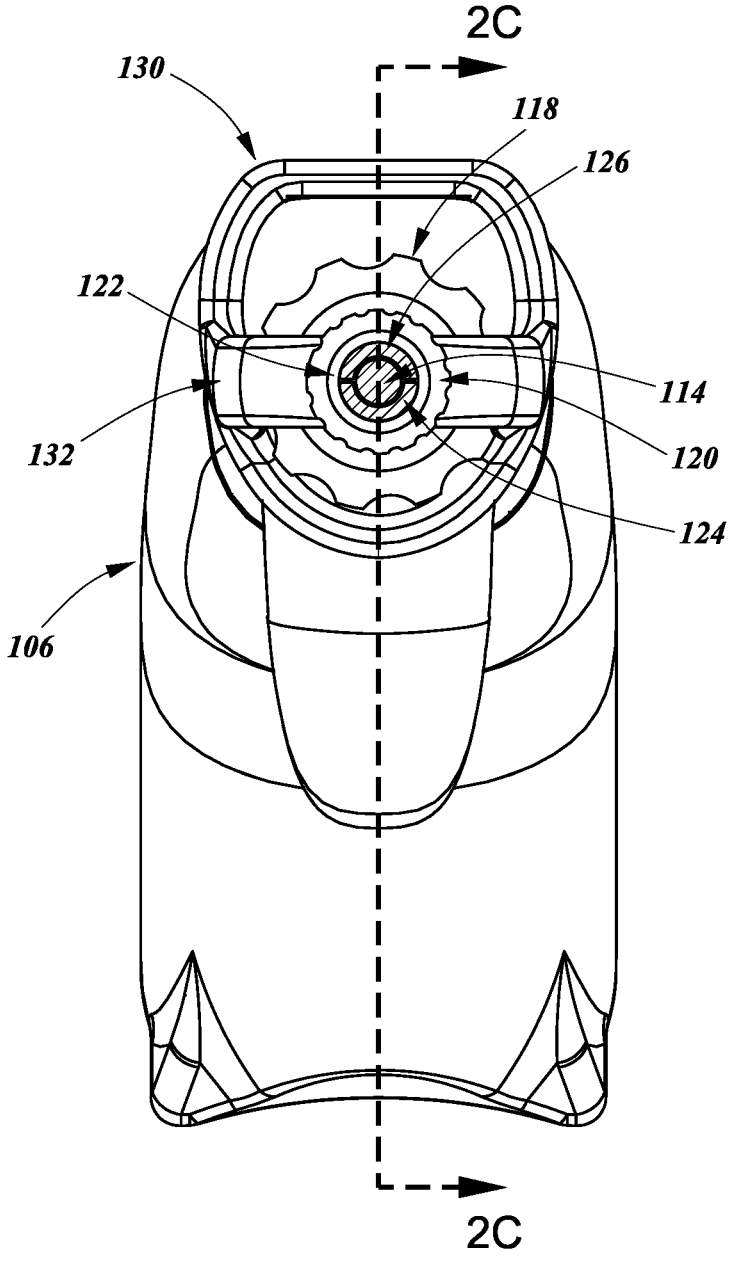
FIGS. 2B and 2C illustrate a front cross-section and side cross-section respectively of the fastening system of FIG. 2A.
Figure 2C:
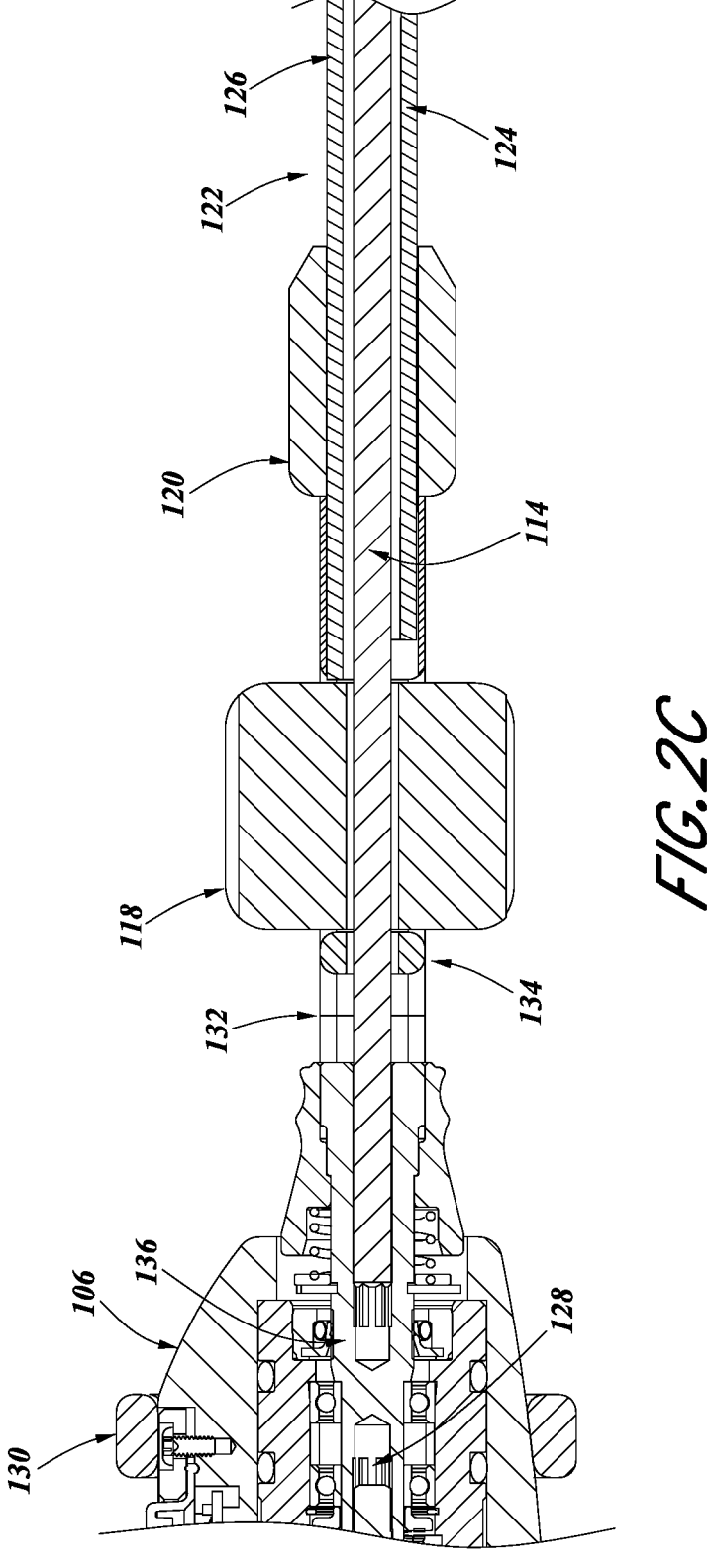
Figure 3:
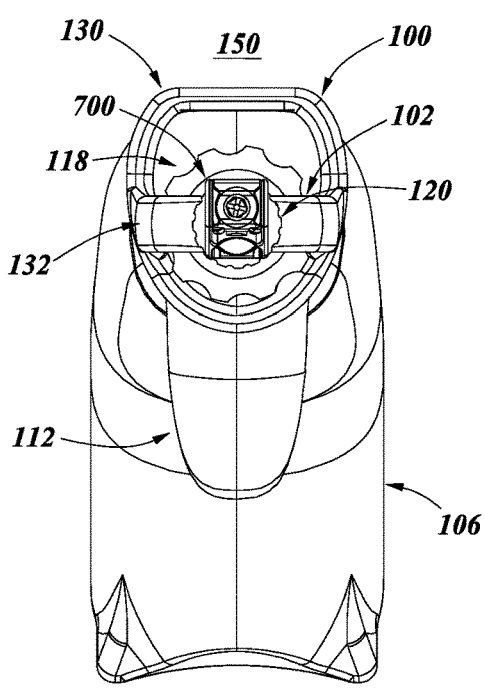
FIGS. 3 and 4 illustrate a front and a back view, respectively, of the fastening system of FIGS. 1 and 2A-2C.
Figure 4:
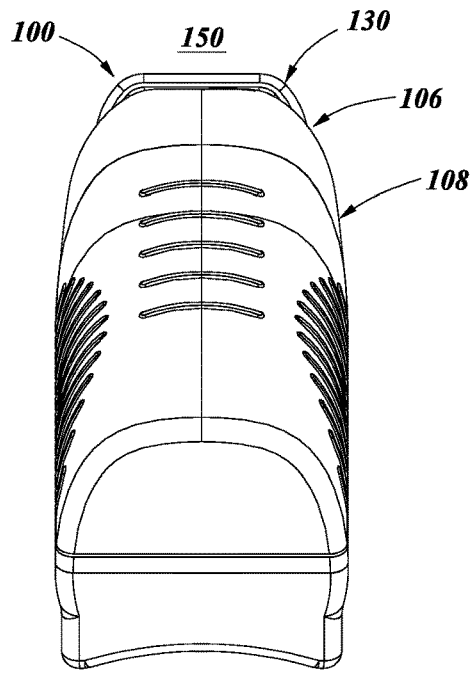

FIGS. 1 and 2A illustrate a front perspective view and a side view, respectively, of an embodiment of a fastening system 150 that includes an articulating tool 100 and handpiece 106. FIGS. 2B and 2C illustrate a front cross-section and side cross-section respectively of the fastening system 150. FIGS. 3 and 4 illustrate a front and a back view, respectively, of the fastening system 150. The fastening system 150 may be configured to facilitate the placement of surgical implements, such as a fasteners (e.g., screws) or drill bits, during a medical procedure, such as in an endoscopic surgical procedure. As shown, the articulating tool 100 can have a longitudinal axis L.

The articulating tool 100 can include a body coupling assembly 102 and a fastening tool 104. The body coupling assembly 102 may have a proximal end and a distal end. The distal end may be the end closest to a handpiece 106, and the distal end may be the end furthest from the handpiece 106. In some embodiments, the proximal end of the body coupling assembly 102 may have a stabilizing ring 130 that surrounds the distal end of the handpiece 106 (e.g., the end that attaches to the body coupling assembly 102). In some embodiments, the stabilizing ring 130 may couple to the body coupling assembly 102 by creating a friction fit with the handpiece 106. Alternatively, the stabilizing ring 130 may have a magnet, latch, clamp, and/or any other coupling mechanism described herein that couples with a corresponding mechanism on the handpiece 106.

As illustrated, the body coupling assembly 102 may have one or more arms 132 (e.g., two arms 132). In some embodiments, the arms 132 may connect the proximal and distal sections of the body coupling assembly 102 while creating an open central area. The open central area may provide space for one or more control wheels 118, 120, and one or more shafts (e.g., an internal shaft 114 and/or output shaft 128). Advantageously, the arms 132 increase the stability and functionality of the body coupling assembly 102 while reducing the weight and size of the body coupling assembly 102. In some embodiments, the body coupling assembly 102 includes a bridge 134 that connects the arms 132 at the center of the body coupling assembly 102 and creates two or more open central areas.

In some embodiments, the fastening tool 104 may extend from the distal end of the body coupling assembly 102. The fastening tool 104 may be a screwdriver, Allen wrench, hex key, or any other type of fastening driver or device. As illustrated, the articulating tool 100 can have x, y, and z axes. The articulating tool 100, and individual components thereof, may be made of metal (such as aluminum, steel, titanium, or iron) or non-metal (such as hard plastic). In some variants, components of the articulating tool 100 are made of a composite, such as a carbon fiber reinforced resin.

In some embodiments, the articulating tool 100 may include one or more control wheels 118, 120. The one or more control wheels 118, 120 may be digital and/or analog. The first control wheel 118 and the second control wheel 120 may be the same or different sizes. For example, in some implementations, the diameter of the first control wheel 118 may be 30 mm, and the diameter of the second control wheel 120 may be 20 mm. The diameter of the wheels may vary to accommodate different needs and user preferences. For instance, one or more of the wheels 118, 120 may have a diameter of 1 mm, 5 mm, 10 mm, 15 mm, 40 mm, more than 40 mm, or any diameter in-between. In some embodiments, the one or more control wheels 118, 120 may be positioned coaxially along the z-axis. For instance, the first control wheel 118 may be positioned in the middle of the body coupling assembly 102, and the second control wheel 120 may be positioned on the distal end of the body coupling assembly 102. In some embodiments, one or more control wheels 118, 120 may be positioned on the handpiece 106 or the fastening tool 104. In some embodiments, the one or more control wheels 118, 120 may be on two or more different axes (e.g., a first z-axis and a second z-axis that is offset from the first z-axis).

The fastening tool 104 can include a driver head adapter 700. In various embodiments, the driver head adapter 700 can swivel, articulate, move, rotate, and/or reposition relative to the handpiece 106. For example, the articulating tool 100 may have a multi-part (e.g., two-part shaft) 122 that is configured to rotate the driver head adapter 700 about the x-axis (e.g., an axis that is generally perpendicular to the longitudinal axis of the articulating tool 100), as discussed in more detail below. Thus, the multi-part shaft 122 may advantageously allow a user more control over the driver head adapter 700 and provide a greater range of positions for the driver head adapter 700 during an operation.

The multi-part shaft 122 can include a first portion (which can be a lower-shaft portion 124) and a second portion (which can be an upper-shaft portion 126). In some embodiments, the upper-shaft portion 126 moves independently from the lower-shaft portion 124. For example, the upper-shaft portion 126 may move (e.g., translate) axially along the z-axis (e.g., the longitudinal axis of the tool 100), such as either towards or away from the handpiece 106. In some embodiments, the lower-shaft portion 124 may move (e.g., translate) axially (e.g., along the z-axis), such as either towards or away from the handpiece 106. In some embodiments, the position of the upper-shaft portion 126 in relation to the position of the lower-shaft portion 124 determines the tilt of the driver head adapter 700. For example, in some implementations, a user can adjust (e.g., tilt or pivot) the driver head adapter 700 down by advancing the upper-shaft portion 126 and adjust (e.g., tilt or pivot) the driver head adapter 700 up by retracting the upper-shaft portion 126. In some variants, a user can tilt the driver head adapter 700 up by advancing the lower-shaft portion 124 and tilt the driver head adapter 700 down by retracting the lower-shaft portion 124.

In some implementations, one or both of the first and second portions rotate, such as relative to each other and/or to a handgrip of the tool 100. For example, in certain variants, rotating the first (or, alternatively, the second) portion in a first rotational direction can adjust (e.g., tilt or pivot) the driver head adapter 700 down by advancing the first (or, alternatively, the second) portion and rotating the first (or, alternatively, the second) portion in a second rotational direction can adjust (e.g., tilt or pivot) the driver head adapter 700 up by retracting the first (or, alternatively, the second) portion. A portion of the driver head adapter 700 can be, for example, threadably connected to the first and/or second portion to enable the movement (e.g., pivoting) of the driver head adapter 700.

In some embodiments, a user can adjust the position of the upper-shaft portion 126 and/or lower-shaft portion 124 via the one or more control wheels 118, 120 on the handpiece 106. For example, rotating the control wheel 118 in a first direction (e.g., clockwise) may advance the upper-shaft portion 126 forward (e.g., away from the handpiece 106) while the lower-shaft portion 124 remains stationary. Similarly, rotating the control wheel 118 in a second direction (e.g., counter-clockwise) may retract the upper-shaft portion 126 towards the handpiece 106. In some embodiments, the one or more control wheels 118 control the lower-shaft portion 124 or both parts of the multi-part shaft 122. For example, rotating the control wheel 120 clockwise may advance the upper-shaft portion 126 while simultaneously retracting the lower-shaft portion 124.

In certain implementations, the position of the driver head adapter 700 is adjustable and/or rotatable about the z-axis in response to actuation of the one or more control wheels 118, 120. For example, in certain embodiments, a user can rotate the fastening tool 104 relative to the handpiece 106 by turning the control wheel 120. In some embodiments, the tool 100 is configured to enable a user to tilt the driver head adapter 700 and rotate the fastening tool 104 (e.g., sequentially or simultaneously). For example, the control wheel 118 may be used to tilt the driver head adapter 700 while the control wheel 120 may be used to rotate the fastening tool 104. In certain implementations, such as is shown in FIG. 1, the driver head adapter 700 comprises a knuckle joint and/or can articulate as a knuckle.

In some embodiments, the position of the driver head adapter 700 may be adjusted via one or more operator controls 110. For example, in some embodiments, one or more operator controls 110 may be used to tilt and/or rotate the driver head adapter 700. In some embodiments, the fastening system 150 has one or more articulation motors that may be used to position the driver head adapter 700. In some implementations, a portion of the multi-part shaft 122 either advances or retracts in response to a user actuating (e.g., pressing) one or more operator controls 110 (e.g., buttons, switches, levers, arms, or otherwise). In certain implementations, the one or more operator controls 110 may be used to rotate the fastening tool 104 in relation to the handpiece 106. The operator controls 110 may be, for example, tactile and/or capacitive buttons.

In some embodiments, the handpiece 106 can include features to improve the user's control by aiding a user in grasping or directing the handpiece 106 and/or the articulating tool 100. For example, the handpiece 106 can include a fin 112 that allows a user to grip the handpiece 106 easily and securely. The fin 112 can comprise a pistol grip. In some variants, the tool 100 comprises a pencil grip.

Figure 5:
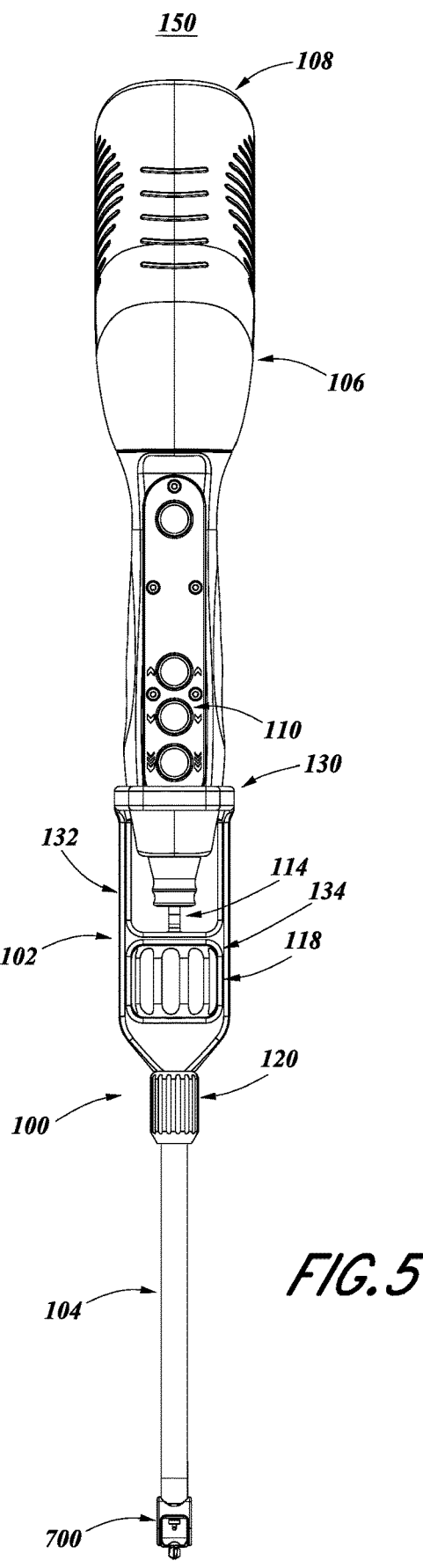
FIGS. 5 and 6 illustrate a top and a bottom view, respectively, of the fastening system of FIGS. 1 and 2A-2C.
Figure 6:
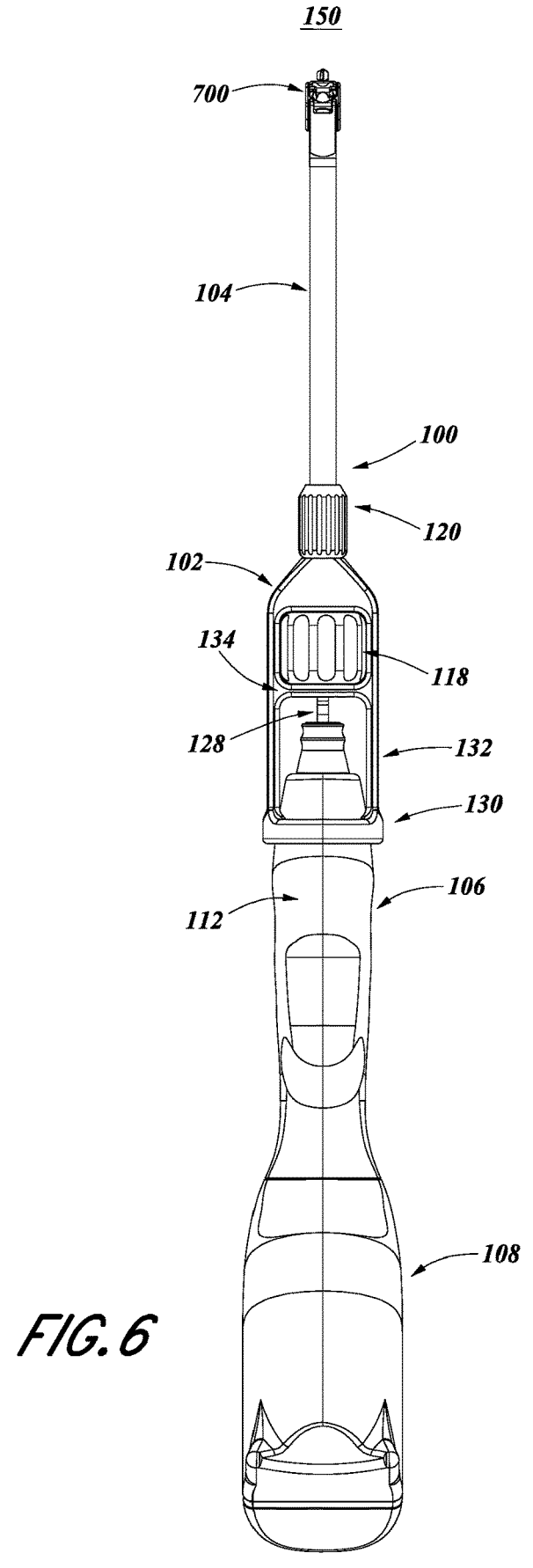

FIGS. 5 and 6 illustrate top and bottom views, respectively, of the fastening system 150. In some embodiments, the articulating tool 100 can be removably connected to the handpiece 106, such as by the body coupling assembly 102. The body coupling assembly 102 being removable may advantageously allow a user to quickly swap between different fastening tools 104 (e.g., from a screwdriver to a hex key, from one length of fastening tool to a different length of fastening tool, etc.) or to quickly replace a damaged fastening tool 104. In several embodiments, the body coupling assembly 102 is slidably engaged with and/or attached to the handpiece 106. For example, the body coupling assembly 102 can be configured to slide on and/or off a distal end of the handpiece 106 along a direction generally parallel to the longitudinal axis L (e.g., z-axis).

In various embodiments, when the body coupling assembly 102 is attached to the handpiece 106, the tool 100 is securely and/or rigidly attached to the handpiece 106. The body coupling assembly 102 may include one or more mating features designed to interlock to the corresponding one or more mating features of the handpiece 106. The mating features may include, for example, complementary grooves, tabs, and/or slots that securely engage with each other. In some embodiments, the body coupling assembly 102 connects to the handpiece 106 with a friction fit. In certain implementations, the body coupling assembly 102 and/or the handpiece 106 may include one or more fastening mechanisms, such as screws, clamps, friction fits, quick-releases, detents, and/or snaps that may be easily engaged or disengaged to facilitate the assembly and disassembly of the articulating tool 100 to the handpiece 106. In some embodiments, the articulating tool 100 may be permanently connected to the handpiece 106.

Figure 7:
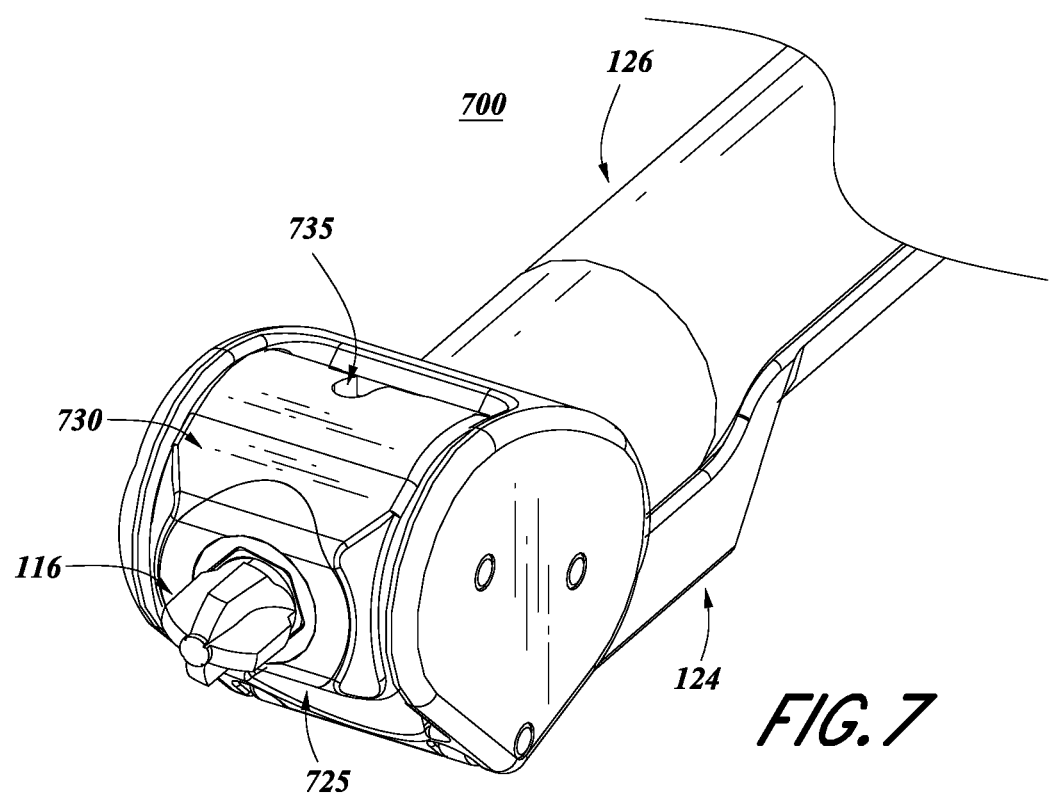
FIGS. 7, 8, and 9 illustrate a perspective, side, and top view, respectively, of a driver head adapter of the fastening system of FIGS. 1 and 2A-2C.
Figure 8:
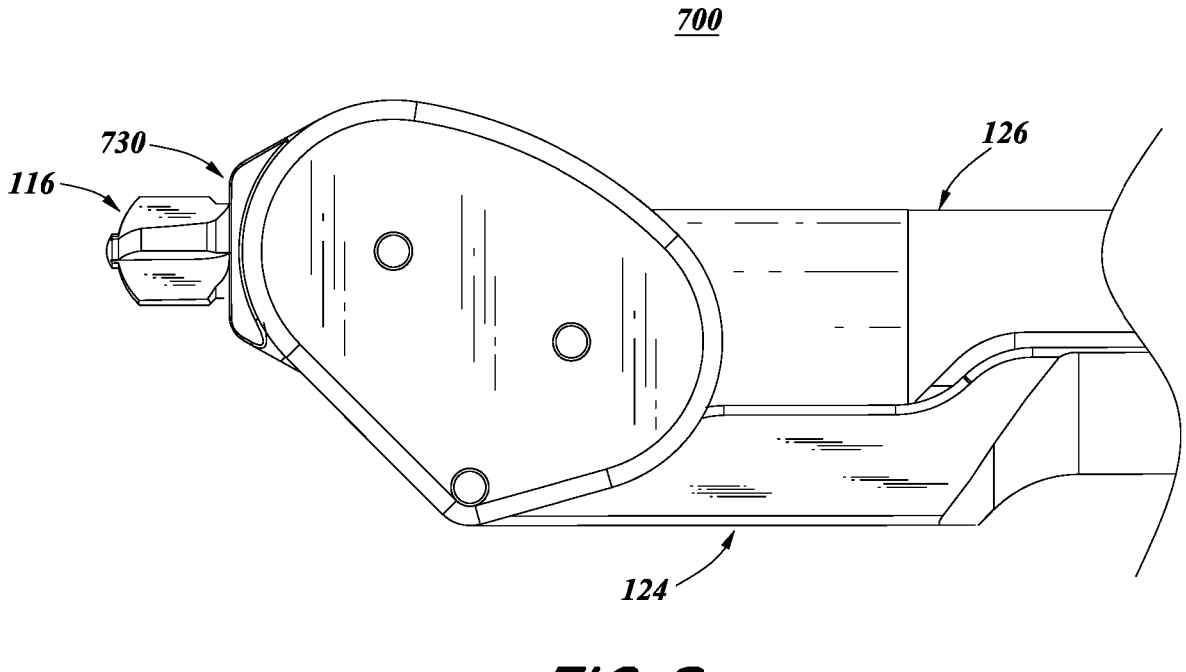
Figure 9:
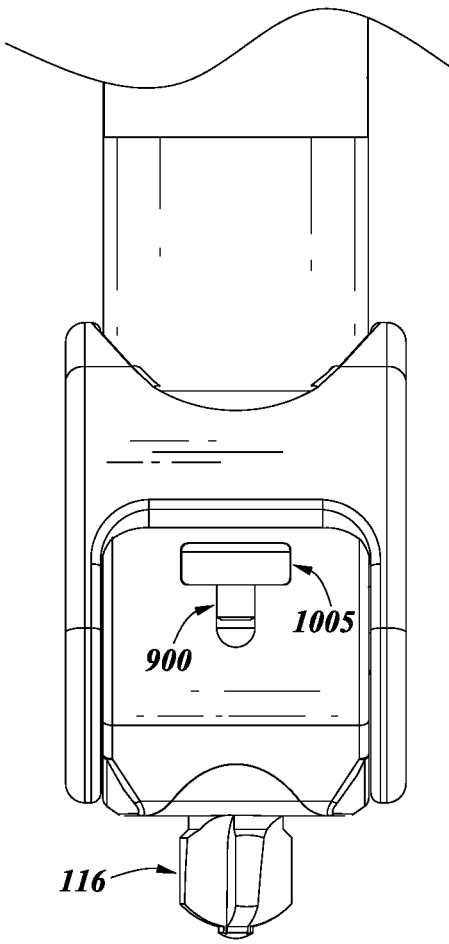

FIGS. 7, 8, and 9 illustrate a perspective, side, and top view, respectively, of an embodiment of the driver head adapter 700 of the articulating tool 100. In some embodiments, the driver head adapter 700 is at the distal end of the fastening tool 104. The driver head adapter 700 can be configured to removably receive a driver head 116 (e.g., a bit or other medical tool). In some implementations, the driver head can matingly engage with a fastener, such as a bone screw, bone fixation pin, surgical anchors, and/or surgical staples. In some implementations, the driver head can mate with a drill bit, bone drill bit, debrider, or other cutting or boring implement. In some positions, such as when the driver head adapter 700 is pointing downward, a longitudinal axis of the driver head 116 can intersect the longitudinal axis L of the articulating tool 100.

In some embodiments, the handpiece 106 can include one or more drive motors (not shown), power supplies 108 (e.g., battery), and/or other features. The one or more drive motors may be electric. In some embodiments, the driver head adapter 700 and driver head 116 can receive torque from the one or more drive motors that are housed within the handpiece 106. For example, the articulating tool 100 may transfer torque from one or more motors to the driver head adapter 700 via an internal shaft 114 (see FIGS. 2B, 2C, and 11) of the fastening tool 104, which can be coupled, directly or indirectly, to an output driveshaft 128 of the motor (see FIG. 2C). In certain embodiments, the shaft 114 is received in a connector unit 136 that couples the shaft 114 and driveshaft 128 for rotation and torque transfer. In some embodiments, the motor is controlled by the one or more operator controls 110. For example, a first button may drive the motor and the driver head 116 clockwise, while a second button drives the motor and driver head 116 counter-clockwise. In certain implementations, there may be one or more buttons that control the speed and/or amount of torque that is transferred from the motor to the driver head 116.

In certain implementations, the driver head 116 is configured to be operated manually. For example, the user may use a control wheel 120 to rotate the driver head 116. In some embodiments, the articulating tool 100 uses a gear system (not shown) to amplify or reduce the torque received at the control wheel 120 before transferring the torque receive from a user to the driver head 116. In some embodiments, the torque received at the control wheel 120 is transferred directly to the driver head 116. In some embodiments, a user may rotate all or a portion of the handpiece 106 to rotate the driver head 116. For example, in some embodiments, a user may rotate the handpiece 106 while holding the body coupling assembly 102 stationary to rotate the driver head 116. It should be understood that the handpiece 106 may take a variety of different shapes and sizes. For example, in some embodiments, the handpiece 106 is cylindrical and tapered at both ends (see handpiece 4100 in FIG. 41). In some variations, the handpiece 106 may have a square, oval, or hexagonal cross section. In some instances, the handpiece 106 does not have a fin 112 or a compartment for a battery or motor. In some embodiments, that torque from any type of driver, motor, or pump may be transferred to the driver head 116 by any of articulating tools and gear systems described herein.

The rotation and/or torque of the wheel 120 may be transferred to the driver head via the internal shaft 114. For example, the control wheel 120 may connect to the internal shaft 114 that rotates one or more gears of a gear assembly 1000 (see FIG. 10). In some embodiments, the gear assembly 1000 may be configured to rotate the driver head 116. The gear assembly 1000 will be discussed in more detail below.

In some embodiments, the driver head adapter 700 may have a front cap 725. The cap 725 can include a rounded front plate 730 and a recess 735. The recess 735 may be configured to receive a protrusion 900 of a stabilizer 1005. The stabilizer 1005 can be configured to securely receive the end of a driver head 116, such as a screwdriver bit. For example, a proximal end of the driver head 116 can abut against the stabilizer 1005. In some implementations, the stabilizer 1005 can aid in positioning the driver head 116 inside the driver head adapter 700 and/or can reduce unwanted movement of the driver head 116. For example, in certain variants the stabilizer 1005 is configured to inhibit or prevent the driver head 116 from shaking or shearing during the operation of the articulating tool 100. This can reduce wear (e.g., on the articulating tool 100, the driver head 116, and/or the operator), enhance secure driving of screws, and/or increase efficiency. In some embodiments, the stabilizer 1005 provides a physical interference (e.g., a stop) through which distally directed force can be applied from the handpiece, through the articulating tool 100 and/or driver head 116, and into the fastener or other surgical implement.

Figure 10A:
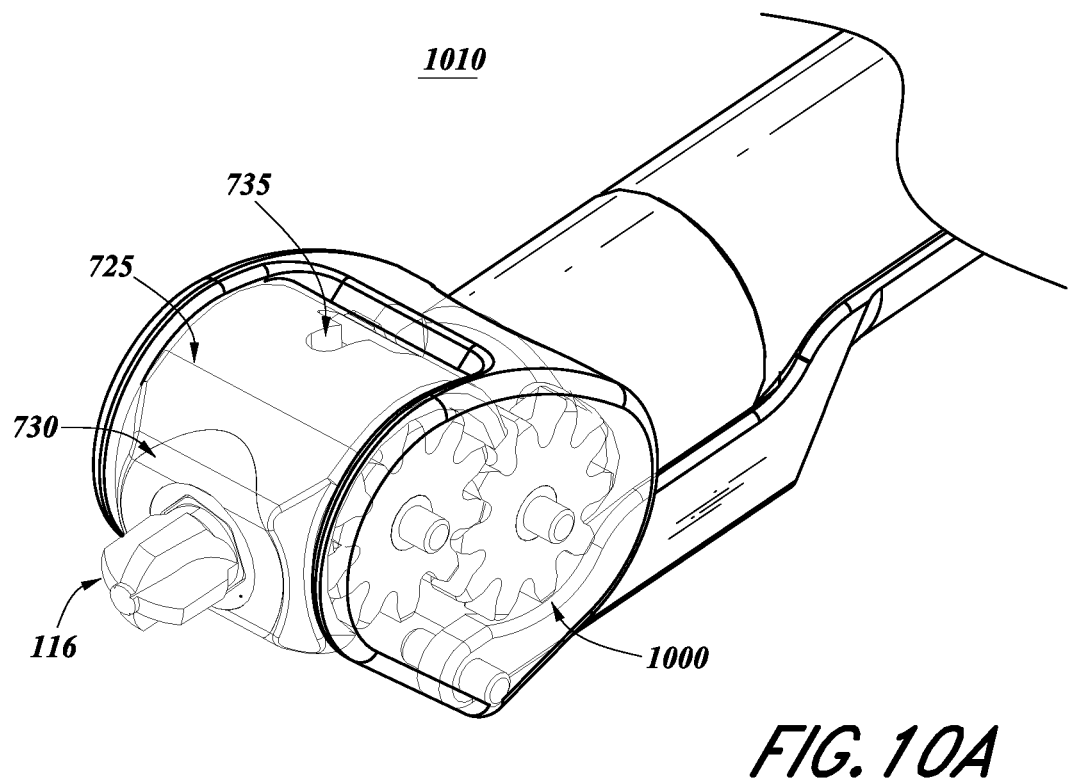
FIG. 10A illustrates a perspective view of the driver head adapter of FIGS. 7, 8, and 9 in a first position and with a cover depicted as transparent to display certain internal components.
Figure 10B:
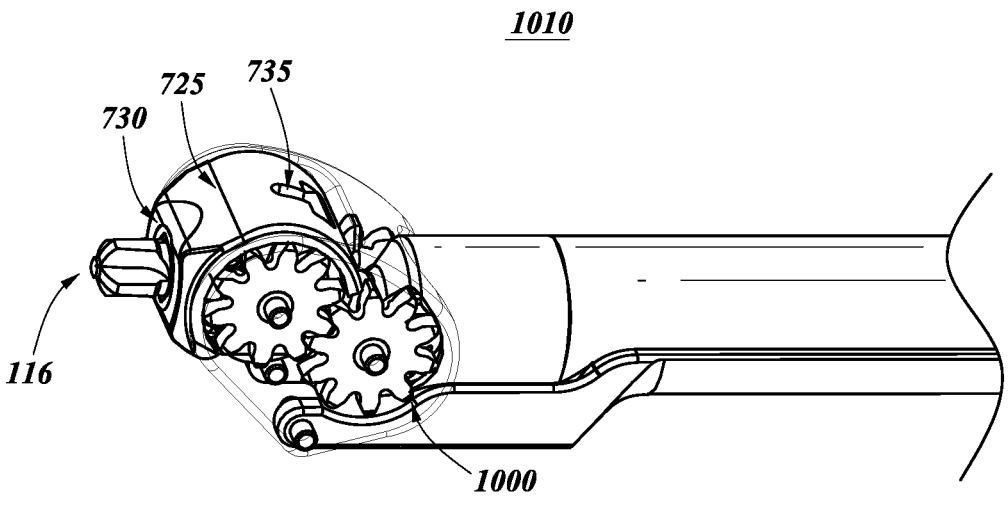
FIGS. 10B and 10C illustrate the driver head adapter of FIG. 10A in a second and third position, respectively, with a cover depicted as transparent to display certain internal components.
Figure 10C:
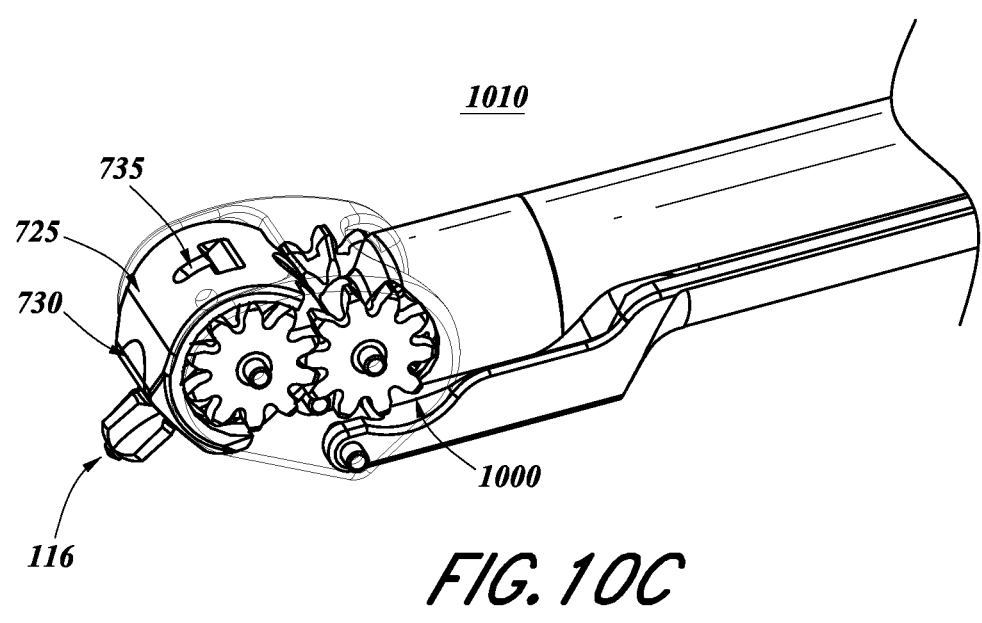

FIGS. 10A-10C illustrate a perspective view of the driver head adapter 700 with a cover depicted as transparent to display certain internal components. As will be discussed in more detail below, the driver head adapter can be articulated, such as between the positions shown in FIGS. 10A-10C. In some embodiments, the internal components of the driver head adapter 700 include a torque transmission unit 1010, as discussed in more detail below. The torque transmission unit 1010 may include components to convey torque from the motor in the handpiece 106 to the driver head 116. In various embodiments, the torque transmission unit 1010 is configured to receive torque from the internal shaft 114, which can be coupled to the motor as previously mentioned. The torque transmission unit 1010 can convey the torque from the internal shaft 114 to the driver head 116. In various embodiments, the torque transmission unit 1010 preserves the direction of the motor. For example, the driver head adapter may rotate the driver head 116 in the same direction as the motor rotates the internal shaft 114.

Figure 11:
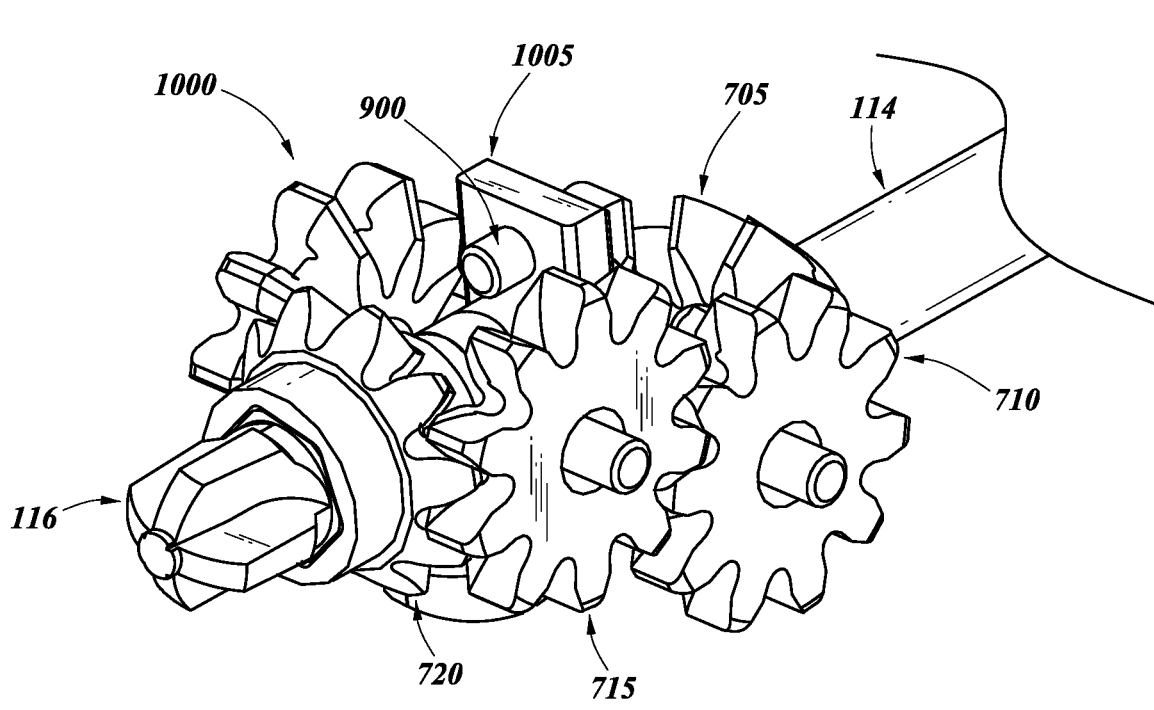
FIGS. 11 and 12 illustrate a perspective view and a side view, respectively, of the internal components of the driver head adapter of FIGS. 10A-10C.
Figure 12:
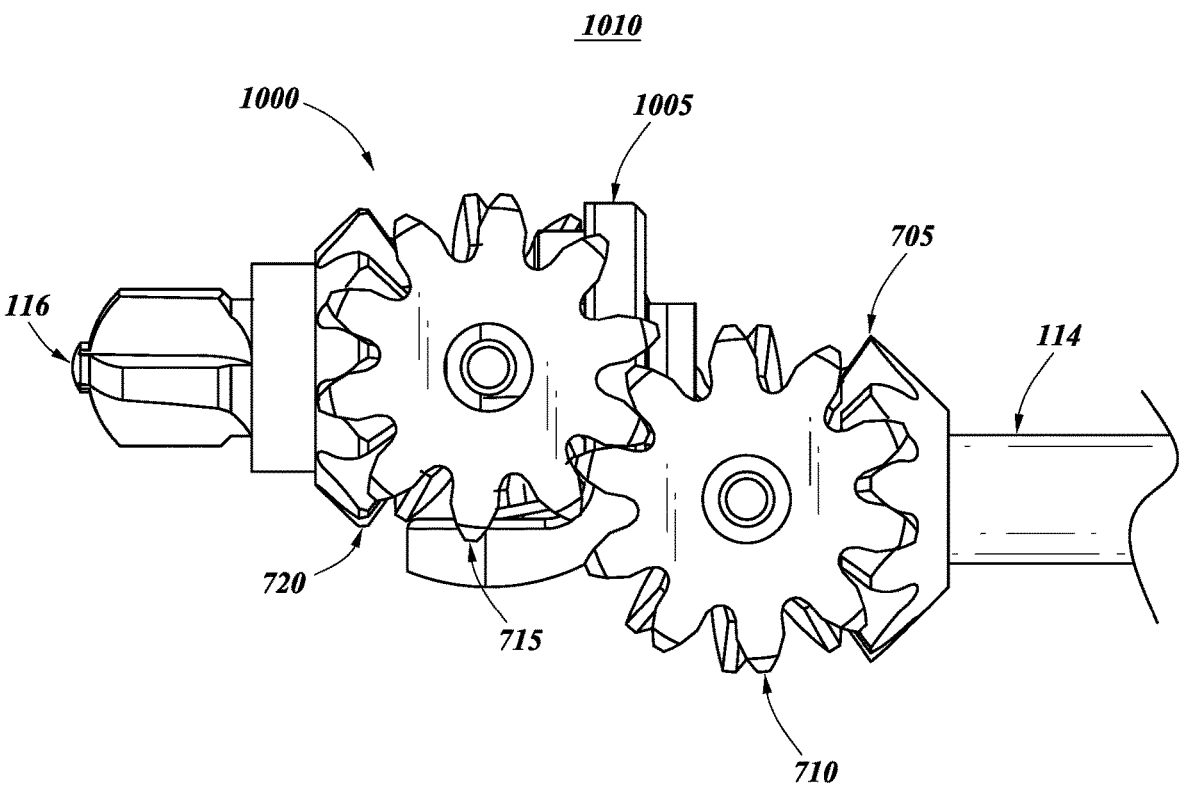

FIGS. 11 and 12 illustrate a perspective view and a side view, respectively, of an embodiment of the internal components of the driver head adapter 700. In some implementations, the torque transmission unit 1010 includes a gear assembly 1000. In some embodiments, the gear assembly 1000 includes a plurality of bevel gears. For example, the gear assembly 1000 can include a first bevel gear 705, one or more second bevel gears 710, one or more third bevel gears 715, and a fourth bevel gear 720. The first bevel gear 705 can be fixedly coupled to the distal end of the internal shaft 114 of the fastening tool 104. Thus, the first bevel gear 705 can receive torque from the drive motor via the internal shaft 114. In some embodiments, the first bevel gear 705 can intermesh with the one or more second bevel gears 710. The one or more second bevel gears 710 can intermesh with the one or more third bevel gears 715. The one or more third bevel gears 715 can intermesh with the fourth bevel gear 720. In some embodiments, the fourth bevel gear 720 can be configured to removably engage with (e.g., receive) the driver head 116, such as is shown in FIG. 16. The fourth bevel gear 720 can be configured to transfer torque to the driver head 116. For example, the fourth bevel gear 720 may have a hexagonal recess 1500 (see FIG. 15) configured to receive a corresponding hexagonal portion 1600 (see FIG. 16) of the shaft of the driver head 116. The flat areas of the hexagonal recess 1500 may inhibit or prevent the driver head 116 from rotating independently of the fourth bevel gear 720. The recess of the fourth bevel gear 720 may be a recess of any shape configured to inhibit or prevent the driver head 116 from rotating independently of the fourth bevel gear 720. Any type of gears (e.g., spur gears, helical gears, worm gears, internal gears, etc.) may be used for any of the gear assemblies described herein.

Figure 13:
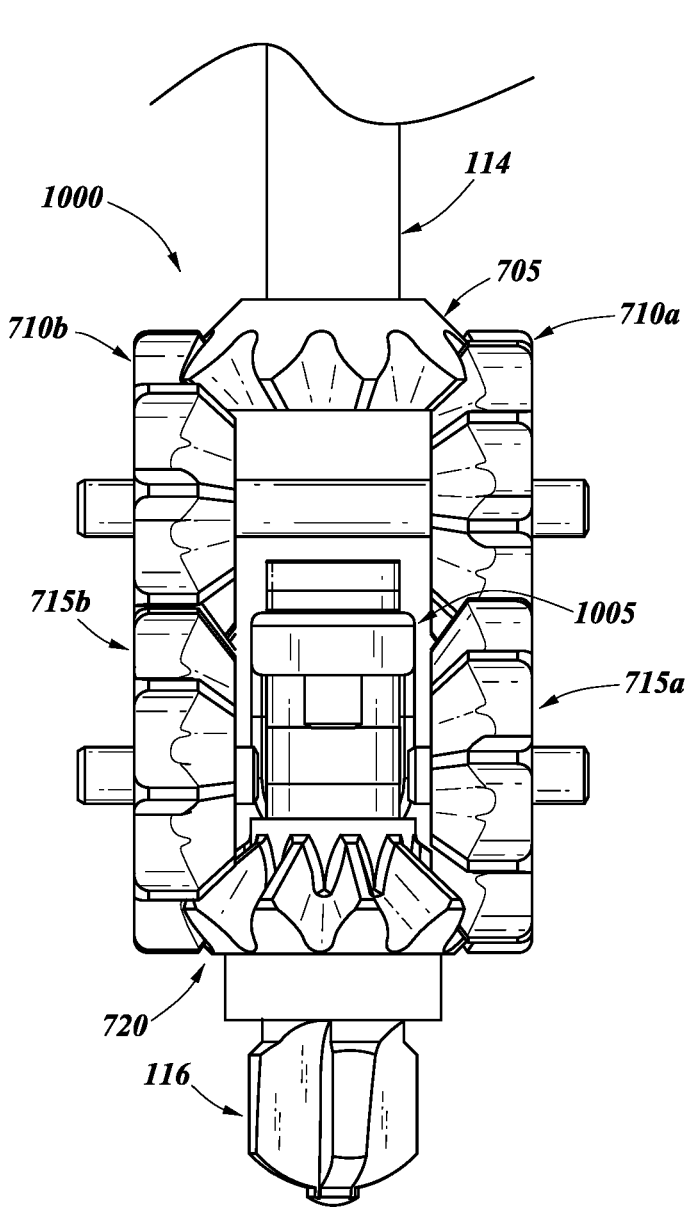
FIGS. 13 and 14 illustrate a top and bottom view, respectively, of the internal components of the driver head adapter of FIGS. 10A-10C.
Figure 14:
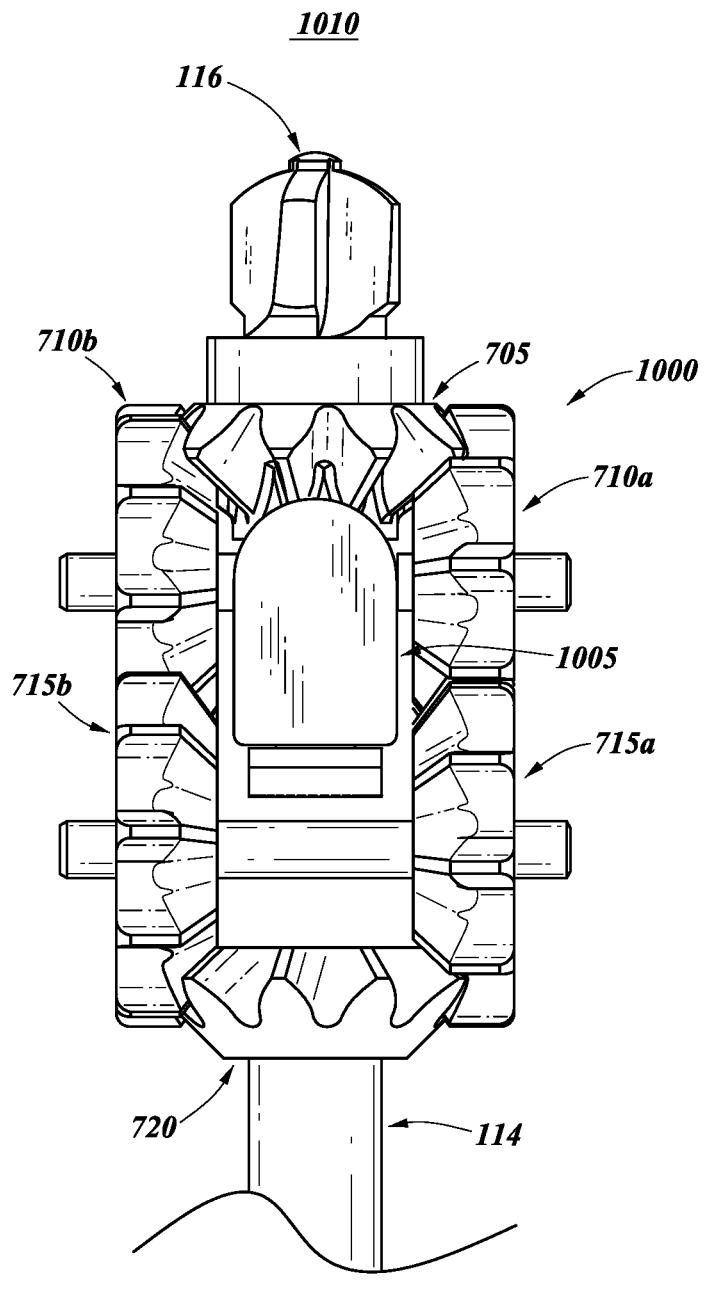

FIGS. 13 and 14 illustrate a top and bottom view, respectively, of internal components of the driver head adapter 700. Advantageously, in implementations with multiple second bevel gears 710 and/or multiple third bevel gears 715, the gear assembly 1000 divides the motor torque between the left and right sides of the gear assembly 1000, while also facilitating articulation (as discussed below). More specifically, the first bevel gear 705 transfers approximately half of the motor torque to the right second gear 710A, and approximately half of the motor torque to the left second gear 710B. In certain implementations, the motor torque is divided between the individual gears of the set of third bevel gears 715A, 715B. The fourth gear receives half of the motor torque from the third right gear 715A and half of the motor torque from the third left gear 715B. Thus, the fourth gear receives approximately the full motor torque (e.g., approximately half from each side of the gear assembly 1000). Dividing the motor torque between the two sides of the gear assembly 1000 reduces the force experienced by the second set 710A, 710B and third set 715A, 715B of bevel gears. Dividing the torque can, for example, allow the gear assembly 1000 to safely, reliably, and/or efficiently transfer high torque loads. In some implementations, dividing the motor torque between the two sides of the gear assembly 1000 can reduce cost and/or size by allowing smaller and/or less strong bevel gears to be used for at least the second set 710A, 710B and third set 715A, 715B of bevel gears.

Figure 15:
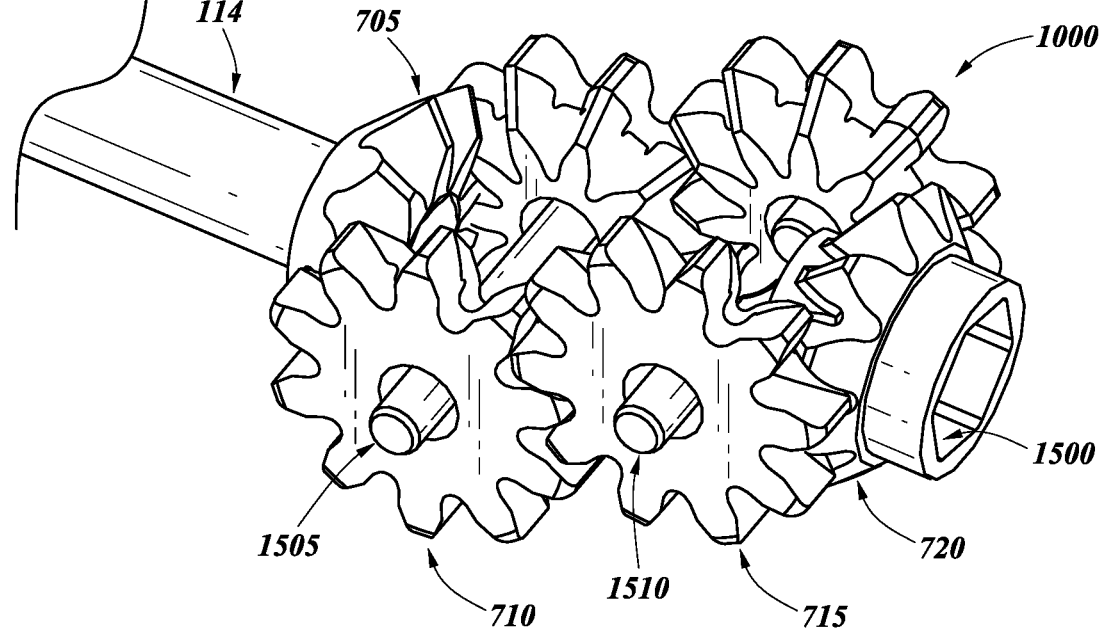
FIG. 15 illustrates a perspective view of the internal components of the driver head adapter of FIGS. 10A-10C with a driver head not installed.
Figure 16:
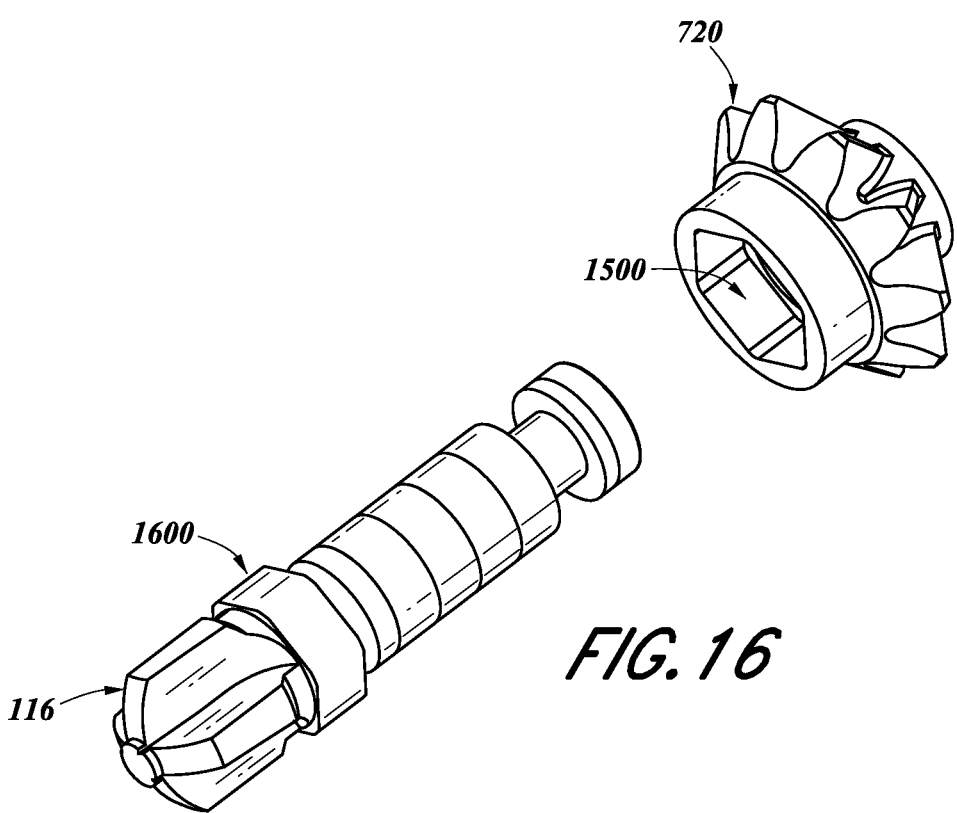
FIG. 16 illustrates a perspective view of a driver head detached from a portion of (e.g., a hexagonal recess of a fourth bevel gear) of the driver head adapter of FIGS. 10A-10C.

FIG. 15 illustrates a perspective view of internal components of the driver head adapter 700 with no outer casing or driver head. As described above, the hexagonal recess 1500 is configured to securely and removably connect and transfer torque to the driver head 116. The removable driver head 116 allows a user to quickly change between different driver heads 116. For example, a user may want to switch to a different type of driver head 116 or replace a broken or worn driver head.

In some embodiments, the torque transmission unit 1010 is configured to articulate when the driver head adapter 700 moves. For example, the torque transmission unit 1010 can be configured to rotate about the x-axis (the transverse axis of the fastening tool 104). In some embodiments, the second set of bevel gears 710 is on a first pin or set of pins 1505 and the third set of bevel gears 715 is on a second pin or set of pins 1510. For example, as shown in FIG. 15, a pin 1505 can extend between and connect the second set of bevel gears 710 and each of the third set of bevel gears 715 can have a separate pin 1510. The pins or sets of pins 1505, 1510 may be attached to the shell of the driver head adapter 700 and cause the third set of bevel gears 715 to rotate about the first guiding pin 1505 when the driver head adapter 700 is tilted.

Thus, the torque transmission unit 1010 can transfer torque from the motor to the driver head 116 while the driver head adapter 700 is tilted.

FIG. 16 illustrates a perspective view of a detached driver head 116 from the hexagonal recess 1500 of the fourth bevel gear 720. As described above, the driver head 116 have a corresponding hexagonal portion 1600. The articulating tool 100 may be used for various types of operations, such as ablations, imaging, and biopsies. Thus, in some embodiments, the driver head 116 may be an electrode or ablation device, a specialized imaging probe, a cutting tool, grasper, or any other type of surgical tool.

Figure 17:
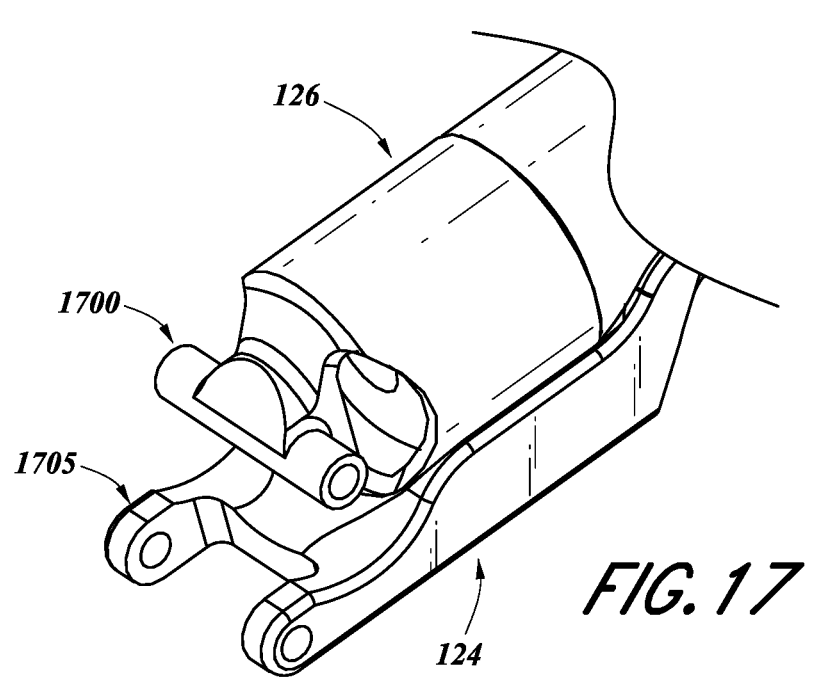
FIG. 17 illustrates a distal end of a multi-part shaft of the fastening system of FIGS. 1 and 2A-2C.

FIG. 17 illustrates the distal end of the multi-part shaft 122 of the fastening tool 104. In some embodiments, the fastening tool 104 has an upper anchor point 1700 and a lower anchor point 1705 for the driver head adapter 700. The two anchor points 1700, 1705 allow the driver head adapter 700 to rotate about the x-axis as described above. Overall, the fastening system 150 allows a user to accurately and efficiently treat patients undergoing surgical procedures by providing greater control, reliability, and durability.

Articulating Tool with Turret Driver Head Adapter (FIGS. 18-29)

Figure 18:
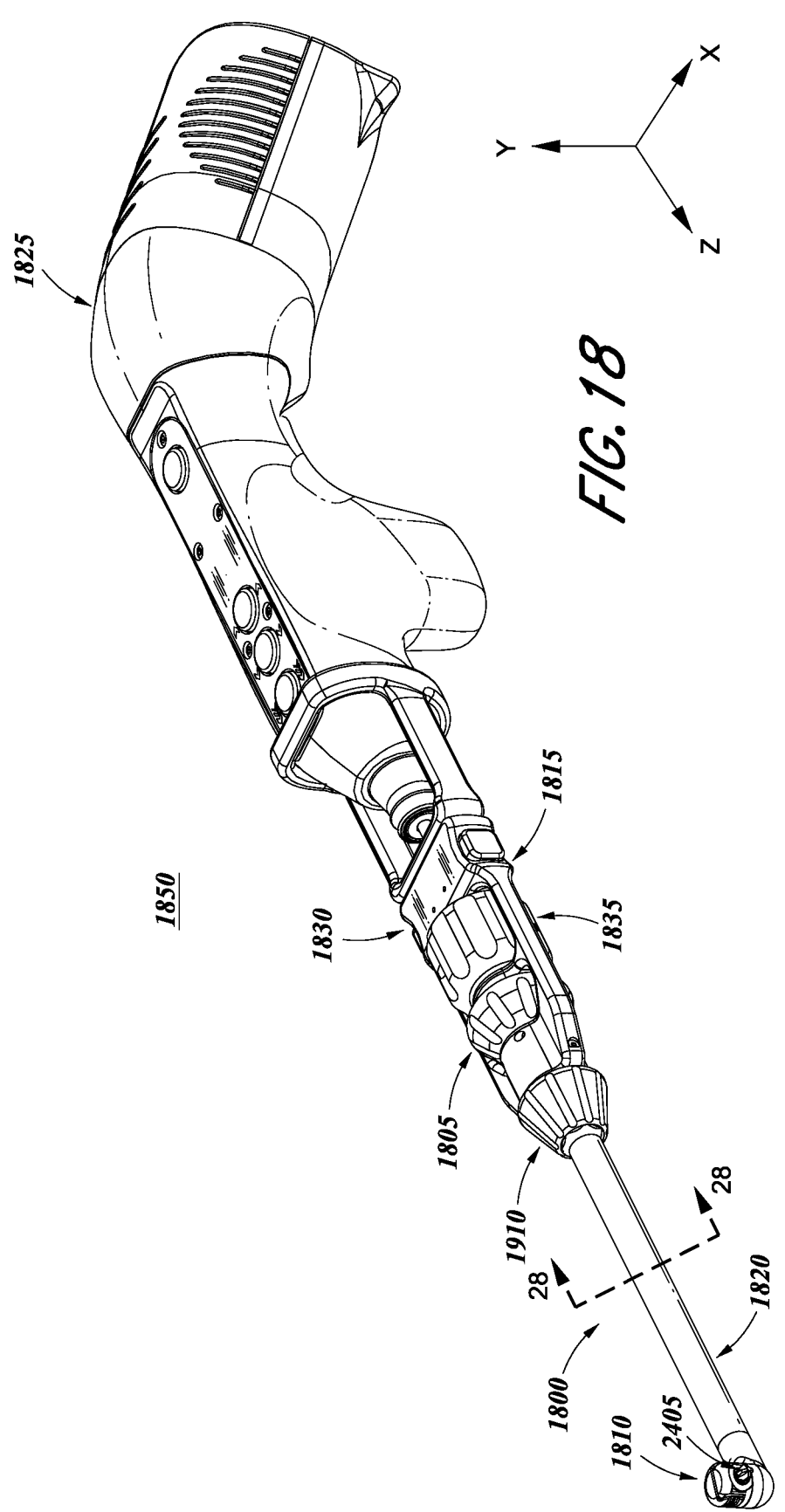
FIG. 18 illustrates an embodiment of a fastening system that includes an articulating tool with a turret driver head adapter and a handpiece.

FIG. 18 illustrates an embodiment of a fastening system 1850 that includes an articulating tool 1800 with a turret driver head adapter 1810 and a handpiece 1825. The articulating tool 1800 can include a body coupling assembly 1815 and a fastening tool 1820. The body coupling assembly 1815 may connect to a handpiece coupling assembly 1840, such as with a quick-release mechanism 1830. The handpiece coupling assembly 1840 can be rigidly and/or securely connected to the handpiece 1825. In some embodiments, the handpiece coupling assembly 1840 can be removably connected to the handpiece 1825 via a quick-release mechanism (not shown) or any other fastening mechanism described herein. These features will be described in more detail below. The articulating tool 1800 may include any of the features of the articulating tool 100, and vice versa.

The articulating tool 1800 may include one or more controls (e.g., the control wheel 1805, 1835, 1910) to articulate the turret driver head adapter 1810 and/or driver head 2405. The one or more control wheels 1805, 1835, 1910 may be digital and/or analog and may be the same or different sizes. For example, in some implementations, the diameter of the first control wheel 1835 may be 25 mm, and the diameter of the second control wheel 1805 may be 20 mm, and the diameter of the third wheel 1910 may be 15 mm. The diameter of the wheels may vary to accommodate different needs and user preferences. For instance, one or more of the wheels 1805, 1835, 1910 may have a diameter of 1 mm, 5 mm, 10 mm, 15 mm, 40 mm, more than 40 mm, or any diameter in-between. In some embodiments, the one or more control wheels 1805, 1835, 1910 may be positioned coaxially along the z-axis. For instance, the first control wheel 1835 may be positioned in the middle of the body coupling assembly 1815, the second control wheel 1805 may be position more towards the front (e.g., distal end) of the body coupling assembly 1815, and the third control wheel 1910 may be positioned on the distal end of the body coupling assembly 1815. In some embodiments, one or more control wheels 1805, 1835, 1910 may be positioned on the handpiece 1825 or the articulating tool 1800. In some instances, the one or more control wheels 1805, 1835, 1910 may be on two or more different axes (e.g., a first z-axis and a second z-axis that is offset from the first z-axis).

For example, as discussed in more detail below, the control wheels 1805, 1835, 1910 can be configured to rotate the turret driver head adapter 1810 in multiple axes and/or provide multiple degrees of freedom (e.g., three or more axes and/or degrees of freedom). In some embodiments, the first control wheel 1835 controls the rotation of the driver head 2405, the second control wheel 1805 controls the rotation of the turret driver head adapter 1810 about the y-axis, and the third control wheel 1910 controls the rotation of the articulating tool 1800 about the z-axis. In some embodiments, a longitudinal axis of the driver head 116 does not intersect (e.g., in all positions of the driver head) a longitudinal axis of the articulating tool 1800. For example, in certain variants, the longitudinal axis of the driver head 116 can swing to define a plane that does not intersect the longitudinal axis of the articulating tool 1800.

Figure 19:
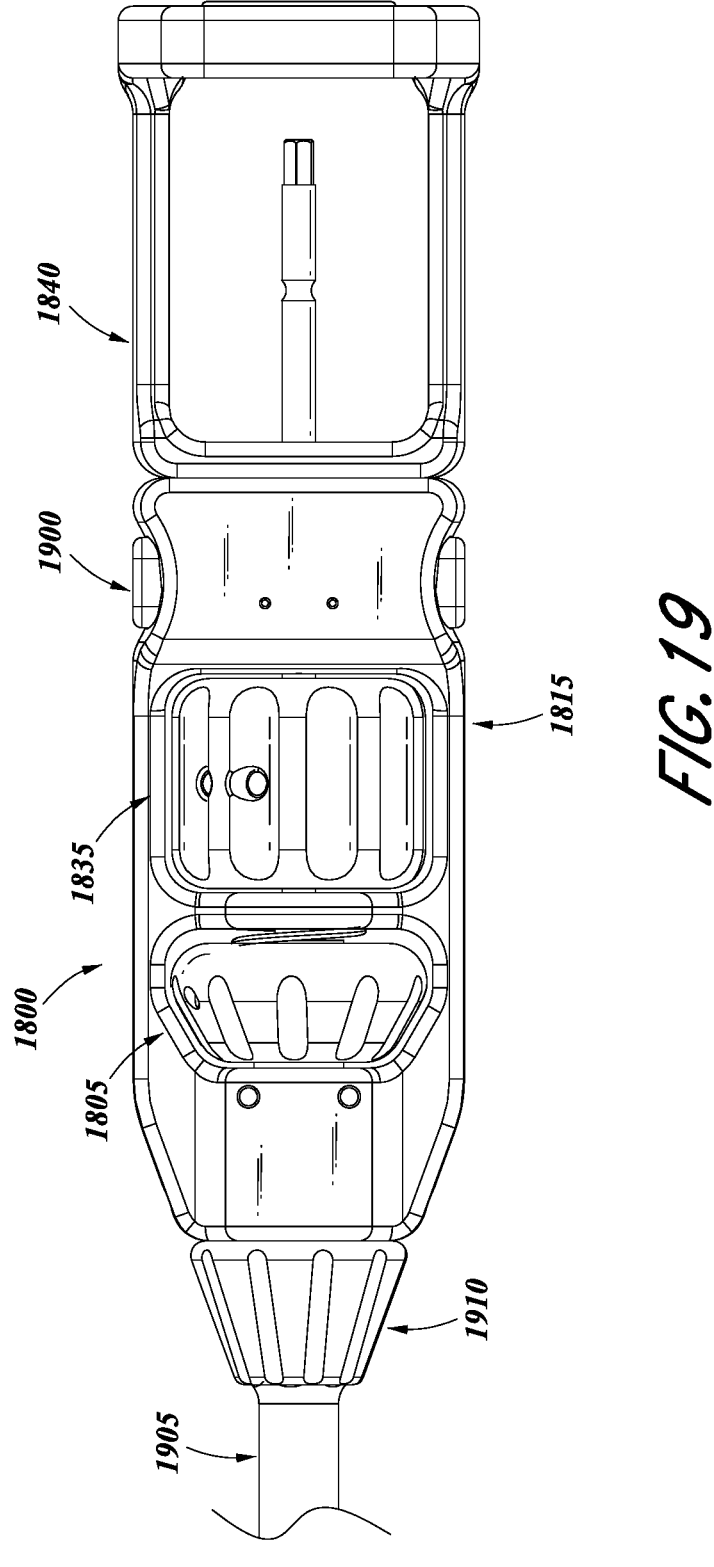
FIG. 19 illustrates a top view of a body coupling assembly of the fastening system of FIG. 18.
Figure 20:
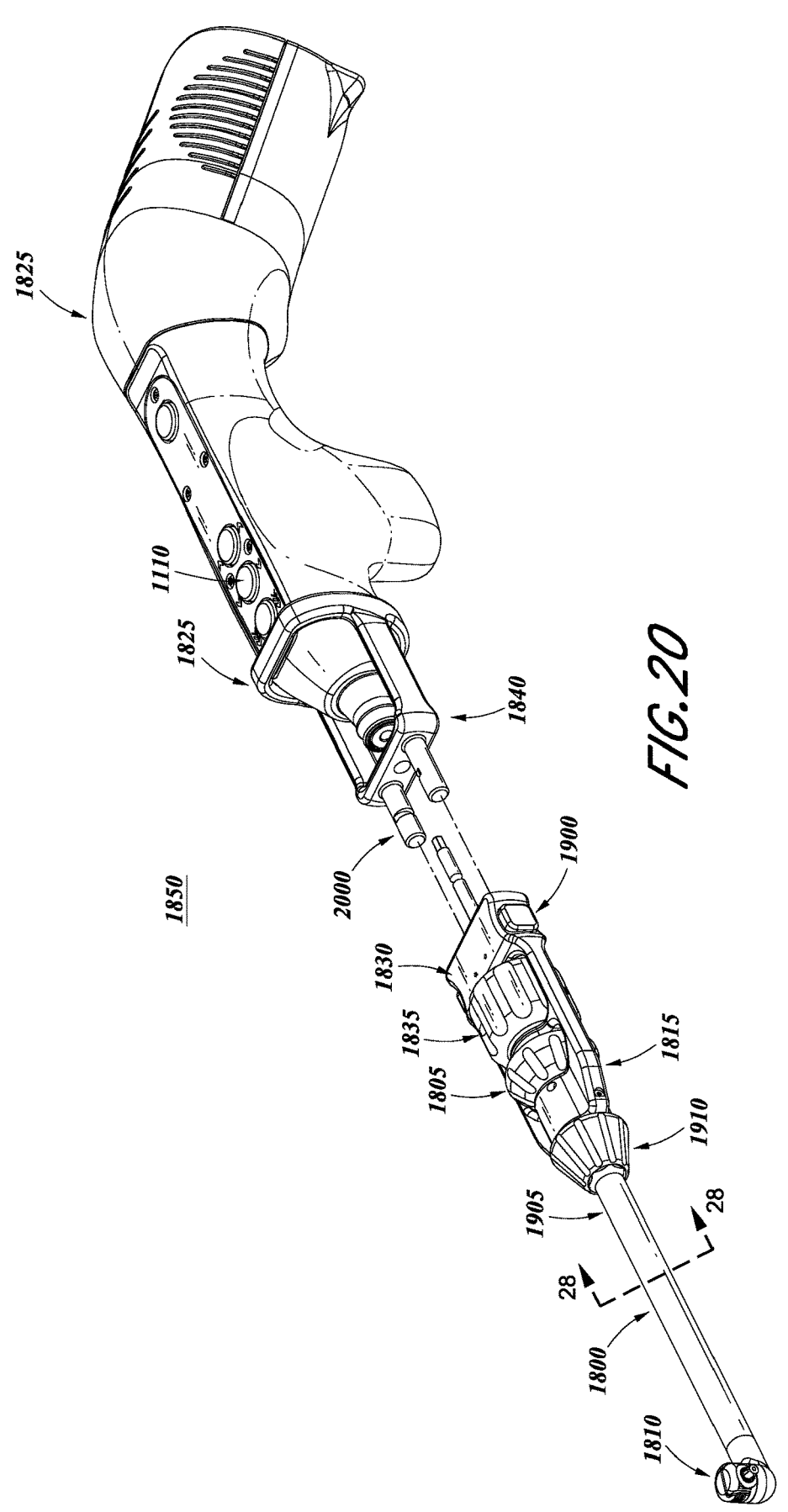
FIG. 20 illustrates a perspective view of the fastening system of FIG. 18 in which the body coupling assembly is detached from the handpiece.
Figure 21:
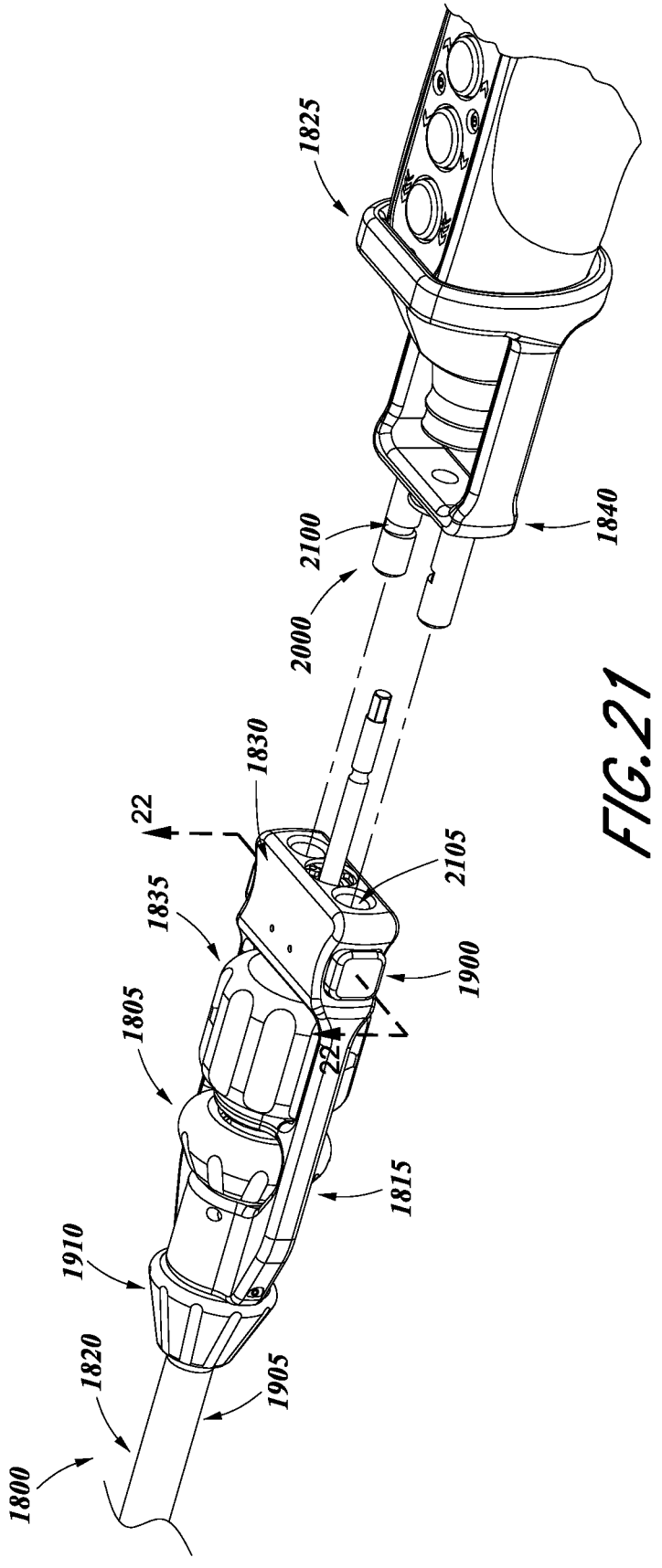
FIG. 21 illustrates a back perspective view of the fastening system of FIG. 18 in which the body coupling assembly is detached from the handpiece.

FIG. 19 illustrates a top view of the body coupling assembly 1815. FIG. 20 illustrates a perspective view of the body coupling assembly 1815 detached from the handpiece coupling assembly 1840 and the handpiece 1825. Additionally, FIG. 21 illustrates a back perspective view of the body coupling assembly 1815 detached from the handpiece coupling assembly 1840 and the handpiece 1825. As shown, in some embodiments, the body coupling assembly 1815 is removably connected via a quick-release mechanism 1830 to the handpiece coupling assembly 1840 (which can be connected to the handpiece 1825).

In certain implementations, the quick-release mechanism 1830 may be operated by one or more buttons 1900 (e.g., two buttons). For example, the one or more buttons 1900 may disengage a lock and allow a user to detach the body coupling assembly 1815. As illustrated, in some embodiments, the body coupling assembly 1815 is disconnected by sliding the body coupling assembly 1815 off one or more guiding pins 2000 of the handpiece coupling assembly 1840 or the handpiece 1825.

In certain implementations, the body coupling assembly 1815 may use any of the coupling methods described in any embodiments described herein. In some embodiments, the buttons 1900 are on opposite sides of the body coupling assembly 1815 and/or are depressed toward a longitudinal axis of the body coupling assembly 1815. In some variants, the quick-release mechanism 1830 comprises one or more detents, latches, bayonet connections, friction fits, or other connection mechanisms. For example, in some implementations, the body coupling assembly 1815 may have spring-loaded connections that automatically push pins into notches 2100 when the posts of the handpiece coupling assembly 1840 are pushed into the mating holes 2105 of the body coupling assembly 1815. In some embodiments, the pins are pushed out of the notches 2100 when the one or more buttons 1900 are depressed. The one or more buttons 1900 may be spring-loaded so that they automatically returned to the locked/un-depressed position. The spring 2225 (see FIG. 22) may reside between the one or more buttons 1900. In some embodiments, the one or more buttons 1900 have one or more guiding pins 2215 and corresponding slots 2220. The one or more guiding pins 2215 facilitate linear movement and ensure that the buttons 1900 efficiently lock and unlock the connection between the body coupling assembly 1815 and the handpiece coupling assembly 1840. Advantageously, the quick-release mechanism 1830 facilitates a secure removable connection between the body coupling assembly 1815 and the handpiece coupling assembly 1840.

Figure 22:
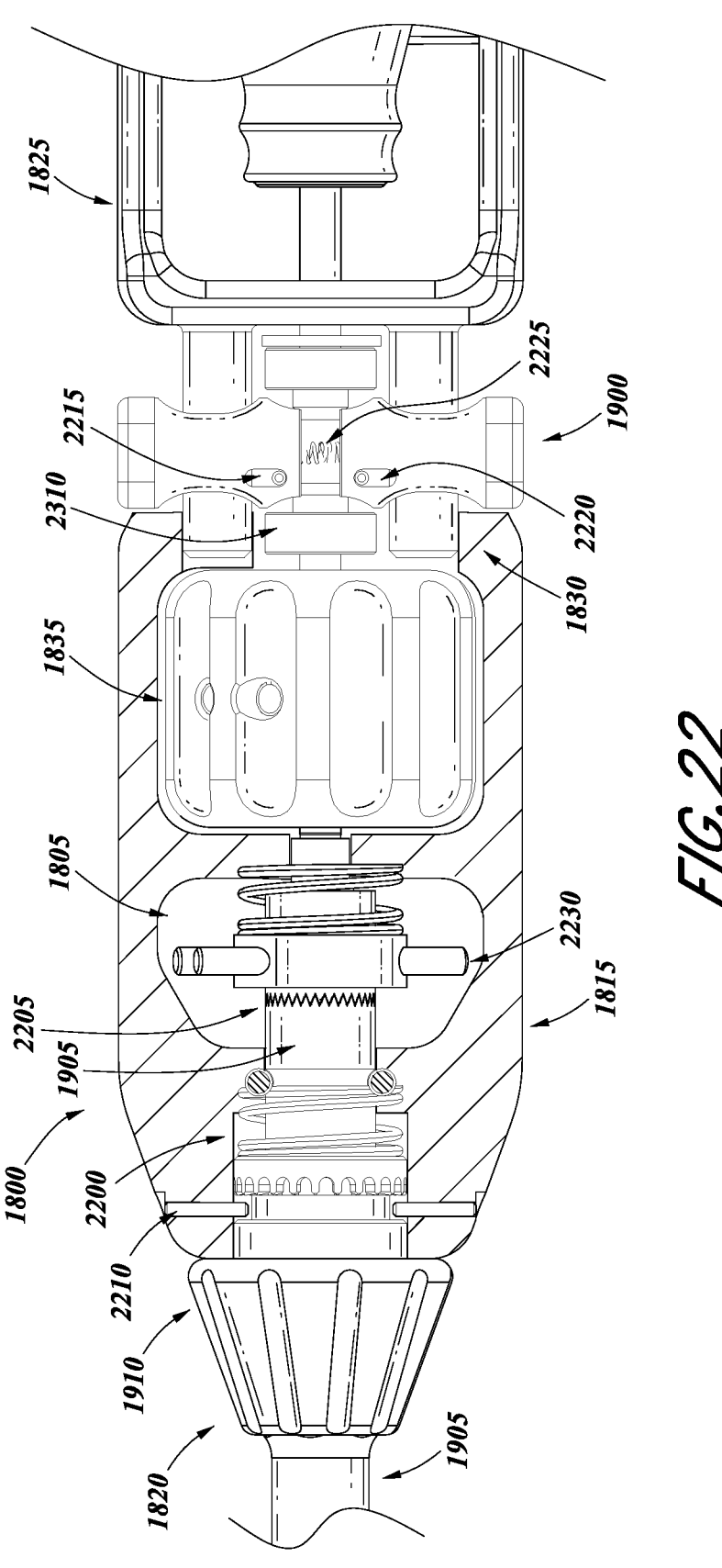
FIG. 22 illustrates a top partial-cross-section view of the body coupling assembly attached to the handpiece of the fastening system of FIG. 18.

FIG. 22 illustrates a top partial-cross-section view of the body coupling assembly 1815 attached to the handpiece 1825. More specifically, FIG. 22 illustrates a cross-section of the main housing of the body coupling assembly 1815 with the outer casing of the control wheel 1805 removed. In some embodiments, the fastening tool 1820 and/or turret driver head adapter 1810 can swivel, articulate, move, rotate, and/or reposition relative to the handpiece 1825 and/or the body coupling assembly 1815. For example, an elongate outer housing 1905 of the fastening tool 1820 can rotate about the z-axis (e.g., a longitudinal axis of the fastening tool 1820). Thus, a user can rotate the elongate outer housing 1905 without rotating the body coupling assembly 1815 or the handpiece 1825, or vice versa. In some embodiments, rotating the elongate outer housing 1905 also rotates the driver head adapter 1810 about the z-axis. The body coupling assembly 1815 may include one or more controls for rotating the elongate outer housing 1905. For example, the body coupling assembly 1815 may include a control wheel 1910 that is fixed to the elongate outer housing 1905. Thus, a user can rotate the elongate outer housing 1905 by rotating the control wheel 1910.

In some embodiments, the control wheel 1910 has a locking clutch 2200. The locking clutch 2200 can lock the rotation of the elongate outer housing 1905 relative to the body coupling assembly 1815. As illustrated, the locking clutch 2200 can comprise interfacing (e.g., interlocking) mating teeth that mate with one or more locking pins 2210 (e.g., two locking pins) when locked. The locking clutch 2200 may be spring-loaded or biased by a biasing member. In some embodiments, a user can disengage the locking clutch 2200 by sliding the locking clutch 2200 (e.g., along the z-axis) into a disengaged position (e.g., the spring of the locking clutch 2200 is compressed and/or the mating teeth are disengaged as shown in FIG. 22). The spring for the locking clutch 2200 may reside in a recess of the body coupling assembly 1815 and be coaxial with the elongate outer housing 1905. In some embodiments, when the locking clutch is in the disengaged position, the user can rotate the control wheel 1910, which rotates the elongate outer housing 1905. In some embodiments, the locking clutch 2200 can lock into predetermined positions. For example, the locking clutch 2200 may have a locking position every 1°, 5°, 10°, 30°, 90°, or more than 90°, or any number in between. In certain implementations, the locking clutch 2200 may be able to lock into any position.

Figure 23:
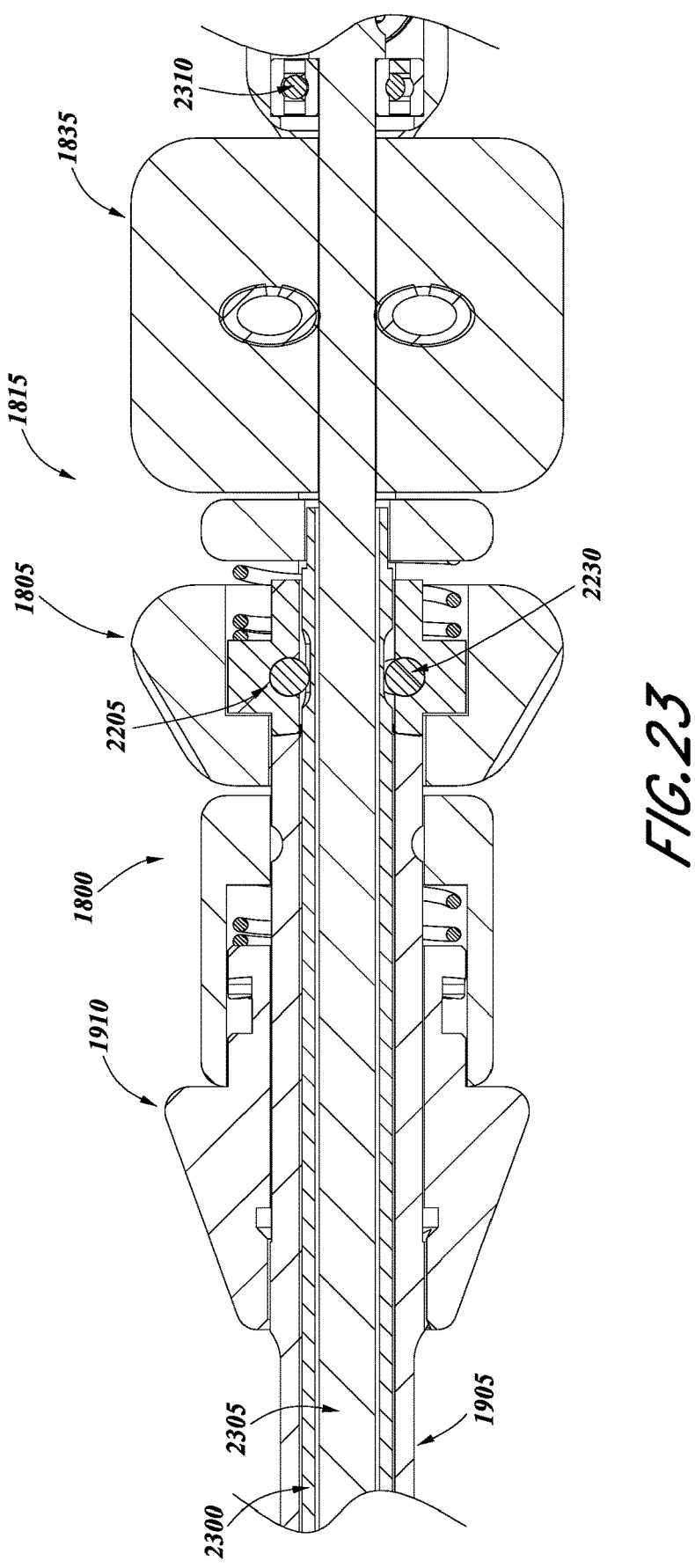
FIG. 23 illustrates a side cross-section view of the body coupling assembly of the fastening system of FIG. 18.

FIG. 23 illustrates a side cross-section view of the body coupling assembly 1815. In some embodiments, the turret driver head adapter 1810 can rotate about the y-axis. The body coupling assembly 1815 may have an orientation control mechanism, such as the control wheel 1805, a lever, an arm, or an electronic mechanism. In some embodiments, the orientation control mechanism is configured to rotate the turret driver head adapter 1810 about the y-axis. For example, the control wheel 1805 may connect to an internal shaft 2300 (also called a first internal shaft) that rotates one or more gears of a gear assembly 2500 (see FIG. 25). In some embodiments, the gear assembly 2500 may be configured to rotate the turret driver head adapter 1810. The gear assembly 2500 will be discussed in more detail below. In some embodiments, the internal shaft 2300 is between the elongate outer housing 1905 and a second internal shaft 2305, which is discussed in more detail below. The elongate outer housing 1905, the internal shaft 2300, and the second internal shaft 2305 may be concentric shafts. In some embodiments, the fastening tool 1820 has multiple lumens within the elongate outer housing 1905. Thus, the internal shaft 2300 and the second internal shaft 2305 may not be concentric.

In some embodiments, the control wheel 1805 for the turret driver head adapter 1810 may have a locking clutch 2205 (see FIG. 22). As illustrated, the locking clutch 2205 can comprise interfacing (e.g., interlocking) mating teeth that mate with the elongate outer housing 1905. The locking clutch 2205 can lock the rotation of the turret driver head adapter 1810 relative to the protective bottom housing 2400 (see FIG. 24). The locking clutch 2205 may be spring-loaded or biased by a biasing member. The spring for the locking clutch 2205 may reside in a circular recess of the body coupling assembly 1815 and be coaxial with the internal shaft 2300. In some embodiments, a user can disengage the locking clutch 2205 by sliding the locking clutch 2200 (e.g., along the z-axis) into a disengaged position (e.g., the spring of the locking clutch 2205 is compressed and/or the mating teeth are disengaged). In some embodiments, when the locking clutch is in the disengaged position, the user can rotate the control wheel 1805 which rotates the internal shaft 2300. The control wheel 1805 may use one or more pins 2230 to connect to corresponding grooves on the internal shaft 2300. In some embodiments, the locking clutch 2205 can lock into predetermined positions. For example, the locking clutch 2205 may have a locking position every 1°, 5°, 10°, 30°, 90°, or more than 90°, or any number in between. In certain implementations, the locking clutch 2205 may be able to lock into any position. In some embodiments, the body coupling assembly 1815 may have one or more bearings 2310 to reduce or remove the friction between two or more components (e.g., a rotating shaft and a non-rotating body).

The body coupling assembly 1815 may have a control to operate the driver head 2405 manually. The control may be a control wheel 1835 that transfers torque receive from a user to the driver head (e.g., the bit). The rotation and/or torque of the wheel 1835 may be transferred to the driver head via the internal shaft 2305. In some embodiments, the articulating tool 1800 uses a gear system (not shown) to amplify or reduce the torque received at the control wheel 1835 before transferring the torque receive from a user to the driver head 2405. In some embodiments, the torque received at the control wheel 1835 is transferred directly to the driver head 2405. For example, the control wheel 1835 may connect to the internal shaft 2305 that rotates one or more gears of a gear assembly 2505 (see FIG. 25). In some embodiments, the gear assembly 2505 may be configured to rotate the driver head 2405. The gear assembly 2505 will be discussed in more detail below.

Figure 24:
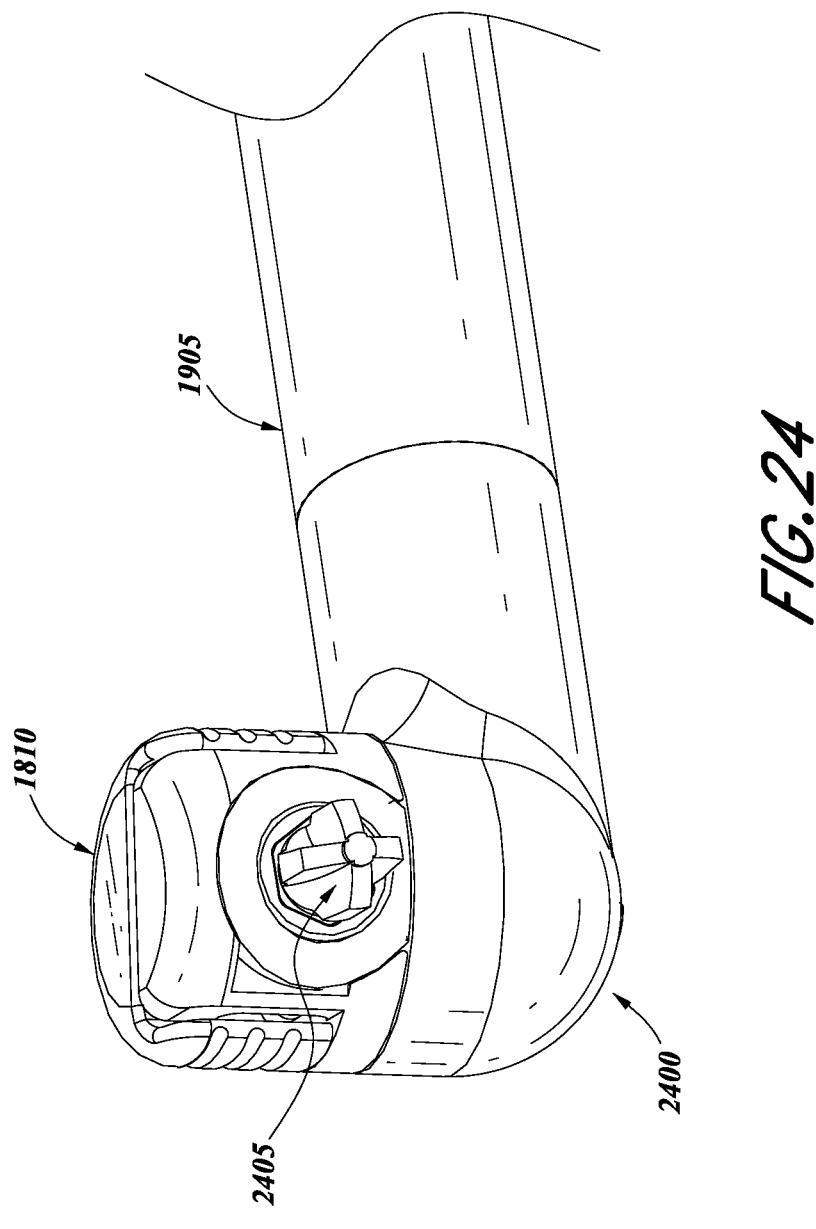
FIG. 24 illustrates a close-up view of the turret driver head adapter of the fastening system of FIG. 18.

FIG. 24 illustrates a close-up view of the turret driver head adapter 1810. In some embodiments, the turret driver head adapter 1810 is offset from the z-axis (e.g., the longitudinal axis of the fastening tool 1820) and/or rotates about the y-axis (e.g., the transverse axis). In some embodiments, the turret driver head adapter 1810 can rotate 0°-360° about the y-axis. In some embodiments, the turret driver head adapter 1810 can rotate freely about the y-axis (e.g., can do multiple complete rotations). In various embodiments, the turret driver head adapter 1810 includes the driver head 2405. The driver head 2405 can be offset (e.g., spaced apart) from the longitudinal axis of the tool 1800 and/or the elongate outer housing 1905. For example, the longitudinal axis of the driver head 2405 and the longitudinal axis of the tool 100 may be non-coplanar on the z-x plane.

Figure 25:
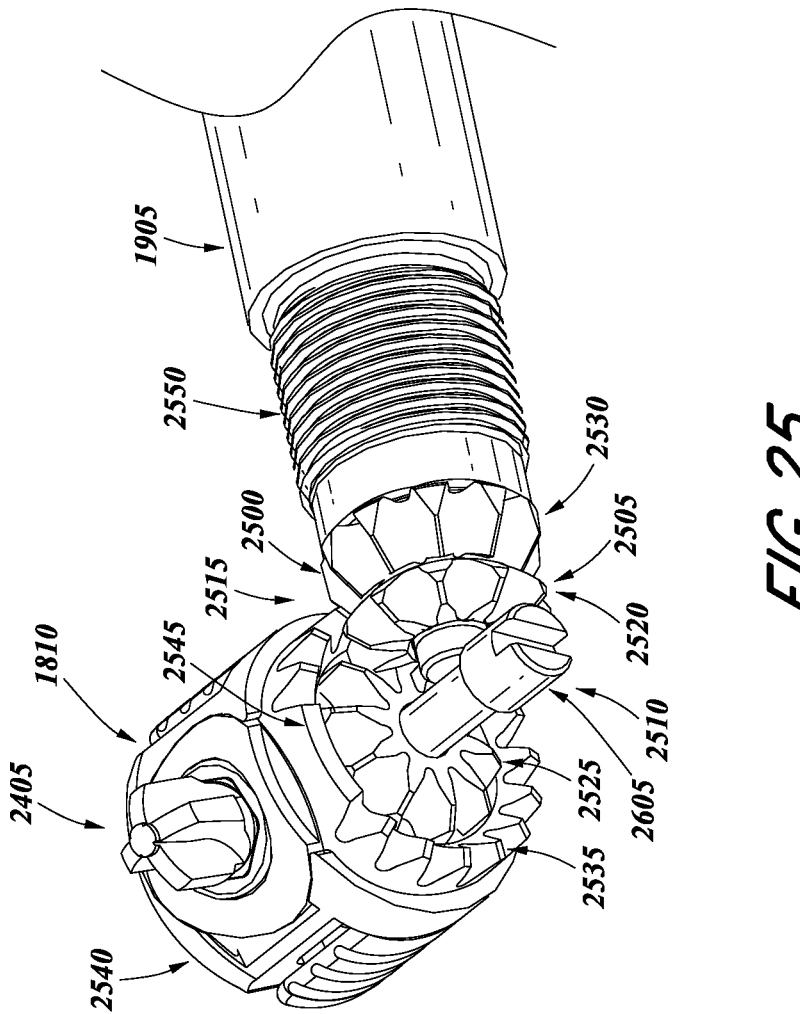
FIGS. 25 and 26 illustrate close-up views of certain internal components of the turret driver head adapter of FIG. 24, with certain cover components not shown for purposes of presentation.
Figure 26:
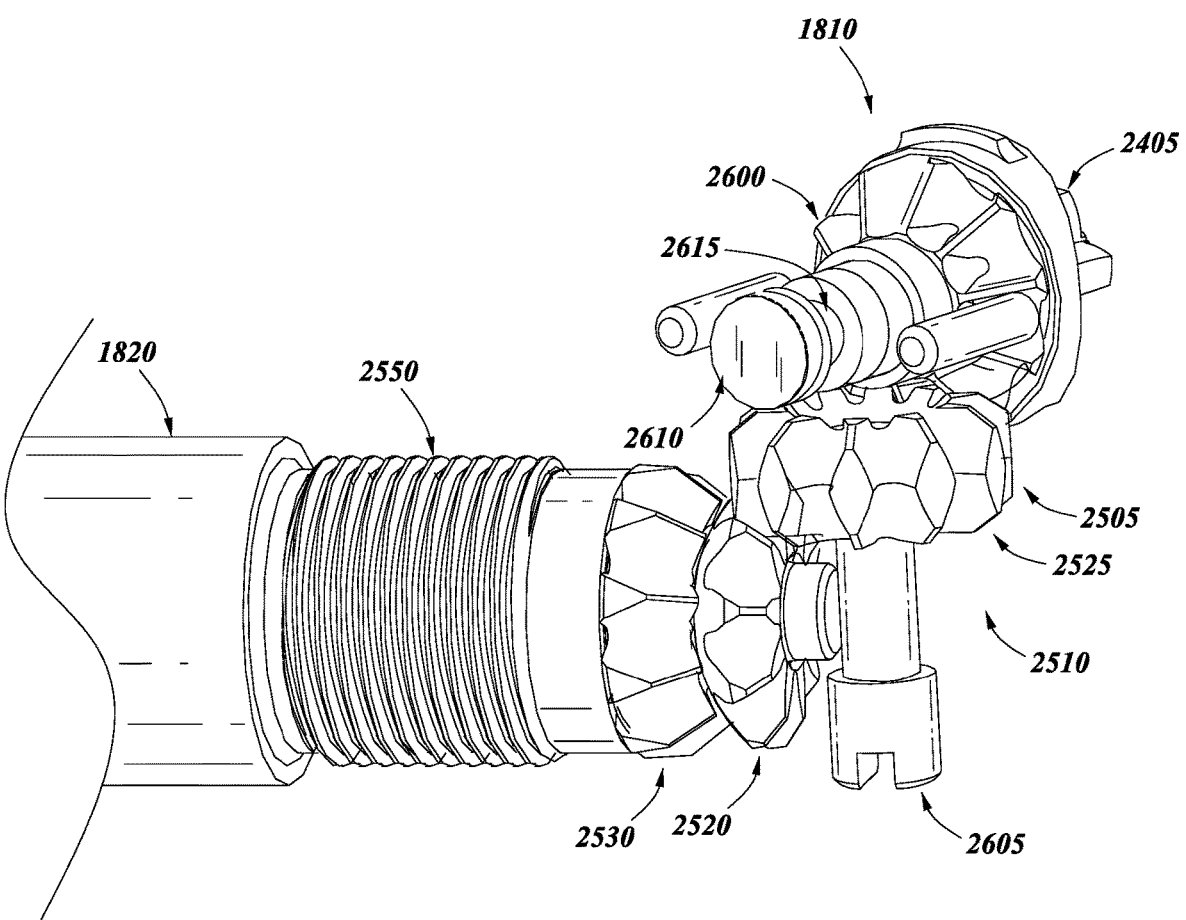

FIGS. 25 and 26 illustrate close-up views of the elongate outer housing 1905 and certain internal components of the turret driver head adapter 1810. As shown, a distal end of the elongate outer housing 1905 can have threads 2550, which can secure a cover 2400 (see FIG. 24). As also shown, the internal components of the turret driver head adapter 1810, may include multiple articulating assemblies, such as an articulating torque transmission unit 2510 and/or a articulation mechanism 2515. The articulating torque transmission unit 2510 and the articulation mechanism 2515 can be separate and/or independently operable (e.g., one can be operated without operation of the other). As discussed in more detail below, in certain embodiments, the unit 2510 can control the driver head 2405 and the mechanism 2515 can control the rotational position of the driver head adapter 1810.

In some embodiments, the articulating torque transmission unit 2510 comprises a gear assembly 2505 that transfers the torque from the second internal shaft 2305 to the driver head 2405 (e.g., a bit, drill bit, or other medical tool). In various embodiments, a proximal end of the second internal shaft 2305 can be coupled to the motor of the fastening system 1850. The torque can be transferred through the shaft 2305 to the gear assembly 2505 to the driver head 2405. In various embodiments, the articulating torque transmission unit 2510 preserves the direction of the motor. For example, the turret driver head adapter 1810 may rotate the driver head 2405 in the same direction as the motor rotates the second internal shaft 2305.

The gear assembly 2505 of the articulating torque transmission unit 2510 may include a plurality of gears, such as a first bevel gear 2520, a second bevel gear 2525, and a third bevel gear 2600. In some embodiments, the first bevel gear 2520 is fixedly coupled to the second internal shaft 2305, the second bevel gear 2525 is fixedly coupled to a gear support shaft 2605, and the third bevel gear 2600 is fixedly coupled to the output shaft 2610. The output shaft may be fixed to the driver head 2405 (e.g., bit). In some embodiments, shaft 2605 may be a shoulder screw to retain one or more components of the turret head adapter 1810. The gear support shaft 2605 may have a slot on the distal end (e.g., the end furthest from the corresponding gear) that may be used to tighten the shoulder screw into place during the assembly process of the articulating tool 1800. In some embodiments, the turret driver head adapter 1810 has one or more clevis pins with a cross pin (not shown) to eliminate the risk of one or more screws loosening. Thus, the articulating tool 1800 may be manufactured to remain firmly assembled during operation.

In some embodiments, the first bevel gear 2520 may interact (e.g., intermesh with) with the second bevel gear 2525. The second bevel gear 2525 may interact (e.g., intermesh) with the third bevel gear 2600. As shown in FIG. 26, the second bevel gear 2525 may comprise a double bevel gear, which has a bevel gear on two sides. Any type of gears (e.g., spur gears, helical gear, worm, gear, internal gear, etc.) may be used for any of the gear assemblies described herein.

In some embodiments, the articulation mechanism 2515 surrounds and/or is nested with the articulating torque transmission unit 2510. For example, as described above, the internal shaft 2305 of the articulating torque transmission unit 2510 may be located within a lumen of the internal shaft 2300 of the articulation mechanism 2515. In certain implementations, the second 2525 and third bevel gears 2600 of the articulating torque transmission unit 2510 can be located within a front cap 2540 of the turret driver head adapter 1810. The nesting of the articulating torque transmission unit 2510 and articulation mechanism 2515 allows the articulating tool 1800 to be smaller while maintaining a high degree of movement and torque transmission.

In some embodiments, the articulation mechanism 2515 is an orientation mechanism configured to position the driver head adapter 1810 in different orientations. The articulation mechanism 2515 may be a gear assembly 2500. The gear assembly 2500 may include a first bevel gear 2530 and a second bevel gear 2535. The first bevel gear 2530 may be fixedly coupled to the internal shaft 2300, and the second bevel gear 2535 may be fixedly coupled to the front cap 2540 of the turret driver head adapter 1810. The first bevel gear 2530 may interact (e.g., intermesh) with the second bevel gear 2535. As shown, in certain implementations, the first bevel gear 2530 of the mechanism 2515 has a larger outside diameter than the first bevel gear 2520 of the unit 2510 and/or the second bevel gear 2535 of the mechanism 2515 has a larger outside diameter than the second bevel gears 2525 of the unit 2510. As also shown, the first bevel gears 2520, 2530 can be coaxial and/or the second bevel gears 2525, 2535 can be coaxial. In some embodiments, the first bevel gears 2520, 2530 and the second bevel gears 2525, 2535 are configured to rotate around generally perpendicular axes.

As described above, the articulation mechanism 2515 may be configured to rotate the turret driver head adapter 1810 about the y-axis of the fastening tool 1820 when the corresponding internal shaft 2300 is rotated. In some embodiments, the second bevel gear 2535 has a mechanical stop 2545 that limits the rotation of the turret driver head adapter 1810. In some embodiments, the second bevel gear 2535 does not have mechanical stops and/or can rotate 360° about the y-axis.

In some embodiments, the position of the turret driver head adapter 1810 may be adjusted via one or more operator controls 110. For example, a user may be able to press one or more operator controls 110 (see FIG. 20) to rotate the fastening tool 1820 about the z-axis. In certain implementations, the one or more operator controls 110 may be used to rotate the turret driver head adapter 1810 about the y-axis.

Figure 27:
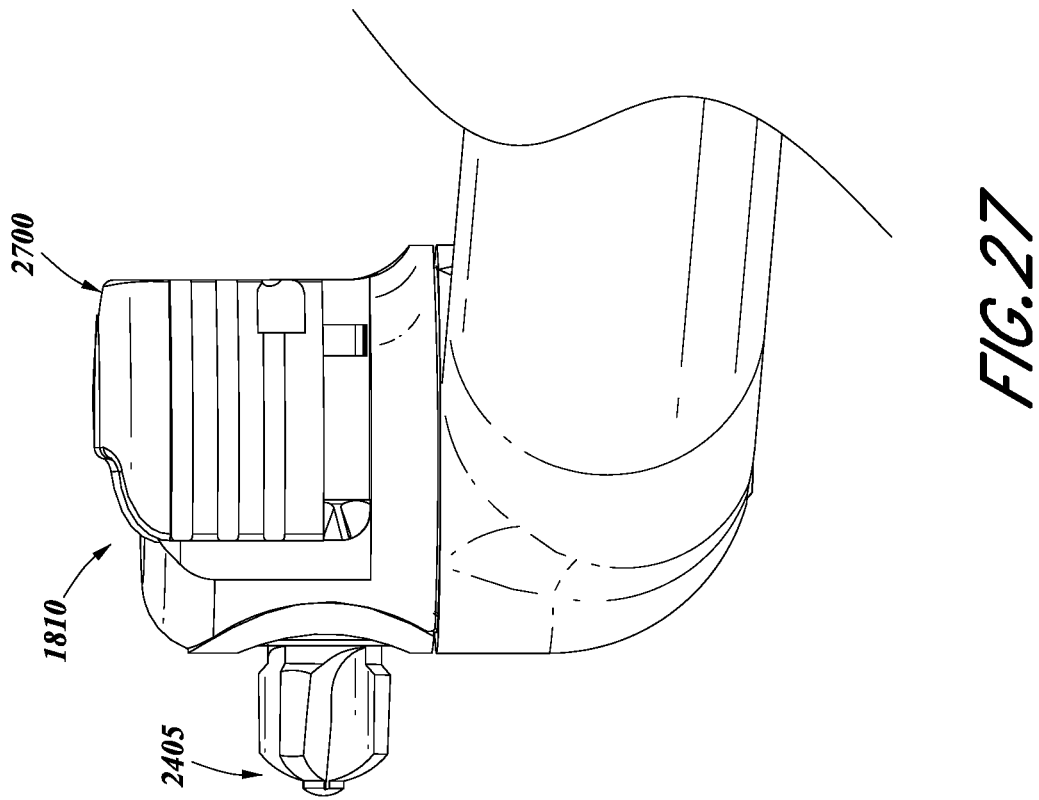
FIG. 27 illustrates a side view of the turret driver head adapter of FIG. 24.

FIG. 27 illustrates a side view of the turret driver head adapter 1810. In some embodiments, the turret driver head adapter 1810 includes a back cap 2700. The back cap 2700 protects the articulating torque transmission unit 2510 and the articulation mechanism 2515 from impact as well as from debris and dust.

In some embodiments, the back cap 2700 may be a sliding lock for the driver head 2405. For example, a user can slide the back cap 2700 along the y-axis to the unlocked position (e.g., the raised position shown in FIG. 27) to unlock the driver head 2405. In certain implementations, a user can slide the back cap 2700 to the locked position (e.g., the lower position shown in FIG. 24) to lock the driver head 2405. In some embodiments, lowering the back cap 2700 slides a tab into a groove 2615 of the driver head 2405. In some implementations, the back cap 2700 may use any of the coupling mechanisms described herein (e.g., friction fit, magnet, etc.). Thus, the back cap 2700 allows the driver head 2405 to be easily removed from the turret driver head adapter 1810. The quick removal of the driver head 2405 allows a user to easily change driver heads 2405 (e.g., from a screwdriver bit to a hex key) or change damaged driver heads 2405.

Figure 28:
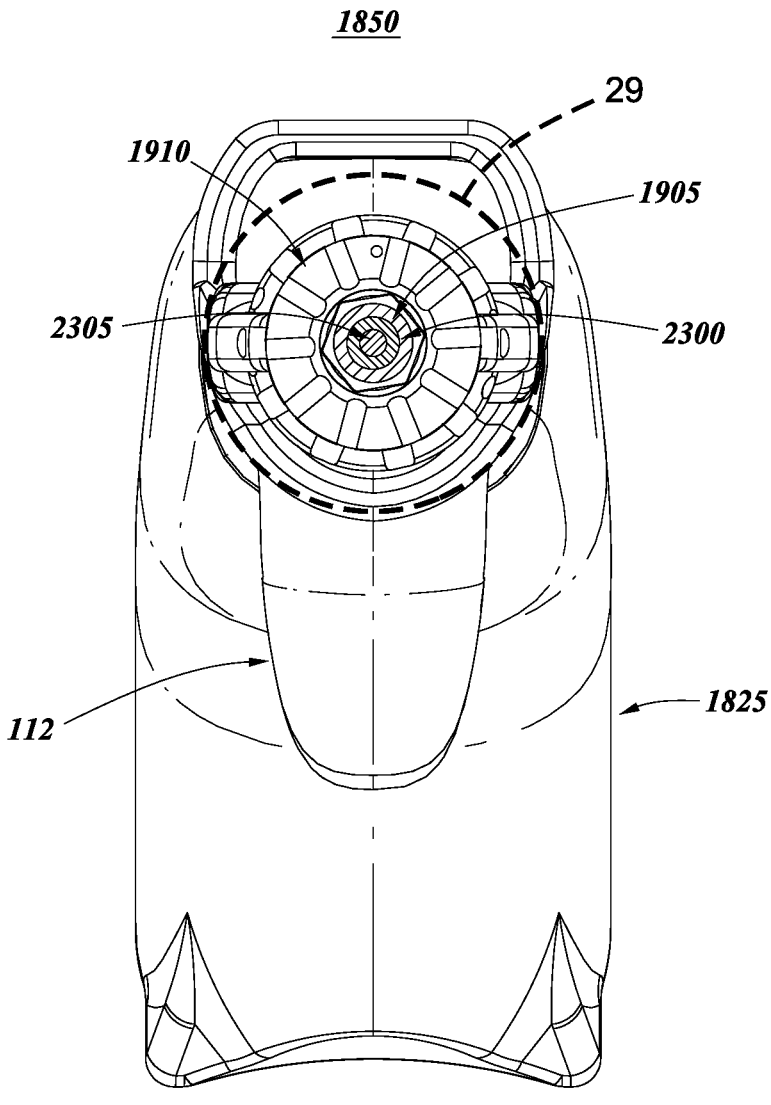
FIG. 28 illustrates a front cross-section view of the fastening system of FIG. 18.
Figure 29:
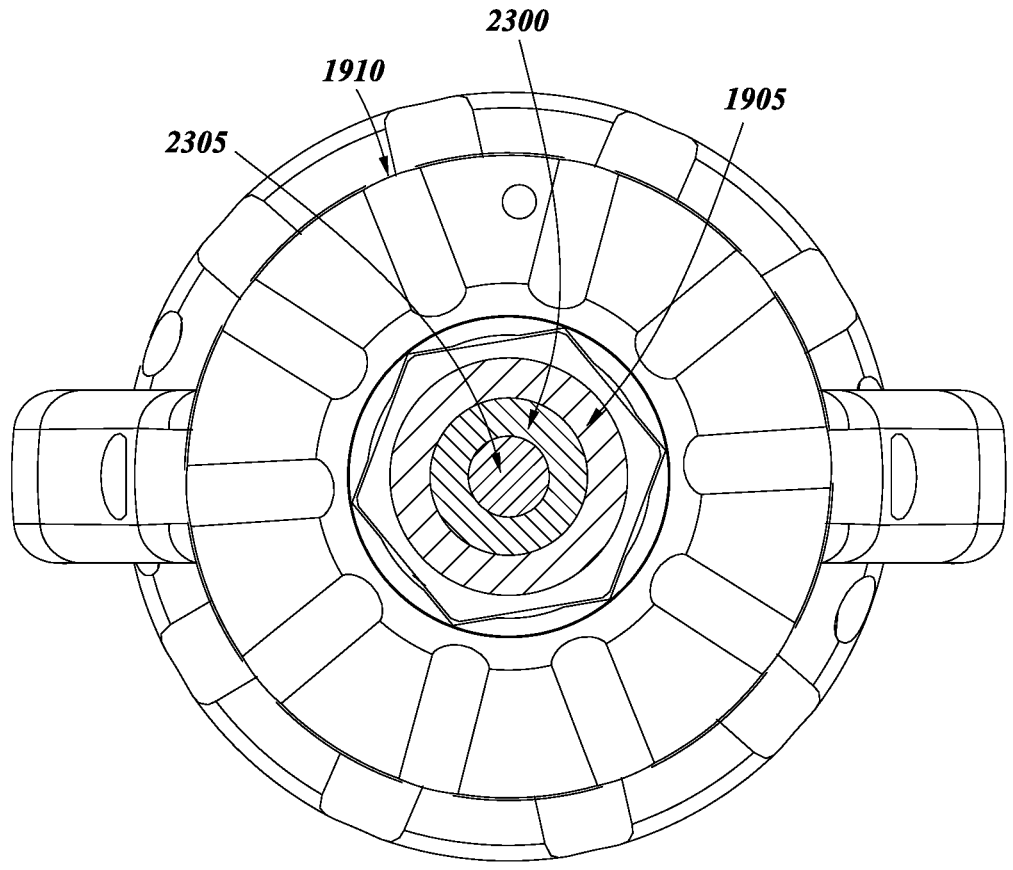
FIG. 29 illustrates a close-up cross-section view of the articulating tool of the fastening system of FIG. 18.

FIG. 28 illustrates a front cross-section view of an embodiment of the fastening system 1850. FIG. 29 illustrates a close-up cross-section view of an embodiment of the articulating tool 1800. In some embodiments, as described above, the fastening tool 1820 has three concentric shafts. For example, the fastening tool 1820 may include a first external shaft (e.g., the elongate outer housing 1905), a second shaft (e.g., internal shaft 2300) that is fixedly attached to the articulation mechanism 2515, and the third shaft (e.g., the second internal shaft 2305) that is fixedly attached to the articulating torque transmission unit 2510. The concentric shafts reduce the size of the fastening tool 1820 while allowing a user to effectively control and operate the turret driver head adapter 1810.

Figure 30:
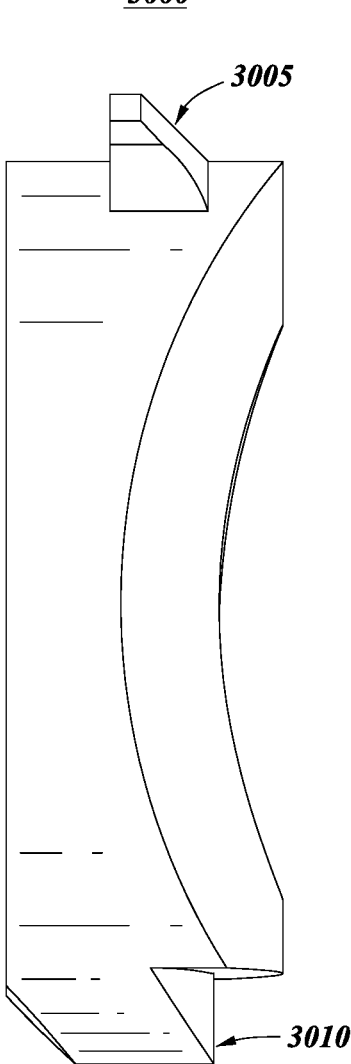
FIGS. 30-32 illustrate side and front views of a rounded front plate of a front cap of the turret driver head adapter of FIG. 24.
Figure 31:
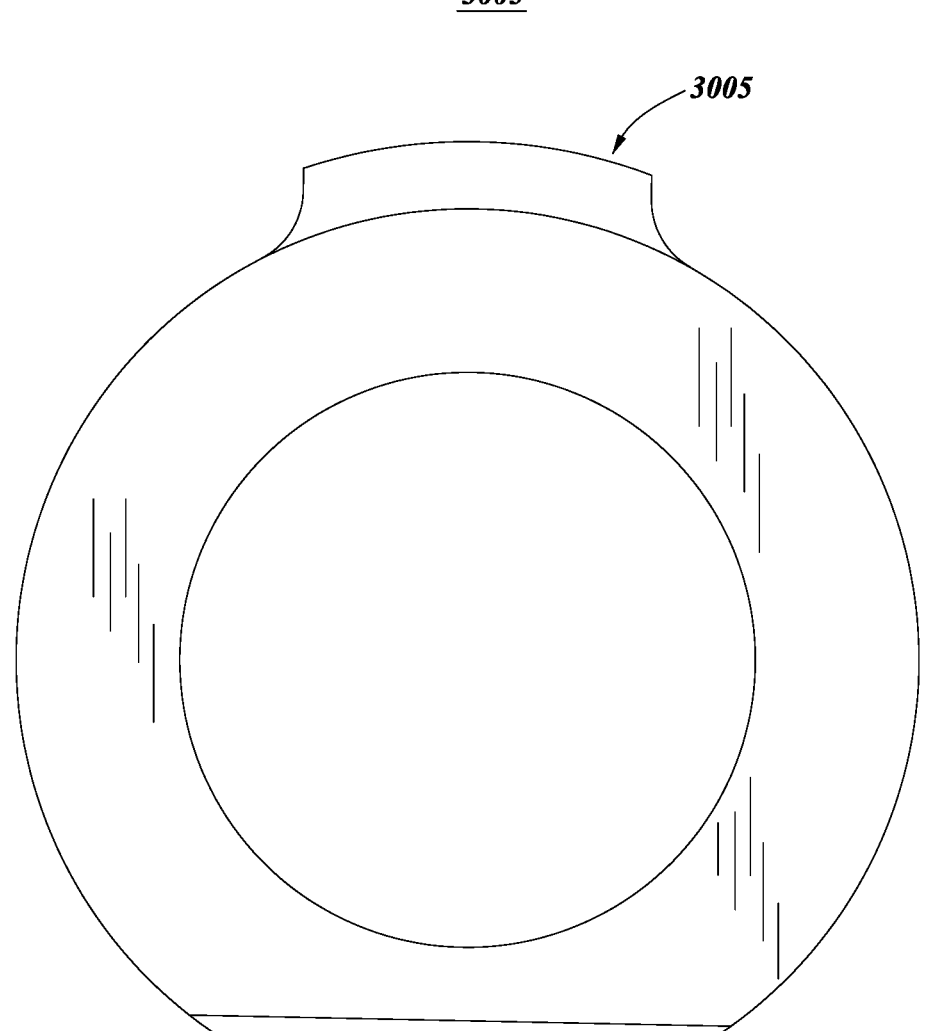
Figure 32:
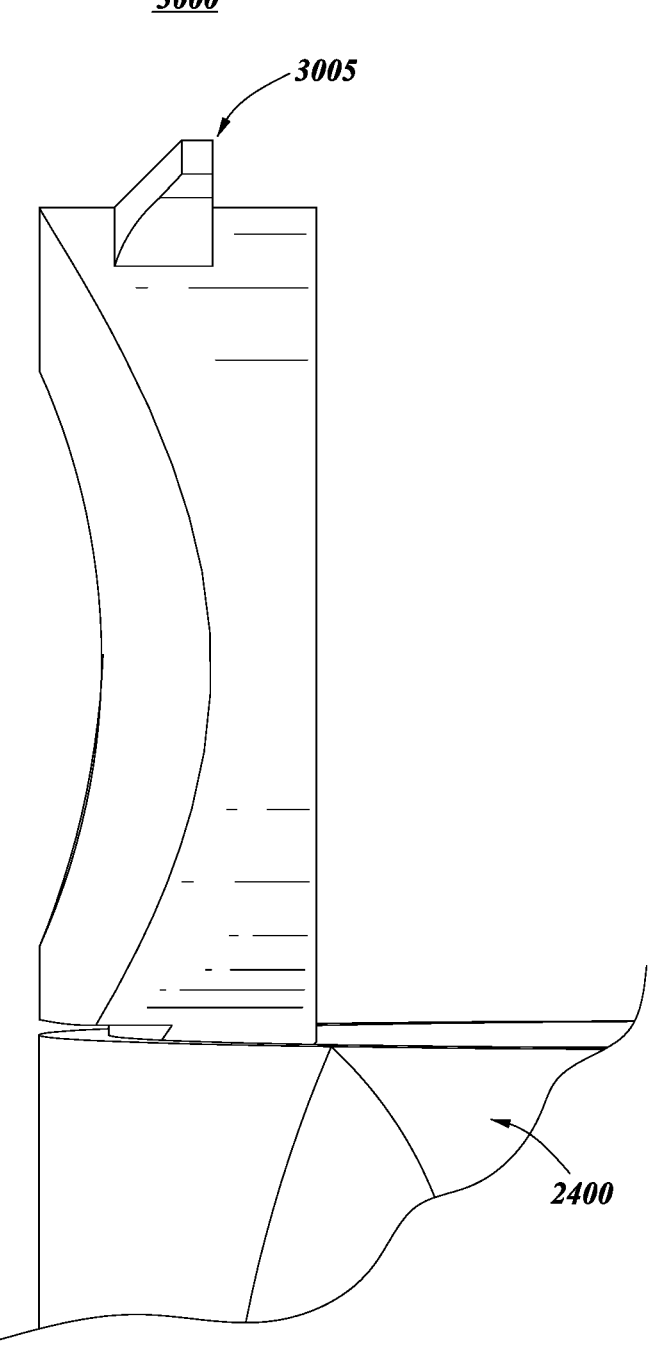

FIGS. 30-32 illustrate a rounded front plate 3000 of the front cap 2540 of the turret driver head adapter 1810. In some embodiments the rounded front plate 3000 is coupled to the front cap 2540 of the turret driver head adapter 1810 via the top 3005 and bottom lips 3010 of the rounded front plate 3000. For example, the top lip 3005 can be inserted into a top recess of the front cap 2540. In certain implementations, the bottom lip 3010 can be inserted into a bottom recess that is formed partially by the front cap 2540 and partially by the protective bottom housing 2400 of the turret driver head adapter 1810. As shown in FIG. 32, the protective bottom housing 2400 allows the bottom lip 3010 to slide along the recess when the turret driver head adapter 1810 rotates about the y-axis. The integrated rounded front plate 3000 may stabilize the driver head 2405 while allowing smooth rotation of the turret driver head adapter 1810.

Articulating Tool with Turret Driver Head Adapter (FIGS. 33-40)

Figure 33:
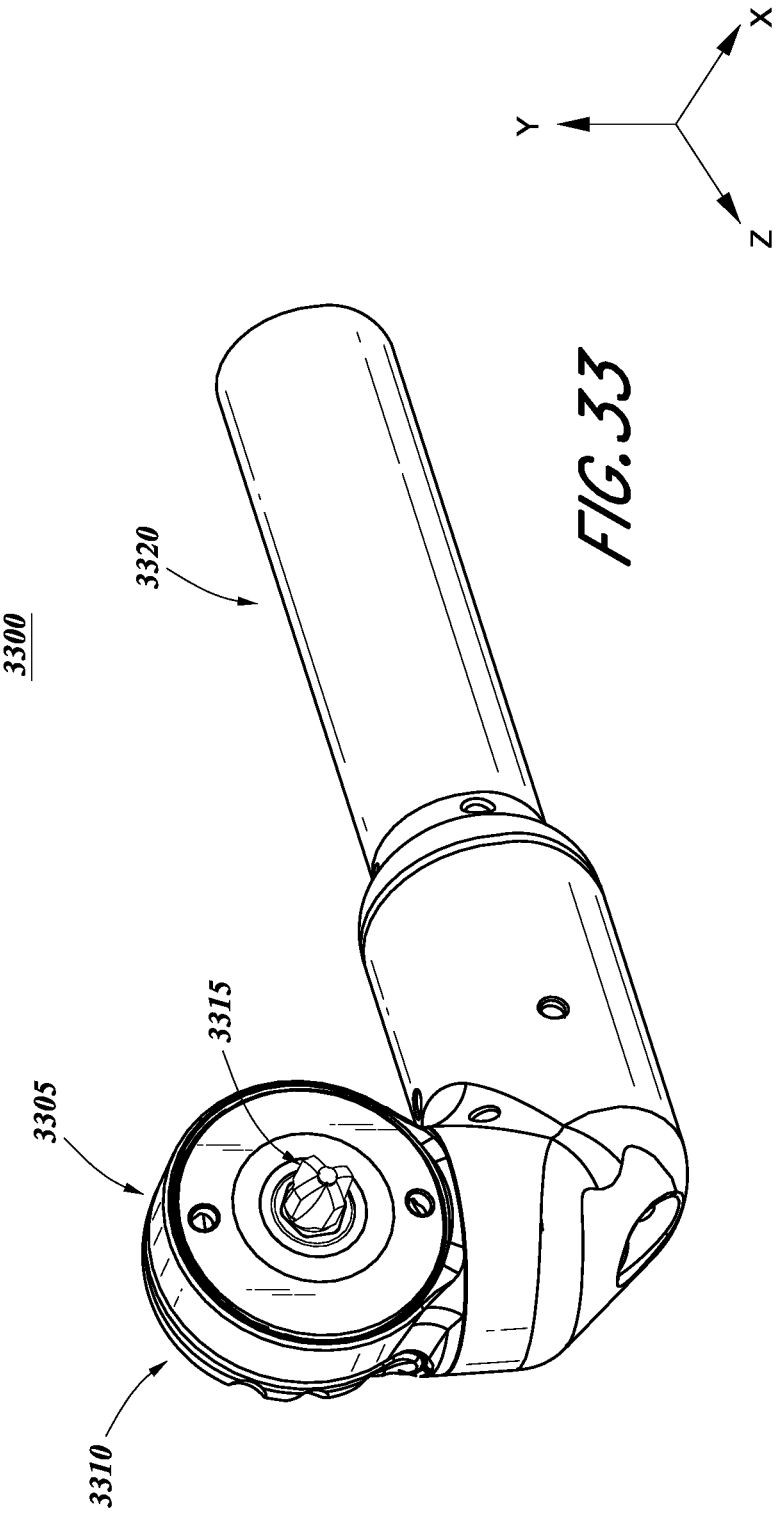
FIG. 33 illustrates a perspective view of a portion of an embodiment of a fastening tool that includes a turret driver head adapter.

FIG. 33 illustrates a perspective view of an embodiment of a portion of a fastening tool 3300 that includes a turret driver head adapter 3305. The tool 3300 may include any of the features of either of the tools 100, 1800, and vice versa. For example, the tool 3300 can include a handpiece, handpiece coupling assembly, body coupling assembly, and fastening tool (as discussed and shown above). For purposes of presentation, the following description and associated figures focus on a portion of the tool 3300, namely a distal end of the tool 3300 that includes the turret driver head adapter 3305.

The fastening tool 3300 may include an elongated outer shaft 3320, a turret driver head adapter 3305, back cap 3310, and driver head 3315. The fastening tool 3300 may be part of a fastening system that includes one or more controls to articulate the turret driver head adapter 3305 and/or driver head 3315. For example, the fastening tool 3300 may be incorporated into any of the fastening systems described above. In some embodiments, the turret driver head adapter 3305 is configured to rotate about the y-axis. The fastening tool 3300 may be configured to rotate about the z-axis relative to the handpiece of the fastening system.

Figure 34A:
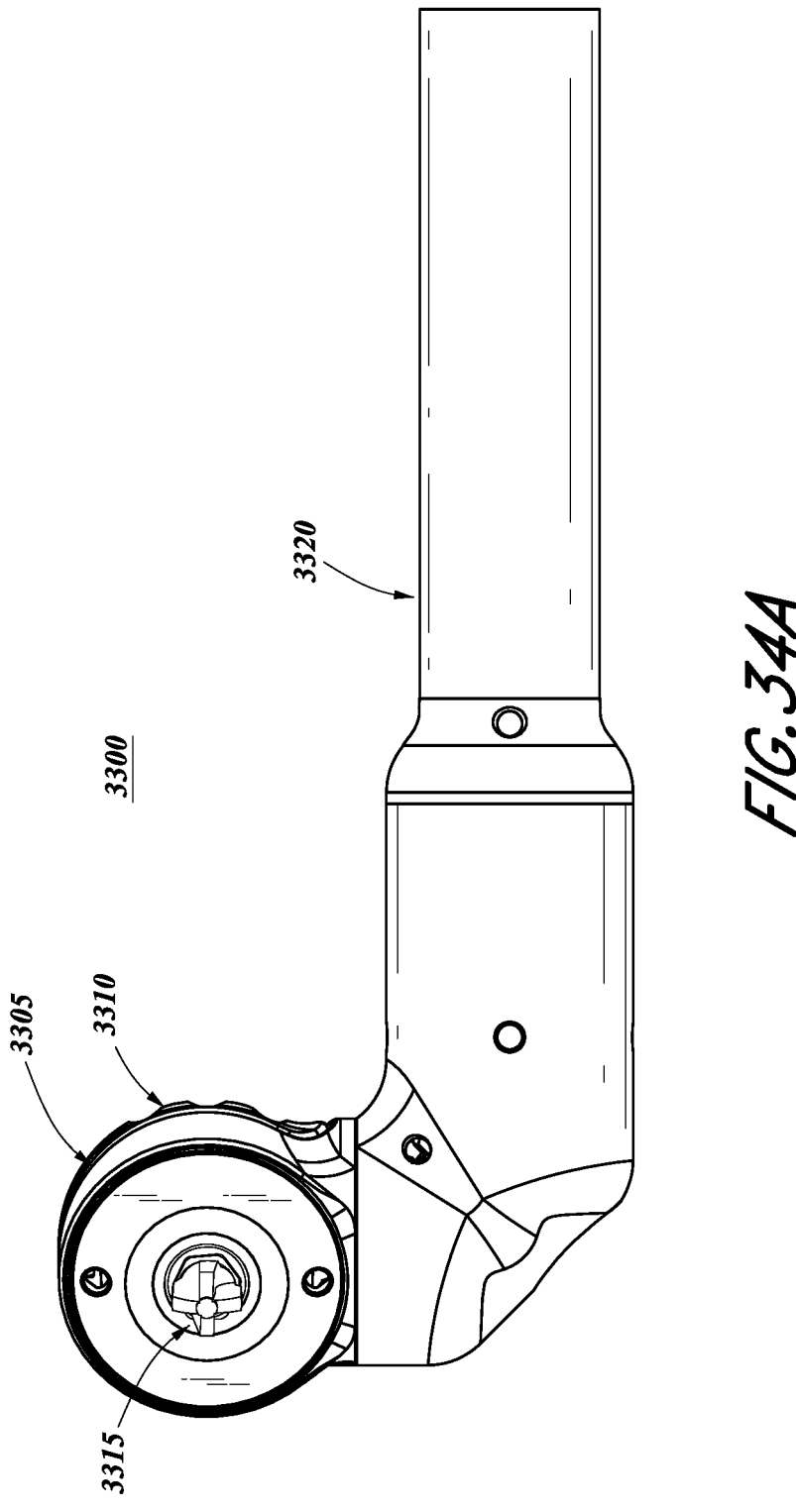
FIGS. 34A and 34B illustrate a right and left side view, respectively, of the fastening tool of FIG. 33.
Figure 34B:
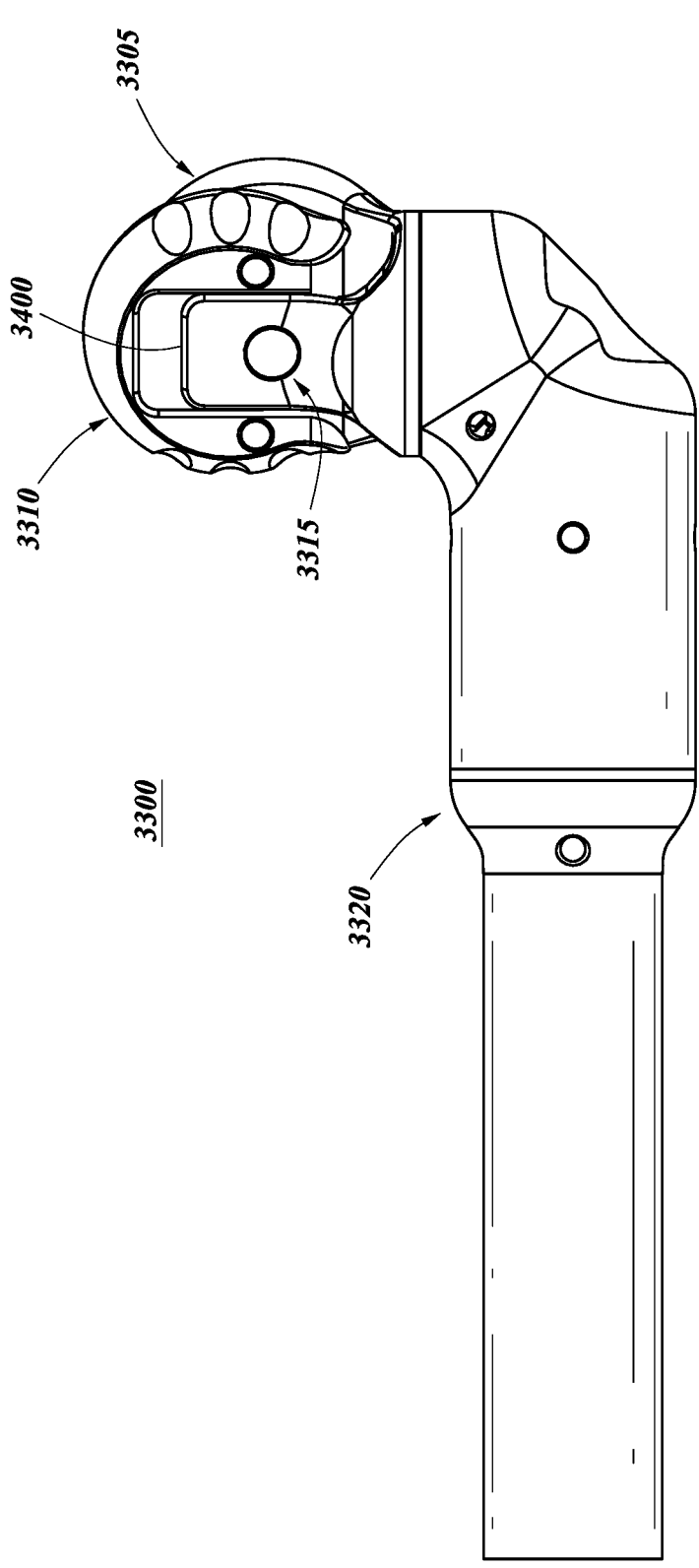

FIGS. 34A and 34B illustrate a front and back view, respectively, of the turret driver head adapter 3305. In some embodiments, the turret driver head adapter 3305 includes a back cap 3310. The back cap 3310 protects internal components of the fastening tool 3300 from impact as well as from moisture, debris, and dust. In some embodiments, the back cap 3310 may be a sliding lock for the turret driver head adapter 3305. For example, a user can slide the back cap 3310 along the y-axis to the unlocked position (e.g., the raised position shown in FIG. 34B) to unlock the driver head 3315. In certain implementations, a user can slide the back cap 3310 to the locked position (e.g., the lower position shown in FIG. 34A) to lock the driver head 3315. In some embodiments, lowering the back cap 3310 slides a tab 4000 into a groove (see 2615 of FIG. 26) of the driver head 3315 to lock the driver head 3315 in place. In some implementations, the back cap 3310 may use any of the coupling mechanisms described herein (e.g., friction fit, magnet, etc.). In some embodiments, the back cap 3310 is spring-loaded and automatically reverts to the locked position.

In some embodiments, the turret driver head adapter 3305 has a stabilizer 3400 that is configured to securely receive the end of a driver head 3315. As shown, in some embodiments, the driver head 3315 passes through the stabilizer 3400 and/or is generally flush with the back of the stabilizer 3400. In some implementations, the stabilizer 3400 can aid in positioning the driver head 3315 inside the driver head adapter 3305 and/or can reduce unwanted movement of the driver head 3315.

Figure 35:
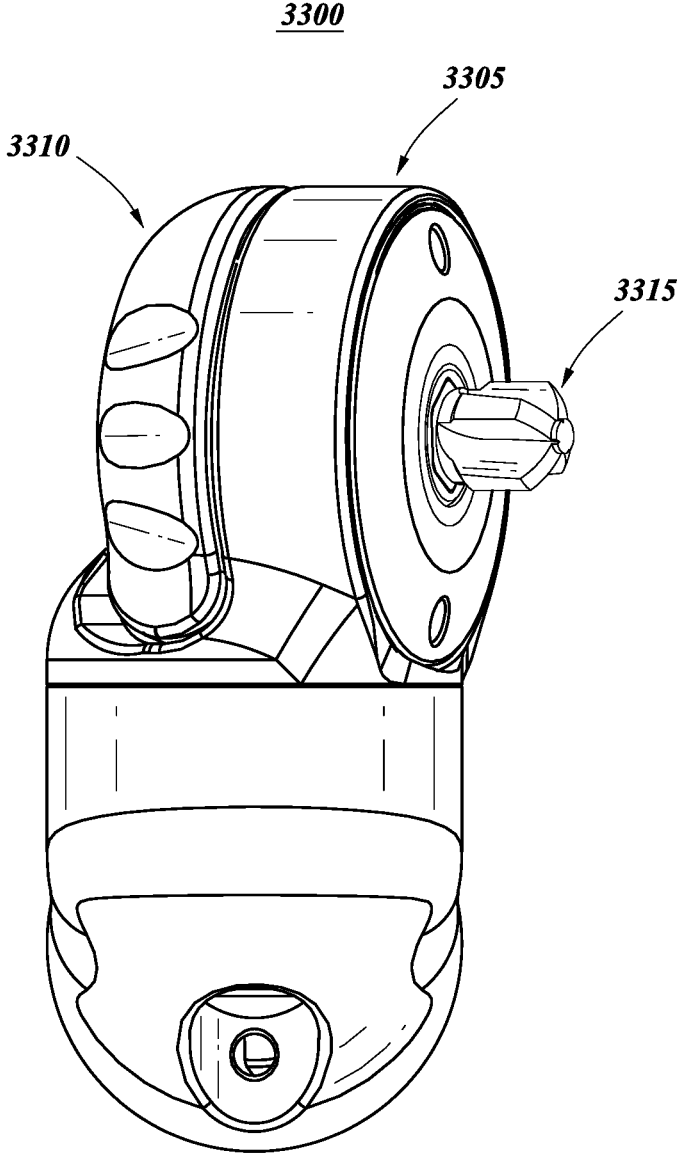
FIGS. 35 and 36 illustrate a front and back view, respectively, of the fastening tool of FIG. 33.
Figure 36:
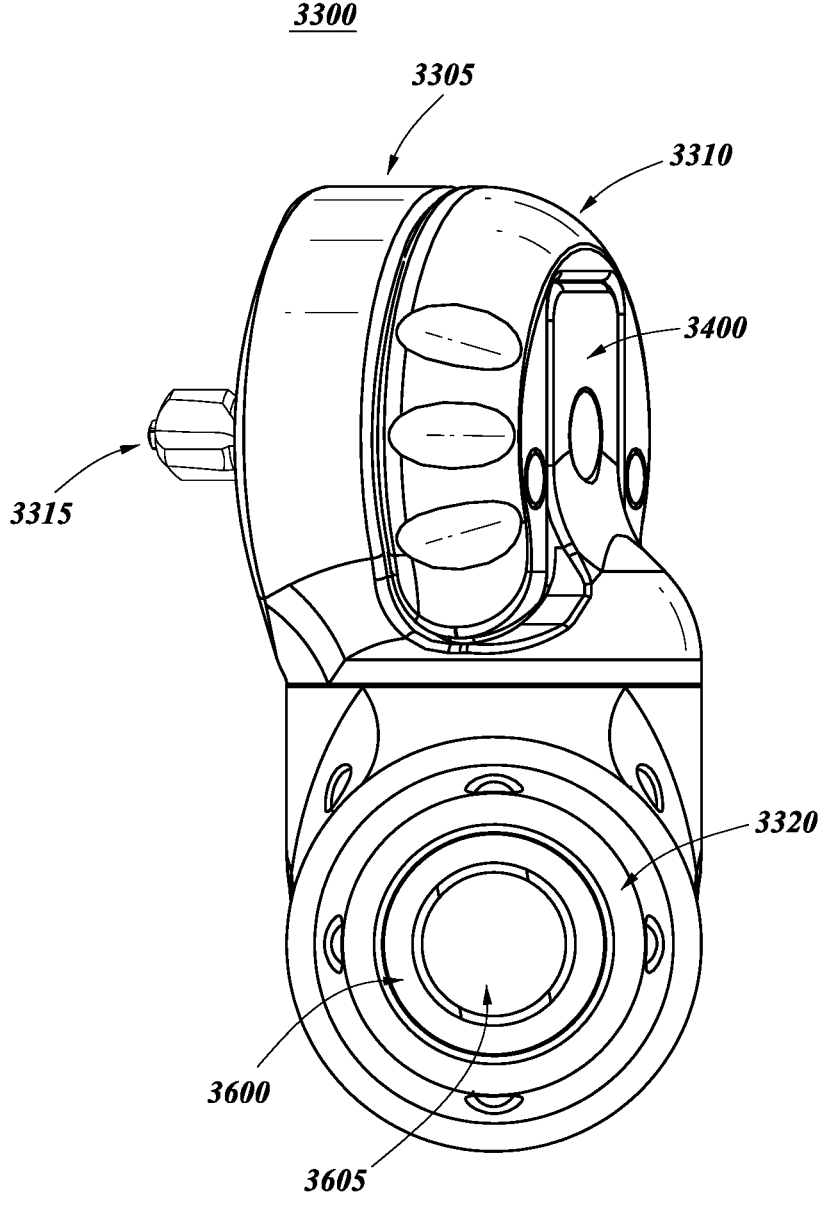
Figure 37A:
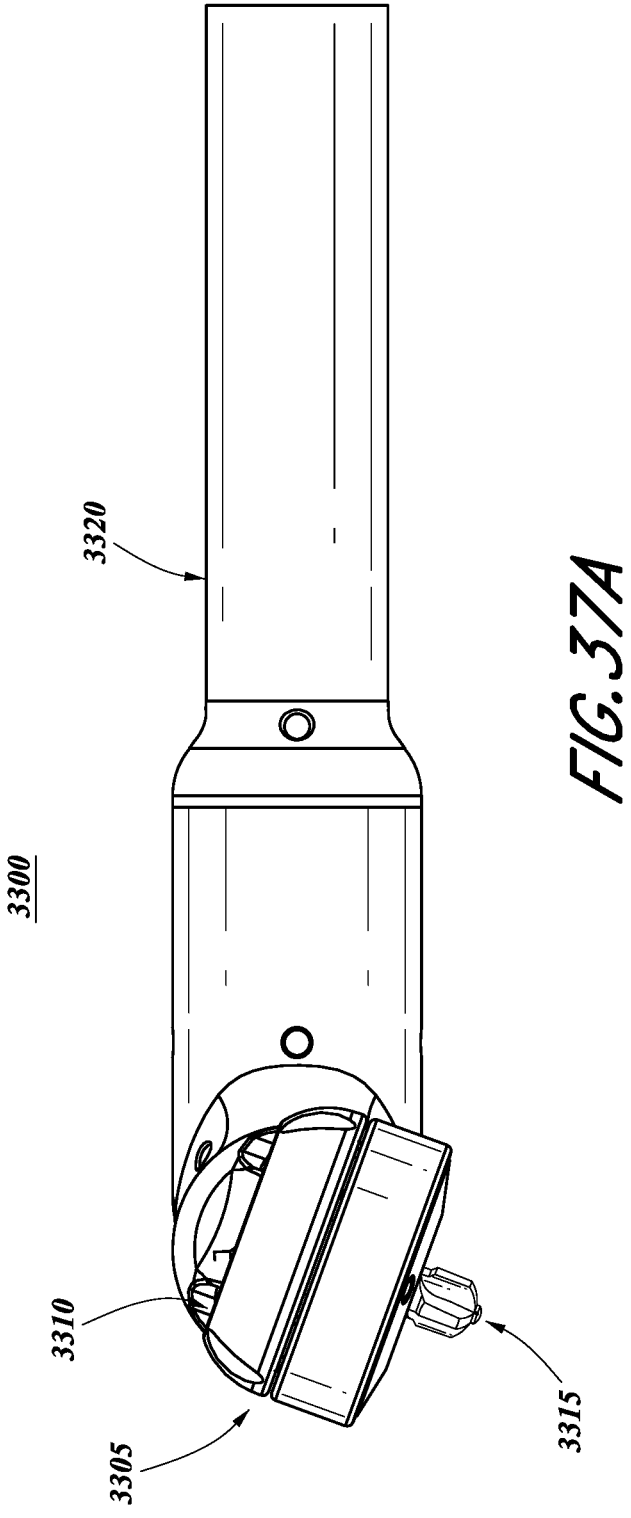
FIGS. 37A and 37B illustrate a top and bottom view, respectively, of the fastening tool of FIG. 33.
Figure 37B:
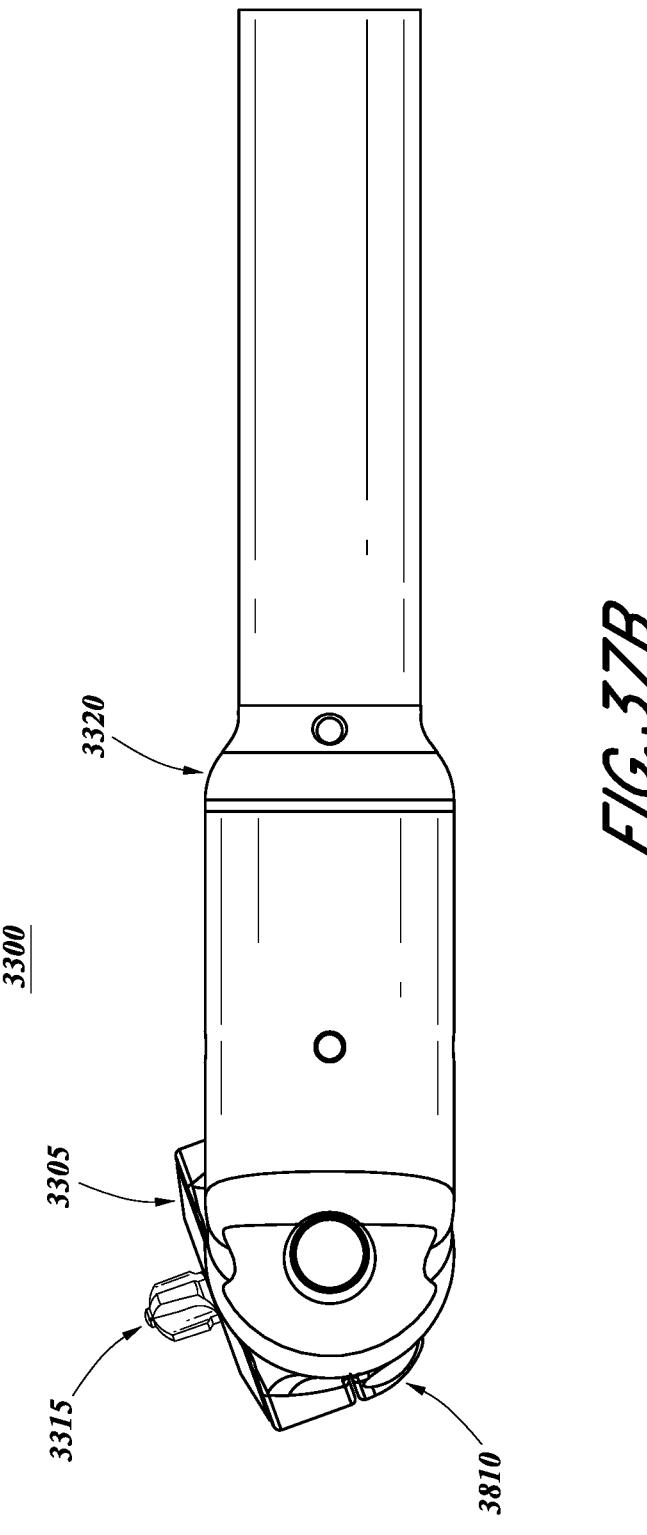

FIGS. 35 and 36 illustrate a front and back view, respectively, of the fastening tool 3300 that includes the turret driver head adapter 3305. FIGS. 37A and 37B illustrate a top and bottom view, respectively, of the fastening tool 3300. Similar to the previously discussed articulating tool 1800, the fastening tool 3300 may have three different shafts. For example, the fastening tool 3300 may have an elongated outer shaft 3320 that may be used to rotate the fastening tool 3300 about the z-axis, an internal shaft 3600 that may be used to rotate the turret driver head adapter 3305 about the y-axis, and a second internal shaft 3605 that may be used to transmit torque from a motor to the driver head 3315.

Figure 38:
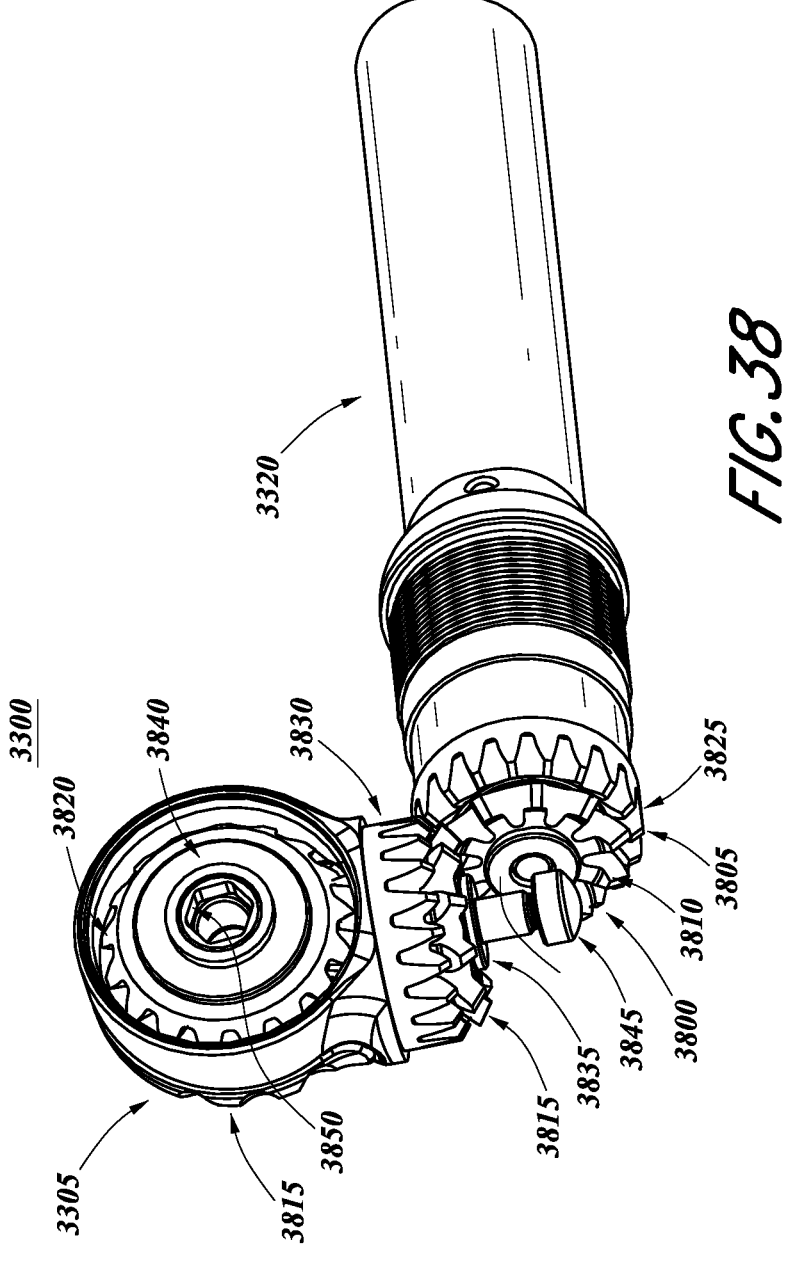
FIG. 38 illustrates a perspective view of certain internal components of the turret driver head adapter of the fastening tool of FIG. 33, with certain cover components not shown for purposes of presentation.

FIG. 38 illustrates a perspective view of internal components of the turret driver head adapter 3305, with certain cover components not shown for purposes of presentation. The internal components may include an articulating torque transmission unit 3800 and a separate articulation mechanism 3805. The unit 3800 and the mechanism 3805 can be separate and/or independently operable (e.g., one can be operated without operation of the other).

In some embodiments, the articulating torque transmission unit 3800 comprises a gear assembly that transfers the torque from the second internal shaft 3605 to the driver head 3315 (e.g., a bit, drill bit, or other medical tool). In some embodiments, the second internal shaft 3605 can be coupled to the motor of the fastening system. The gear assembly of the articulating torque transmission unit 3800 may include a first bevel gear 3810, a second bevel gear 3815, and a third bevel gear 3820. The bevel gears may have different pitch angles, gear ratios, or tooth depths to accommodate needs and user preference. For example, one or more of the gears may have a pitch angle of 0°, 5°, 10°, 20°, 50°, 70°, 90°, more than 90°, or any angle in-between. In some implementations, one or more gears may have a tooth depth of 1 mm, 2 mm, 5 mm, 10 mm, more than 10 mm, or any length in-between. In some embodiments, the first bevel gear 3810 is fixedly coupled to the second internal shaft 3605, the second bevel gear 3815 is fixedly coupled to a gear support shaft 3845, and the third bevel gear 3820 is removably coupled to the driver head 3315. The first bevel gear 3810 may intermesh with the second bevel gear 3815, and the second bevel gear 3815 may intermesh with the third bevel gear 3820. Various gear ratios may be implemented between any of the gears described herein. For example, the ratio between the first 3810 and second bevel gears 3815 may be 1:1, 2:1, 3:1, 4:1, 1:2, 1:3, 1:4 or any other ratio.

In some embodiments, the articulation mechanism 3805 surrounds the articulating torque transmission unit 3800. For example, as described above, the second internal shaft 3605 of the articulating torque transmission unit 3800 may be located within a lumen of the internal shaft 3600 of the articulation mechanism 3805. In certain implementations, the second 3815 and third bevel gears 3820 of the articulating torque transmission unit 3800 can be located within the front cap 3855 of the turret driver head adapter 3305.

In some embodiments, the articulation mechanism 3805 may be a gear assembly. The gear assembly may include a first bevel gear 3825 and a second bevel gear 3830. The first bevel gear 3825 may be fixedly coupled to the internal shaft 3600, and the second bevel gear 3830 may be fixedly coupled to the front cap 3855 of the turret driver head adapter 3305. The first bevel gear 3825 may intermesh with the second bevel gear 3830. As described above, the articulation mechanism 3805 may be configured to rotate the turret driver head adapter 3305 about the y-axis of the fastening tool 3300 when the corresponding internal shaft 3600 is rotated. In some embodiments, the second bevel gear 3830 can rotate 360° about the y-axis. In some embodiments, the turret driver head adapter 3305 can rotate multiple times about the y-axis.

Similar to the previously described embodiments, the position of the turret driver head adapter 3305 may be adjusted via one or more operator controls or control wheels. For example, a user may be able to press one or more operator controls to rotate the fastening tool 3300 about the z-axis. In certain implementations, the one or more operator controls or control wheels may be used to rotate the turret driver head adapter 3305 about the y-axis.

In some embodiments, the fastening tool 3300 includes one or more washers 3835, 3840. The one or more washers 3835, 3840 may be made of a low-friction material, such as a polymer. The one or more washers 3835, 3840 may reduce the area of metal-on-metal contact and/or may improve the durability and reliability of the fastening tool 3300. The one or more washers 3835, 3840 may reduce vibrations and protect the internal components from moisture, dust, and debris.

Figure 39:
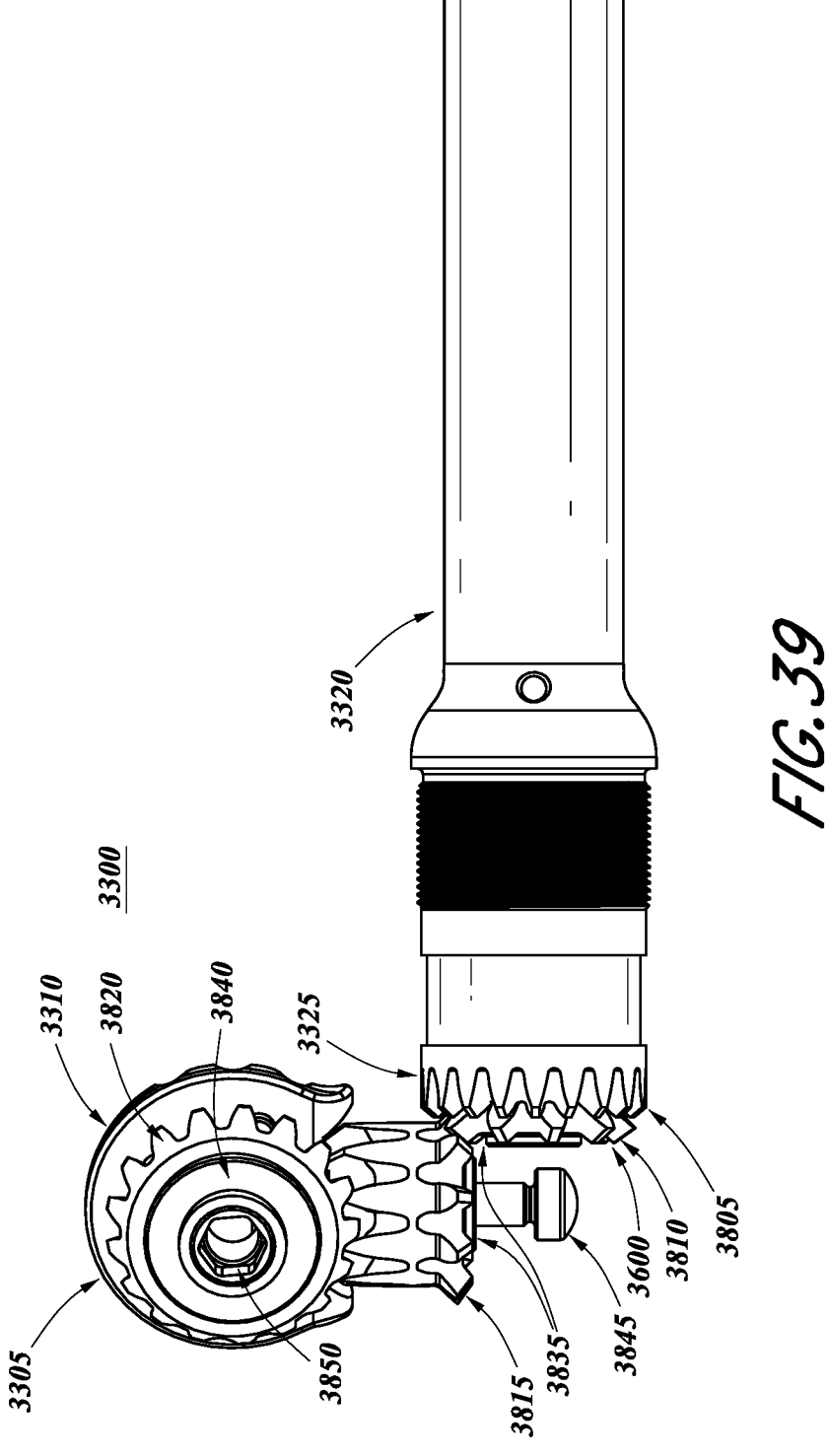
FIGS. 39 and 40 illustrate a front and back view, respectively, of the internal components of the turret driver head adapter of FIG. 38.
Figure 40:
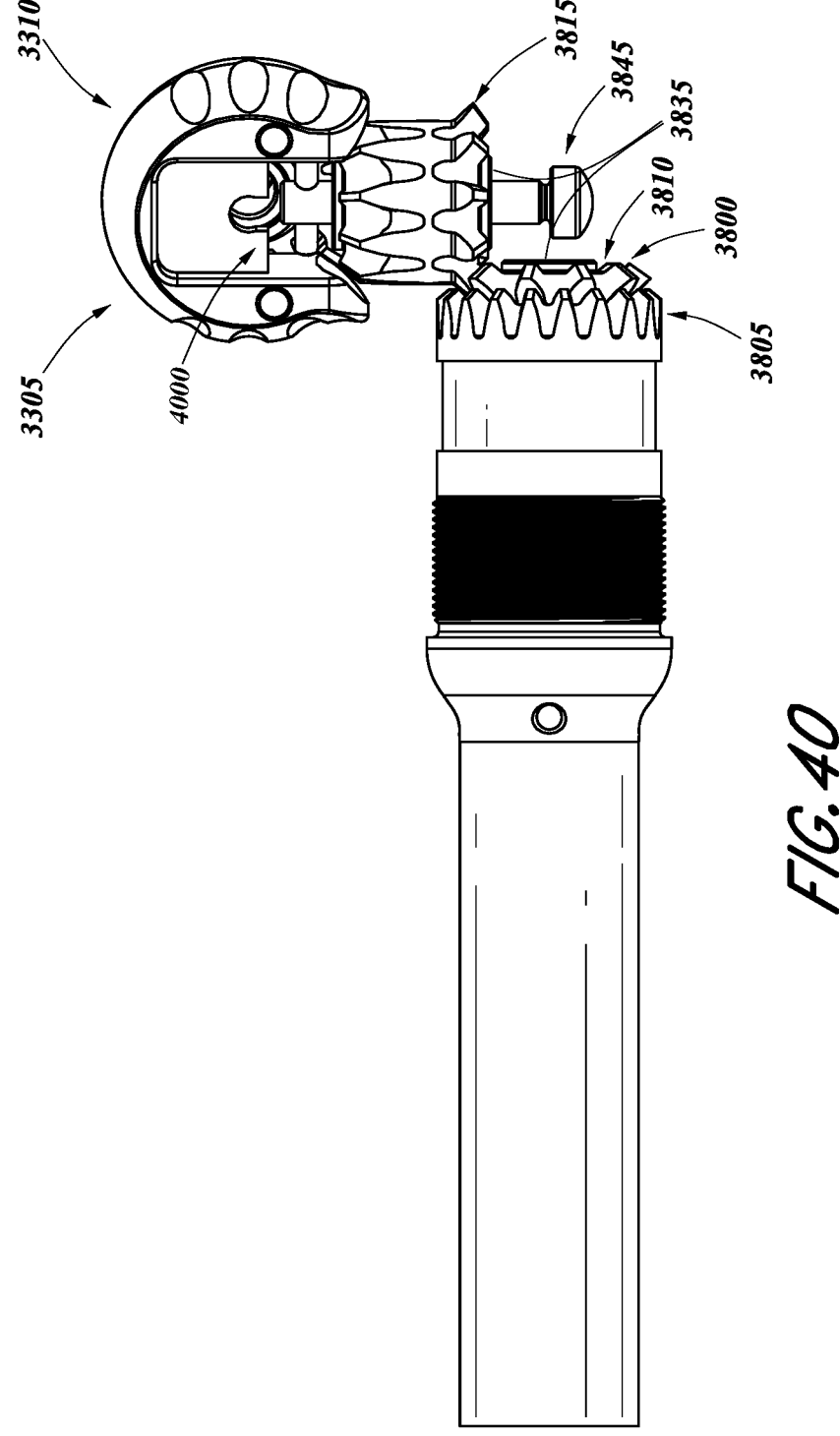

FIGS. 39 and 40 illustrate a front and back view, respectively, of an embodiment of the internal components of the turret driver head adapter 3305. In some embodiments, long gears are used in the articulating torque transmission unit 3800 and/or articulation mechanism 3805. For example, the second bevel gear 3815 of the articulation mechanism 3805 may be a high-capacity gear that has larger teeth (e.g., increase tooth thickness and depth), enhanced material strength (e.g., improved heat treatment), and precision manufacturing. The high-capacity gears can handle heavy loads and transmit significant torque while reducing wear and tear and noise. For example, the second bevel gear 3815 may have a larger diameter, increased contact ratio, and/or wider teeth compared to traditional gears. Thus, the high-capacity gear may transfer higher amounts of torque without sheering. It should be noted that any of the gears disclosed herein may be high-capacity gears.

In some embodiments, the second bevel gear 3815 may be a double-sided bevel gear. Advantageously, the double-sided gear 3815 may have more strength compared to two separate bevel gears connected by a shaft. For instance, the double-sided gear 3815 may have more material at the root of the gear teeth to resist bending. In some embodiments, greater torque may be required as wear and tear increases the friction between the various components of the articulating torque transmission unit 3800. To increase the longevity of the fastening tool 3300, the second bevel gear 3815 may have larger teeth on the input end to safely receive and transmit large amounts of torque. Therefore, the second bevel gear 3815 may reduce the likelihood of gears 3810 and 3815 experiencing binding issues.

In some embodiments, the double-sided gear 3815 may be easier to manufacture than other gears (e.g., two separate but connected bevel gears). For instance, the manufacture of the second bevel gear 3815 may not require the two opposite sides to be timed or indexed since they are monolithic. In some embodiments, the second bevel gear 3815 may have a smaller internal diameter than other gears due to its monolithic structure which may reduce the friction between the gear 3815 and the gear support shaft 3845.

For example, in some implementations, the teeth on the proximal end (e.g., the teeth that intermesh with first bevel gear 3810) of the second bevel gear 3815 may have a different number of teeth, pitch angle, thickness, and/or contact ratio than the teeth on the distal end (e.g., the teeth that intermesh with the third bevel gear 3820) of the second bevel gear 3815. Thus, the double-sided bevel gear may be able to provide different mechanical advantages for each side of teeth while reducing the overall weight of the gear (e.g., compared to two bevel gears being connected by a shaft). Any of the gears disclosed herein may be double-sided bevel gears.

Figure 41:
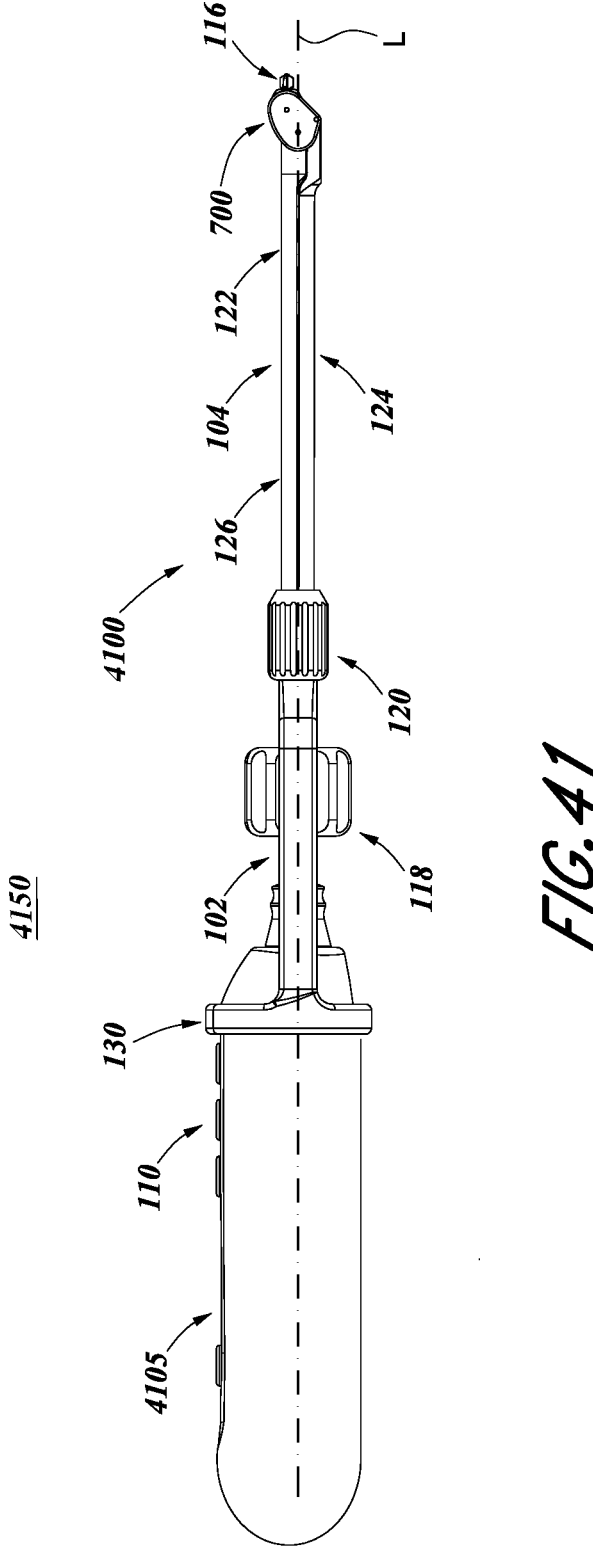
FIG. 41 illustrates an embodiment of a fastening system that includes a handpiece with a handle.

FIG. 41 illustrates an embodiment of a fastening system 4150 that includes a handpiece 4105. The handpiece 4105 can include a handle, which can be cylindrical or otherwise. In some embodiments, a user may rotate all or a portion of the handpiece 4105 about the longitudinal axis of the articulating tool 4100 to rotate the driver head 116. For example, in some embodiments, a user may rotate the handpiece 4105 while holding the body coupling assembly 102 stationary to rotate the driver head 116. In some embodiments, the handpiece 4105 and the body coupling assembly 102 may be coupled via bearings, slides, or bushings that allow independent rotational motion between the components. The handpiece 4105 may take a variety of different shapes and sizes. In some embodiments, the handpiece 4105 is cylindrical and/or tapered at both ends. In some instances, the handpiece 106 does not have a fin 112 or a compartment for a battery and motor. The handpiece 4105 may be used with any embodiments of the articulating tools described herein.

Certain Terminology

Conditional language used herein, such as, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. The term "and/or" means that "and" applies to some embodiments and "or" applies to some embodiments. Thus, A, B, and/or C is equivalent to A, B, and C written in one sentence and A, B, or C written in another sentence. The term "and/or" is used to avoid unnecessary redundancy.

The terms "approximately," "about," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may dictate, the term "generally parallel" can refer to something that departs from exactly parallel by less than or equal to 20 degrees and the term "generally perpendicular" can refer to something that departs from exactly perpendicular by less than or equal to 20 degrees.

Summary

This disclosure has presented certain embodiments, examples, and variations of articulating tools, systems, and methods. These articulating tools, systems, and methods allow users to easily reach (e.g., position a fastener in) a wide range of positions and configurations during medical procedures, such as by using multiple controls and shafts to change the orientation of the articulating tools. This disclosure extends beyond the specifically disclosed embodiments, examples, and variations to other alternative embodiments and/or uses of the invention, as well as obvious modifications and equivalents thereof. In addition, while a number of variations have been shown and described in detail, other modifications, which are within the scope of this disclosure, will be readily apparent to those of skill in the art based upon this disclosure. Moreover, while certain examples have been discussed in the context of attachments for surgical tools, the various inventions disclosed herein are not limited to use in surgical tools. Indeed, the various inventions disclosed herein are contemplated for in use a variety of other types of medical devices and other medical environments. Any of the tools, systems, or methods described herein can include any of the features disclosed in U.S. Pat. No. 11,259,855, the entirety of which is hereby incorporated by reference herein.

Some embodiments have been described in connection with the accompanying drawings. The figures are drawn to scale, but such scale should not be limiting, since dimensions and proportions other than what are shown are contemplated and are within the scope of this disclosure. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

Certain features have been described in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Any portion of any of the steps, processes, structures, and/or devices disclosed or illustrated in one embodiment, flowchart, or example in this disclosure can be combined or used with (or instead of) any other portion of any of the steps, processes, structures, and/or devices disclosed or illustrated in a different embodiment, flowchart, or example.

The embodiments and examples described herein are not intended to be discrete and separate from each other. Combinations, variations, and other implementations of the disclosed features are within the scope of this disclosure.

Any of the components or steps can be adjusted or modified. Other or additional steps can be used. None of the elements or steps described herein is essential or indispensable. Moreover, while operations may be depicted in the drawings or described in the specification in a particular order, such operations need not be performed in the particular order shown or in sequential order, and that all operations need not be performed, to achieve desirable results. Other operations that are not depicted or described can be incorporated in the described operations. For example, one or more additional operations can be performed before, after, simultaneously, or between any of the described operations. Further, the operations may be rearranged or reordered in other implementations. Also, the separation of various system components in the implementations described above should not be understood as requiring such separation in all implementations, and it should be understood that the described components and systems can generally be integrated together in a single product or packaged into multiple products.

The various features and processes described above may be used independently of one another, or may be combined in various ways. All possible combinations and subcombinations are intended to fall within the scope of this disclosure. The example systems and components described herein may be configured differently than described. For example, elements may be added to, removed from, or rearranged compared to the disclosed example embodiments.

In summary, various embodiments and examples of articulating tools, systems, and methods have been disclosed. Although the disclosure has been in the context of those embodiments and examples, this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments can be combined with, or substituted for, one another. Accordingly, the scope of this disclosure should not be limited by the particular disclosed embodiments described herein.

The following is claimed:

1. An articulating surgical tool comprising:
    an elongate outer housing comprising a proximal end, a distal end, a lumen, and a longitudinal axis, the elongate outer housing configured to engage with a handpiece comprising a motor;
    a torque transmission mechanism comprising:
        a first shaft that extends through the lumen of the elongate outer housing; and
        an articulating torque transmission unit having a first end and a second end, the first end being coupled to a distal portion of the first shaft, a first bevel gear, a second bevel gear, and a third bevel gear, wherein the first bevel gear is fixedly coupled to the first shaft, the second bevel gear is coupled to a gear support shaft, and the third bevel gear is configured to removably engage with a bit and to rotate the bit around a bit axis;
        wherein the torque transmission mechanism is configured to transmit torque from the motor to the bit, and wherein rotating the elongate outer housing is configured to rotate the torque transmission mechanism around the longitudinal axis; and an orientation mechanism that is separate from the torque transmission mechanism, the orientation mechanism comprising:

a second shaft extending through the lumen of the elongate outer housing, wherein the first shaft and second shaft are concentric;

a fourth bevel gear and a fifth bevel gear, wherein the fourth bevel gear is fixedly coupled to the second shaft, and the fifth bevel gear is coupled to a driver head adapter; and a controller connected to a proximal portion of the second shaft, the controller configured to rotate the second shaft, wherein the rotation of the second shaft rotates the driver head adapter around a transverse axis, wherein the transverse axis is generally perpendicular to the longitudinal axis.

2. The articulating surgical tool of claim 1, wherein the bit axis is non-coplanar with the longitudinal axis.

3. The articulating surgical tool of claim 2, wherein the second bevel gear is a double-sided bevel gear, and wherein the second bevel gear is between the longitudinal axis and the bit axis.

4. The articulating surgical tool of claim 1, wherein the bit is a bone drill bit.

5. An articulating tool configured to facilitate placement of fasteners during a medical procedure, the articulating tool comprising:

an elongate outer housing comprising a proximal end, a distal end, a lumen, and a longitudinal axis, the elongate outer housing configured to engage with a handpiece comprising a motor, the elongate outer housing connected to a wheel, wherein rotation of the wheel causes the elongate outer housing to rotate;

a torque transmission mechanism comprising:

a first shaft that extends through the lumen of the elongate outer housing;

an articulating torque transmission unit having a first end and a second end, the first end being coupled to a distal portion of the first shaft; and a driver head adapter that is positioned at the second end of the articulating torque transmission unit, the driver head adapter configured to removably engage with a bit and to rotate the bit around a bit axis, the bit configured to engage with a fastener;

wherein the torque transmission mechanism is configured to transmit torque from the motor to the driver head adapter and the bit, and wherein rotating the elongate outer housing is configured to rotate the torque transmission mechanism around the longitudinal axis; and an orientation mechanism that is separate from the torque transmission mechanism, the orientation mechanism comprising:

a second shaft extending through the lumen of the elongate outer housing; and a controller connected to a proximal portion of the second shaft, the controller configured to rotate the second shaft, wherein the driver head adapter is connected to the distal portion of the second shaft, and wherein the rotation of the second shaft rotates the driver head adapter around a transverse axis, wherein the transverse axis is generally perpendicular to the longitudinal axis.

6. The articulating tool of claim 5, wherein the orientation mechanism comprises a first bevel gear and second bevel gear, wherein the first bevel gear is fixedly coupled to the second shaft, and the second bevel gear is coupled to the driver head adapter.

7. The articulating tool of claim 5, wherein the driver head adapter is configured to rotate about the transverse axis between about 0° to about 360°.

8. The articulating tool of claim 7, wherein the driver head adapter is configured to complete multiple revolutions about the transverse axis.

9. The articulating tool of claim 5, wherein the articulating torque transmission unit comprises a first bevel gear, a second bevel gear, and a third bevel gear, wherein the first bevel gear is fixedly coupled to the first shaft, the second bevel gear is coupled to a gear support shaft, and the third bevel gear is removably coupled to the bit.

10. The articulating tool of claim 5, wherein the driver head adapter comprises a lumen configured to receive a shaft of the bit, and wherein the driver head adapter is coupled to the shaft of the bit via a quick-release mechanism.

11. The articulating tool of claim 5, wherein the elongate outer housing is configured to rotate about the longitudinal axis relative to the controller between about 0° to about 360°.

12. The articulating tool of claim 5, wherein the elongate outer housing is configured to complete multiple revolutions about the longitudinal axis relative to the controller.

13. The articulating tool of claim 5, wherein the controller comprises a wheel, wherein rotation of the wheel causes the second shaft to rotate.

14. The articulating tool of claim 13, wherein the controller includes a locking clutch that locks the rotation of the second shaft.

15. An articulating tool configured to facilitate placement of fasteners during a medical procedure, the articulating tool comprising:

an elongate outer housing comprising a proximal end, a distal end, a lumen, and a longitudinal axis, the elongate outer housing configured to engage with a handpiece comprising a motor;

a torque transmission mechanism comprising:

a first shaft that extends through the lumen of the elongate outer housing;

an articulating torque transmission unit having a first end and a second end, the first end being coupled to a distal portion of the first shaft; and a driver head adapter that is positioned at the second end of the articulating torque transmission unit, the driver head adapter configured to removably engage with a bit and to rotate the bit around a bit axis, the bit configured to engage with a fastener;

wherein the torque transmission mechanism is configured to transmit torque from the motor to the driver head adapter and the bit, and wherein rotating the elongate outer housing is configured to rotate the torque transmission mechanism around the longitudinal axis; and an orientation mechanism that is separate from the torque transmission mechanism, the orientation mechanism comprising:

a second shaft extending through the lumen of the elongate outer housing;

a first bevel gear fixedly coupled to the second shaft;

a second bevel gear coupled to the driver head adapter; and a controller connected to a proximal portion of the second shaft, the controller configured to rotate the second shaft, wherein the driver head adapter is connected to the distal portion of the second shaft, and wherein the rotation of the second shaft rotates the driver head adapter around a transverse axis, wherein the transverse axis is generally perpendicular to the longitudinal axis.

16. The articulating tool of claim 15, wherein the elongate outer housing is connected to a wheel, and wherein rotation of the wheel causes the elongate outer housing to rotate.

17. An articulating tool configured to facilitate placement of fasteners during a medical procedure, the articulating tool comprising:

an elongate outer housing comprising a proximal end, a distal end, a lumen, and a longitudinal axis, the elongate outer housing configured to engage with a handpiece comprising a motor;

a torque transmission mechanism comprising:

a first shaft that extends through the lumen of the elongate outer housing;

an articulating torque transmission unit having a first end and a second end, the first end being coupled to a distal portion of the first shaft; and a driver head adapter that is positioned at the second end of the articulating torque transmission unit, the driver head adapter configured to removably engage with a bit and to rotate the bit around a bit axis, the bit configured to engage with a fastener;

wherein the torque transmission mechanism is configured to transmit torque from the motor to the driver head adapter and the bit, and wherein rotating the elongate outer housing is configured to rotate the torque transmission mechanism around the longitudinal axis; and an orientation mechanism that is separate from the torque transmission mechanism, the orientation mechanism comprising:

a second shaft extending through the lumen of the elongate outer housing; and a controller connected to a proximal portion of the second shaft, the controller configured to rotate the second shaft, wherein the driver head adapter is connected to the distal portion of the second shaft, and wherein the rotation of the second shaft rotates the driver head adapter around a transverse axis, wherein the transverse axis is generally perpendicular to the longitudinal axis, wherein the elongate outer housing is configured to complete multiple revolutions about the longitudinal axis relative to the controller.

* * * * *